(12) United States Patent
Ren et al.

(10) Patent No.: US 10,844,089 B2
(45) Date of Patent: *Nov. 24, 2020

(54) NUCLEAR SULFATED OXYSTEROL, POTENT REGULATOR OF LIPID HOMEOSTASIS, FOR THERAPY OF HYPERCHOLESTEROLEMIA, HYPERTRIGLYCERIDES, FATTY LIVER DISEASES, AND ATHEROSCLEROSIS

(71) Applicant: Virginia Commonwealth University, Richmond, VA (US)

(72) Inventors: Shunlin Ren, Richmond, VA (US); William M. Pandak, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/154,007

(22) Filed: Oct. 8, 2018

(65) Prior Publication Data
US 2019/0169225 A1    Jun. 6, 2019

Related U.S. Application Data

(63) Continuation of application No. 15/042,244, filed on Feb. 12, 2016, now Pat. No. 10,144,759, which is a continuation of application No. 13/766,839, filed on Feb. 14, 2013, now Pat. No. 9,321,802, which is a continuation of application No. 12/708,803, filed on Feb. 19, 2010, now Pat. No. 8,399,441, which is a continuation-in-part of application No. 11/739,330, filed on Apr. 24, 2007, now abandoned, and a continuation-in-part of application No. PCT/US2005/033874, filed on Sep. 21, 2005.

(60) Provisional application No. 61/154,063, filed on Feb. 20, 2009, provisional application No. 60/621,537, filed on Oct. 25, 2004.

(51) Int. Cl.
C07J 31/00     (2006.01)
C07J 9/00      (2006.01)
A61K 31/575    (2006.01)

(52) U.S. Cl.
CPC .......... *C07J 31/006* (2013.01); *A61K 31/575* (2013.01); *C07J 9/00* (2013.01)

(58) Field of Classification Search
CPC .......... C07J 9/00; C07J 31/006; A61K 31/575
See application file for complete search history.

(56) References Cited

U.S. PATENT DOCUMENTS

| | | |
|---|---|---|
| 3,822,254 A | 7/1974 | Partridge et al. |
| 3,836,527 A | 9/1974 | Irmscher et al. |
| 3,928,397 A | 12/1975 | Ikekawa et al. |
| 4,202,891 A | 5/1980 | Schroepfer et al. |
| 4,225,524 A | 9/1980 | Ochi et al. |
| 4,264,512 A | 4/1981 | Okamura et al. |
| 4,427,668 A | 1/1984 | Javitt |
| 4,743,597 A | 5/1988 | Javitt et al. |
| 5,599,659 A | 2/1997 | Brasile et al. |
| 6,645,953 B2 | 11/2003 | Gronvald et al. |
| 7,524,493 B2 | 4/2009 | Flugelman et al. |
| 8,399,441 B2 | 3/2013 | Ren et al. |
| 9,034,859 B2 | 5/2015 | Ren et al. |
| 9,321,802 B2 | 4/2016 | Ren et al. |
| 2001/0015676 A1 | 8/2001 | Hayden et al. |
| 2002/0107233 A1 | 8/2002 | Liao et al. |
| 2003/0153541 A1 | 8/2003 | Dudley et al. |
| 2004/0048838 A1 | 3/2004 | Gronvald et al. |
| 2004/0152681 A1 | 8/2004 | Liao et al. |
| 2005/0101573 A1 | 5/2005 | Faarup et al. |
| 2006/0025393 A1 | 2/2006 | Liao et al. |
| 2007/0197484 A1 | 8/2007 | Song et al. |
| 2007/0275939 A1 | 11/2007 | Ren et al. |
| 2008/0078099 A1 | 4/2008 | Schulz et al. |
| 2009/0088192 A1 | 4/2009 | Davis et al. |
| 2010/0093687 A1 | 4/2010 | Song et al. |
| 2010/0273761 A1 | 10/2010 | Ren et al. |
| 2011/0077245 A1 | 3/2011 | Van der Aa et al. |
| 2011/0160174 A1 | 6/2011 | Song et al. |

(Continued)

FOREIGN PATENT DOCUMENTS

| | | |
|---|---|---|
| CN | 13570003 | 7/2002 |
| EP | 0857173 | 11/2003 |

(Continued)

OTHER PUBLICATIONS

Hassanein, et al (2019) "Safety and Efficacy of DUR-928: A Potential New Therapy for Acute Alcoholic Hepatitis" AASLD; Abstract LB-09 (Durect C928-010 Trail); 1 page.

(Continued)

*Primary Examiner* — Barbara P Badio
(74) *Attorney, Agent, or Firm* — Khin K. Chin; Bozicevic, Field & Francis LLP

(57) ABSTRACT

The sulfated oxysterol 5-cholesten-3β, 25-diol 3-sulphate, a nuclear cholesterol metabolite that decreases lipid biosynthesis and increases cholesterol secretion and degradation, is provided as an agent to lower intracellular and serum cholesterol and/or triglycerides, and to prevent or treat lipid accumulation-associated inflammation and conditions associated with such inflammation. Methods which involve the use of this sulfated oxysterol to treat conditions associated with high cholesterol and/or high triglycerides and/or inflammation (e.g. hypercholesterolemia, hypertriglyceridemia, non-alcoholic fatty liver diseases, atherosclerosis, etc.) are also provided.

6 Claims, 39 Drawing Sheets

Specification includes a Sequence Listing.

(56) References Cited

U.S. PATENT DOCUMENTS

| | | | |
|---|---|---|---|
| 2012/0264816 | A1 | 10/2012 | Ren et al. |
| 2013/0143854 | A1 | 6/2013 | Ren et al. |
| 2015/0072962 | A1 | 3/2015 | Ren |
| 2018/0346509 | A9 | 12/2018 | Ren et al. |
| 2019/0269695 | A1 | 9/2019 | Ren et al. |
| 2019/0374554 | A1 | 12/2019 | Ren et al. |

FOREIGN PATENT DOCUMENTS

| | | |
|---|---|---|
| EP | 2842547 | 3/2015 |
| WO | WO 1993025568 | 12/1993 |
| WO | WO 1994003177 | 2/1994 |
| WO | WO 1995015165 | 6/1995 |
| WO | WO 1997000884 | 1/1997 |
| WO | WO 1999058549 | 11/1999 |
| WO | WO 2000066611 | 11/2000 |
| WO | WO 2001015676 | 3/2001 |
| WO | WO 2002062302 | 8/2002 |
| WO | WO 2002090375 | 11/2002 |
| WO | WO 2003039480 | 5/2003 |
| WO | WO 2006047022 | 5/2006 |
| WO | WO 2008/078099 | 7/2008 |
| WO | WO 2009088192 | 7/2009 |
| WO | WO 2011077245 | 6/2011 |
| WO | WO 2013036835 | 3/2013 |
| WO | WO 2013154752 | 10/2013 |
| WO | WO 2015100312 | 7/2015 |
| WO | WO 2016058000 | 4/2016 |
| WO | WO 2017019808 | 2/2017 |

OTHER PUBLICATIONS

Hassanein, et al (2019) "Safety and Efficacy of DUR-928: A Potential New Therapy for Acute Alcoholic Hepatitis"; AASLD; 22 pages.

Nograles and Krueger (2011) "Anti-cytokine therapies for psoriasis"; Exp Cell Res ;317(9); pp. 1293-1300.

Mcclain, et al (2019) "DUR-928 Therapy for Acute Alcoholic Hepatitis: A Pilot Study"; AASLD; Poster (Durect Corporation); 1 page.

Abildayeva et al., "24(S)-Hydroxycholesterol Participates in a Liver X Receptor-controlled Pathway in Astrocytes That Regulates Apolipoprotein E-Mediated Cholesterol Efflux", The Journal of Biological Chemistry, May 5, 2006, pp. 12799-12808, vol. 281, No. 18, American Society for Biochemistry and Molecular Biology, Inc.

ACCAD et al. "Cholesterol homeostasis: A role for oxysterols", Current Biology, 1998, p. R601-R604, vol. 8.

Adams et al., "Cholesterol and 25-Hydroxycholesterol Inhibit Activation of SREPBs by Different Mechanisms, Both Involving SCAP and Insigs", The Journal of Biological Chemistry, Dec. 10, 2004, pp. 52772-52780, vol. 279, No. 50, American Society for Biochemistry and Molecular Biology, Inc.

Agarwal et al., "CTLA-4 gene polymorphism confers susceptibility to primary biliary cirrhosis"; Journal of Hepatology vol. 32, Issue 4, Apr. 2000, pp. 538-541.

Ahmed et al., "PPARs and their Metabolic Modulation: New Mechanisms for Transcriptional Regulation?", Journal of Internal Medicine, 2007, vol. 262, p. 184-198.

Aksoy IA, et al., "Cholesterol Sulfation in human liver. Catalysis by dehydroepiandrosterone sulfotransferase"; Drug Metab Dispos. 21:268-276, 1993.

Australian New Zealand Clinical Trials Registry (ANZCTR), "an Intralesional Injection Study of DUR-928 in Psoriasis Patients" Trial ID ACRTN 12616001077459, Aug. 10, 2016, web.

Australian New Zealand Clinical Trials Registry (ANZCTR), "A Single Infusion of DUR-928 in Healthy Volunteers", Trial ID ACRTN 12616000856415, Jun. 30, 2016, web.

Australian New Zealand Clinical Trials Registry (ANZCTR), "A Single Injection Dose Study of DUR-928 in Patients with Impaired Kidney Function and Healthy Volunteers" Trial ID ACTRN 12616000389404, Jun. 24, 2016, web.

Australian New Zealand Clinical Trials Registry (ANZCTR), "A Single Oral Dose Study of DUR-928 in Nonalcoholic Steatohepatitis (NASH) Patients and Healthy Volunteers", Trial ID ACTRN 12515001355561, Dec. 14, 2015, web.

Australian New Zealand Clinical Trials Registry (ANZCTR), "A Single and Multiple Daily Injection Study of DUR-928 in Healthy Volunteers", Trial ID ACTRN 12615000903583, Aug. 28, 2015, web.

Australian New Zealand Clinical Trials Registry (ANZCTR), "A Multiple Daily Oral Dose Study of DUR-928 in Healthy Volunteers", Trial ID ACTRN 12615000267550, Mar. 20, 2015, web.

Australian New Zealand Clinical Trials Registry (ANZCTR), "First-in-Human, Single Ascending Oral Dose Study of DV-928 in Healthy Volunteers", Trial ID ACTRN 12614001022651, Sep. 24, 2014, web.

Axelson and Larsson, "27-Hydroxylated Low Density Lipoprotein (LDL) Cholesterol Can Be Converted to 7[alpha],27-3 Dihydroxy-4-cholesten-3-one (Cytosterone) before Suppressing Cholesterol Production in Normal Human Fibroblasts", The Journal of Biological Chemistry, May 31, 1996, pp. 12724-12736, vol. 271, No. 22, The American Society for D Biochemistry and Molecular Biology, Inc.

Babaev et al., "Macrophage expression of peroxisome proliferator-activated receptor-alpha reduces atherosclerosis in low-density lipoprotein receptor-deficient mice", Circulation, 2007, pp. 1404-1412, vol. 116.

Bai et al., "Oxysterol sulfation by cytosolic sulfotransferase suppresses liver X receptor/sterol regulatory element binding protein-1c signaling pathway and reduces serum and hepatic lipids in mouse models of nonalcoholic fatty liver disease", Metabolism, 2012, pp. 836-845, vol. 61, Elsevier.

Bai Q, et al., "Sulfation of 25-hydroxycholesterol by SULT2B1b decreases cellular lipids via the LXR/SREBP-1c signaling pathway in human aortic endothelial cells"; Atherosclerosis. Feb. 2011; 214(2): 350-356.

Beltowski, "Liver X Receptors (LXR) as Therapeutic Targets in Dyslipidemia", Cardiovascular Therapy, 2008, pp. 279-316, vol. 26.

Beaven SW, et al.; "Reciprocal Regulation of Hepatic and Adipose Lipogenesis by Liver X Receptors in Obesity and Insulin Resistance"; Cell Metabolism. 2013; 18, 106-117.

Bjoerkem, "Are side-chain oxidized oxysterols regulators also in vivo?", The Journal of Lipid Research, Apr. 2009, pp. S213-S218, vol. 50, American Society for Biochemistry and Molecular Biology, Inc.

Bocher V, et al., "Liver X Receptors: New Players in Atherogenesis?"; Current Opinion in Lipidology. 2003; 14(2):137-143.

Carey MC et al., "Solution properties of sulfated monohydroxy bile salts. Relative insolubility of the disodium salt of glycolithocholate sulfate"; Biochim.Biophys Acta 575:16-26, 1979.

Cha et al., "The Carbohydrate-Response Element-Binding Protein Is a Target Gen of LXR", Journal of Biological Chemistry, Jan. 5, 2007, pp. 743-751, vol. 282, No. 1.

Cha; Kim, "Sulfated oxysterol 25HC3S as a therapeutic target of non-alcoholic fatty liver disease", Metabolism, 2012, pp. 1055-1057, vol. 61, Elsevier.

Chapman E. et al., "Sulfotransferases: Structure, mechanism, biological activity, inhibition, and synthetic utility"; Angew.Chem. Int. Ed Engl 43:3526-3548, 2004.

Chen et al., "Enzymatic Reduction of Oxysterols Impairs LXR Signaling in Cultured Cells and the Livers of Mice", Cell Metab., Jan. 2007, pp. 73-79, vol. 5, No. 1, Elsevier.

Chen et al. "Influenza A virus infection activities cholesterol sulfotransferase (SUL T2B1 b) in the lung of female C57BU6 mice". Biol. Chem., Oct. 2011, pp. 869-876, vol. 392.

Cook et al., "24-Hydroxycholesterol Sulfation by Human Sytosolic Sulfotransferases: Formation of Monosulfates and Disulfates, Molecular Modeling, Sulfatase Sensitivity, and Inhibition of Liver X Receptor Activation", Drug Metabolism and Disposition, 2009, pp. 2069-2078, vol. 37, No. 10, The American Society for Pharmacology and Experimental Therapeutics.

(56) References Cited

OTHER PUBLICATIONS

Corsini et al. "Effects of 26-Aminocholesterol. 27-Hydroxycholesterol, and 25-Hydroxycholesterol on Proliferation and Cholesterol Homeostasis in Arterial Myocytes", Arteriosclerosis, Thrombosis, and Vascular Biology, 1995, pp. 420-428, vol. 15, American Heart Association.

Diczfalusy U. "On the Formation and Possible Biological Role of 25-hydroxycholesterol"; Biochimie. 2013; 95 (3):455-460.

Ducheix S, et al., "The Liver X Receptor: A Master Regulator of the Gut-Liver Axis and a Target for Non Alcoholic Fatty Liver Disease"; Biochemical Pharmacology. 2013; 86(1): 96-105.

Duvnjak et al., "Pathogenesis and management issues for non-alcoholic fatty liver disease"; World journal of gastroenterology, 13(34). pp. 4539-4550. 2007.

Englund et al., "25-hydroxycholesterol induces lipopolysaccharide-lolerance and decreases a lipopolysaccharide-induced TNF-[gamma] secretion inmacrophages", Atherosclerosis, 2001, pp. 61-71, vol. 158, Elsevier.

Falany CN., Sulfation and sulfotransferases. Introduction: changing view of sulfation and the cytosolic sulfotranferases, FASEB J. 11 1-2, 1997.

Fuda et al., "Mutational Analysis of Human Hydroxysteroid Sulfotransferase SUL T2B1 lsoforms Reveals That Exon 1B of the SULT2B1 Gene Produces Cholesterol Sulfotransferase, whereas Exon 1A Yields Pregnenolone Sulfotransferase", The Journal of Biological Chemistry, Sep. 27, 2002, pp. 36161-36166, vol. 277, No. 39, American Society for Biochemistry and Molecular Biology, Inc.

Fuda et al., "Oxysterols are substrates for cholesterol sulfotransferase", The Journal of Lipid Research, Mar. 2007, pp. 1343-1352, vol. 48, American Society for Biochemistry and Molecular Biology, Inc.

Geese; Raftogianis, "Biochemical Characterization and Tissue Distribution of Human SULT2B1", Biochemical and Biophysical Research Communications, 2001, pp. 280-289, vol. 288, Academic Press.

Gill et al., "Sterol regulators of cholesterol homeostasis and beyond: The oxysterol hypothesis revisited and revised", Progress in Lipid Research, 2008, pp. 391-404, vol. 47, Elsevier.

Javitt et al., "Cholesterol and hydroxycholesterol sulfotransferases: Identification, distinction from dehydroepiandrosterone sulfotransferase, and differential tissue expression". Endocrinology, vol. 142, pp. 2978-2984, 2001.

Ji et al., "Human Hydroxysteroid Sulfotransferase SULT2B1 Pharmacogenomics: Gene Sequence Variation and Functional Genomics", The Journal of Pharmacology and Experimental Therapeutics, 2007, pp. 529-540, vol. 322, No. 2, The American Society for Pharmacology and Experimental Therapeutics.

Kase et al., "Liver X receptor antagonist reduces lipid formation and increases glucose metabolism in myotubes from lean, obese and type 2 diabetic individuals", Diabetologia, 2007, pp. 2171-2180, vol. 50, Springer-Verlag.

Kasakabe, Toru, et al (2010) "Congenital deficiency of leptin and its receptor in humans"; Japanese Journal of Clinical Medicine, vol. 68, extra issue 2, p. 486-490.

Kay; Fausto, "Liver regeneration: prospects for therapy based on new technologies", Molecular Medicine Today, Mar. 1997, pp. 108-115.

Kemp, W., "Safety and pharmacokinetics of DUR-928 in patients with non-alcoholic steatohepatitis—A Phase 1b study", Apr. 2017.

Kim, Mee J., "DUR-928, an endogenous regulatory molecule, exhibits anti-inflammatory and antifibrotic activity in a mouse model of NASH", Mar. 2017.

Landis et al., "Oxysterol Activators of Liver X Receptor and 9-cis-Retinoic Acid Promote Sequential Steps in the Synthesis and Secretion of Tumor Necrosis Factor-alpha from Human Monocytes", Journal of Biological Chemistry, Feb. 15, 2002, pp. 4713-4721, vol. 277, No. 7.

Lappano et al., "The Cholesterol Metabolite 25-Hydroxycholesterol Activates Estrogen Receptor a-Mediated Signaling in Cancer Cells and in Cardiomyocytes", PloS One, Jan. 31, 2011, pp. e16631-e16631, vol. 6, No. 1.

Lee YC. et al., Sp1 elements in SULT2B1b promoter and 5'-untranslate region of mRNA:Sp1/Sp2 induction and augmentation by histone deacetylase inhibition. FEBS Lett. 579:3639-3645, 2005.

Lee YC. et al., "Sp1 elements in SULT2B1b promoter and 5'-untranslated region of mRNA: Sp1/Sp2 induction and augmentation by histone deacetylase inhibition"; FEBS Lett. 579:3639-3645, 2005.

Lehmann et al., "Activation of the Nuclear Receptor LXR by Oxysterols Defines a New Hormone Response Pathway", The Journal of Biological Chemistry, Feb. 7, 1997, pp. 3137-3140, vol. 272, No. 6.

Li et al., "A Novel Metabolic Pathway for the Synthesis of the Newly Discovered Nuclear 5-cholesten-3beta, 25-diol 3-sulphate", Abstract.

Li et al., "Biosynthesis of the regulatory oxysterol, 5-cholesten-3[beta],25-diol 3-sulfate, in hepatocytes", Journal of Lipid Research, Sep. 21, 2007, pp. 2587-2596, vol. 48.

Lindsay, J; Wang; et al. et al., Structure, function and polymorphism of human cytosolic sulfotransferases Curr.Drug Metab 9:99-105, 2008.

Liu et al., "Nuclear Transport Modulation Reduces Hypercholesterolemia, Atherosclerosis, and Fatty Liver", Journal of the American Heart Association, Apr. 5, 2013, American Heart Association, Dallas, TX.

Lo Sasso et al., "Down-Regulation of the LXR Transcriptome Provides the Requisite Cholesterol Levels to Proliferating Hepatocytes", Hepatology, 2010, pp. 1334-1344, vol. 51.

Lo Sasso G, et al. (2010). Intestinal Specific LXR Activation Stimulates Reverse Cholesterol Transport and Protects from Atherosclerosis. Cell metabolism. 2010; 12(2), 187-193.

Lopez-Velazquez JA, et al., "Nuclear Receptors in Nonalcoholic Fatty Liver Disease"; Journal of Lipids. 2012.; 2012, Article ID 139875.

Lung EG. et al., Cdna cloning of mouse and human cholesterol 25-hydroxylases, polytopic membrane proteins that synthesize a potent oxysterol regulator of lipid metabolism. J. Bio. Chem. 273:34316-34327, 1998.

Luu W. et al., Osysterol: Old Tale, New Twils. AnnuRev. Pharmacol. Toxicol. 56:447-467, 2016.

Ma et al., "25-Hydroxycholesterol-3-sulfate regulates macrophage lipid metabolism via the LXR/SREBP-1 signaling pathway", Am J Physiol Endocrinol Metab, Oct. 14, 2008, pp. E1369-E1379, vol. 295.

Markus et al., Efficacy of Liver Transplantation in Patients with Primary Biliary Cirrhosis. N Engl J Med 1989; 320:1709-1713.

Mcclain, Craig J., "Which Therapeutic Targets Will Be the Most Attractive in the Future?", Oct. 2017.

Mcdonald; Russel, "25-Hydroxycholesterol: a new life in immunology", Journal of Leukocyte Biology, Dec. 2010, pp. 1071-1072, vol. 88, Society for Leukocyte Biology.

Grefhorst et al., "Stimulation of Lipogenesis by Pharmacological Activation of the Liver X Receptor Leads to Production of Large, Triglyceride-rich Very Low Density Lipoprotein Particles", Lipids and Lipoproteins, Sep. 13, 2002, pp. 34182-34190, vol. 277, No. 37.

Griffett K, et al, "A Liver-Selective LXR Inverse Agonist that Suppresses Hepatic Steatosis"; ACS Chemical Biology. 2013; 8(3):559-567.

He et al., "Identification and immunohistochemical localization of Sulfotransferase 2B1b (SULT2B1b) in human lung", Biochimica et Biophysica Acta, Apr. 12, 2005, pp. 119-126, vol. 1724, Elsevier.

He D. et al., "Inhibition of SULT2B1B expression alters effects of 3 beta-hydroxysteroids on cell proliferation and steroid hormone receptor in human LNCaP prostate cancer cells"; Prostate 67-1318-1329, 2007.

Higashi et al., "Expression of Cholesterol Sulfotransferase (SULT2B1b) in Human Skin and Primary Cultures of Human Epidermal Keralinocytes", The Journal of Investigative Dermatology, 2004, pp. 1207-1212, vol. 122, The Society for Investigative Dermatology.

Horton J, et al "SREBPs: activators of the complete program of cholesterol and fatty acid synthesis in the liver"; The Journal of Clinical Investigation. 2002; 109(9):1125-1131.

(56) References Cited

OTHER PUBLICATIONS

Horton J, et al. "Combined analysis of oligonucleotide microarray data from transgenic and knockout mice identifies direct SREBP target genes"; PNAS. 2003; 100(21): 12027-12032.

Hylemon et al., "Identification of a Novel Regulatory Nuclear Oxysterol", Abstract, 56rd Annual Meeting of the American Association for the Study of Liver Diseased, Nov. 11-15, 2005.

Ikegami et al, "Increased serum liver X receptor ligand oxysterols in patients with non-alcoholic fatty liver disease", J Gastroenterol, May 9, 2010, pp. 1257-1266, vol. 47, Springer.

Janout et al., "An Upside Down View of Cholesterol's Condensing Effect: Does Surface Occupancy Play a Role?", Langmuir, Apr. 20, 2010, pp. 5316-5318, vol. 26, No. 8.

Janowski et al., "An oxysterol signalling pathway mediated by the nuclear receptor LXR alpha"; Letters to Nature, Oct. 24, 1996, pp. 728-731, vol. 383.

Janowski et al., "Structural requirements of ligands for the oxysterol liver X receptors LXRα and LXRβ", Proc Natl Acad Sci U S A. Jan. 5, 1999;96(1):266-71.

Meloche; Falany, "Expression and characterization of the human 3[beta]-hydroxysteroid sulfotransferases (SULT2B1a and SULT2B1b)", Journal of Steroid Biochemistry & Molecular Biology, 2001, pp. 261-269, vol. 77, Elsevier.

Millatt et al., "Liver X receptors and the control of cholesterol homeostasis: potential therapeutic targets for the treatment of atherosclerosis", Biochimica Et Biophysica Actia, 2003, pp. 107-118, No. 1631.

Monsalve, et al. Peroxisome Proliferator-Activated Receptor Targets for the Treatment of Metabolic Diseases; Mediators of Inflammation. 2013.

Napodano, Jason et al., Zacks Small-Cap Research, Mar. 4, 2015, pp. (1-14).

Nelson et al., "The Oxysterol, 27-Hydroxycholesterol, Links Cholesterol Metabolism to Bone Homeostasis Through Its Actions on the Estrogen and Liver X Receptors", Endocrinology, Sep. 20, 2011, pp. 1-15, vol. 152, No. 12, The Endocrine Society.

Ning, Yanxia, "Cholesterol metabolites alleviate injured liver function and decrease mortality in an LPS-induced mouse model", Metabolism Clinical and Experimental, 71 (2017), 83-93.

Ogawa et al., "A facile synthesis of C-24 and C-25 oxysterols by in situ generated ethyl(trifluoromethyl)dioxirane", Steroids, 2009, pp. 81-87, vol. 74, Elsevier.

Okamura et al., "Studies on vitamin D and its analogs. VIII. 3-deoxy-1α,25-dihydroxyvitamin D3, a potent new analog of 1α,25-(OH)2-D3", Biochemical and Biophysical Research Communications, 1975, pp. 24-30, vol. 65, No. 1, Academic Press, Inc.

Okamura et al., "Studies on Vitamin D (Calciferol) and Its Analogues. 13. 3-Deoxy-3[alpha]-methyl-1[alpha]-hydroxyvitamin D3, 3-Deoxy-3[alpha]-methyl-1 [alpha],25-dihydroxyvitamin D3, and 1 [alpha]-Hydroxy-3-epivitamin Dr. Analogues with Conformationally Biased A Rings", Journal of Organic Chemistry, 1978, pp. 574-580, vol. 43, No. 4, American Chemical Society.

Pandak, et al., "Regulation of Oxysterol 7[alpha]-Hydroxylase (CYP7B1) in Primary Cultures of Rat Hepatocytes", Hepatology, 2002, pp. 1400-1408, vol. 35, No. 6, American Association for the Study of Liver Diseases.

Pandak, et al., "Transport of Cholesterol into Mitochondria Is Rate-limiting for Bile Acid Synthesis via the Alternative Pathway in Primary Rat Hepatocytes", The Journal of Biological Chemistry, Oct. 3, 2002, pp. 48158-48164, vol. 277, No. 50.

Peet et al., "Cholesterol and Bile Acid Metabolism Are Impaired in Mice Lacking the Nuclear Oxysterol Receptor LXR[alpha]", Cell, May 29, 1998, pp. 693-704, vol. 93, Cell Press.

Peet et al., "The LXRs: a new class of oxysterol receptors", Current Opinions in Genetics and Development, 1998, pp. 571-575, vol. 8.

Pezacki et al. "Transcriptional profiling of the effects of 25-hydroxycholesterol on human hepatocyte metabolism and the antiviral state ii conveys against the hepatitis C virus", BMC Chemical Biology, Jan. 16, 2009, vol. 9, No. 2, BioMed Central Lid.

Picard et al. (2012) "Mitochondrial dysfunction and lipid accumulation in the human diaphragm during mechanical ventilation"; Am J Resp Critical Care Med 186:1140.

Polyzos, et al. "Sulfated oxysterols as candidates for the treatment of nonalcoholic fatty liver disease", Metabolism, 2012, pp. 755-758, vol. 61, Elsevier.

Quintero P. Arrese M. (2013) "Nuclear Control of Inflammation and Fibrosis in Nonalcoholic Steatohepatitis: Therapeutic Potential of Dual Peroxisome Proliferator—Activated Receptor Alpha/Delta Agonism"; Hepatology 58(6), pp. 1881-1884.

Reboldi A. et al., Inflammation 25-Hydraxycholesterol suppresses interleukin-1-driven inflammation downstream of type I interferon Science 345:679-684, 2014.

Ren et al., "25-hydroxycholesterol and 25-hydroxycholesterol 3-sulfate reciprocally regulate lipid metabolism and inflammation in hepatocytes and macrophages", Abstract, The Liver Meeting, the 60th Annual Meeting of the American Association for the Study of Liver Diseases, Oct. 30-Nov. 3, 2009.

Ren et al., "25-Hydroxycholesterol sulfation regulates lipid metabolism in vivo in mice", Abstract.

Ren et al., "Discovery of a Novel Oxysterol, 5-Cholesten-3beta, 25-Diol 3-Sulfonate, in Nuclei and Mitochondria Following Overexpression of the Gene Encoding StarD1 ", Bile Acids:Biological Actions and Clinical Relevance, 2007 pp. 20-35, Kluwer Academic Publishers.

Ren et al., "Discovery of a Novel Oxysterol, 5-Cholesten-3beta, 25-Diol 3-Sulfonate, in Nuclei and Mitochondria Following Overexpression of the Gene Encoding StarD1", Abstract, International Bile Acid Meeting, XIII Falk Liver Week, Falk Symposia 155, Oct. 6-11, 2006.

Ren et al., "Discovery of a Novel Regulatory Pathway for Maintenance of Intracellular Cholesterol Homeostasis", Abstract, Dow Annual Meeting 2007, May 19-25, 2007.

Ren et al., "Identification of Novel Regulatory Cholesterol Metabolite, 5-Cholesten, 3-Beta, 25-Diol, Disulfate" PLOS One, Jul. 2014, vol. 9. No. 7, p. 1-11.

Ren et al. "Identification of a novel sulfonated oxysterol, 5-cholesten-3[beta],25-diol 3-sulfonate, in hepatocyte nuclei and mitochondria", Journal of Lipid Research, Feb. 27, 2006, pp. 1081-1090, vol. 47, American Society for Biochemistry and Molecular Biology, Inc.

Ren, Shunlin, "Novel Oxysterol Sulfates Alleviate Injured Liver Function and Decrease Mortality in Mouse Models", Nov. 2017.

Ren et al., "Overexpression of Cholesterol Transporter SIAR Increases in Vivo Rates of Bile Acid Synthesis in the Rat and Mouse", Liver Biology and Pathobiology, Aug. 20, 2004, pp. 910-917, vol. 40, No. 4.

Ren et al., "Regulation of Hepatocyte Lipid Metabolism by 25-Hydroxycholesterol-3-Sulfate (25HC3S) Is Mediated Via the LXR/SREBP-1 Signaling Pathway", Abstract, Dow Annual Meeting 2008, May 17-23, 2008.

Ren et al., "Sulfated oxysterol, 25HC3S, is a potent regulator of lipid metabolism in human hepatocytes", Biochemical and Biophysical Research Communications, Jul. 6, 2007, pp. 802-808, vol. 360, Elsevier.

Ren et al., "Sulfation of 25-hydroxycholesterol regulates lipid metabolism, inflammatory responses, and cell proliferation", Am J Physiol Endocrinol Metab, Dec. 3, 2013, pp. E123-E130, vol. 306.

Ren S., et al., "Sulfated oxysterol, 25HC3S, is a potent regulator of lipid metabolism in human hepatocytes", ScienceDirect, BBRC, 360 (2007) pp. 802-808.

Ruan X, et al., PPARs and the kidney in metabolic syndrome, AJP-Renal Physiol, vol. 294, Jan. 30, 2008.

Shi et al., "Cholesterol Sulfate and Cholesterol Sulfotransferase Inhibit Gluconeogenesis by Targeting Hepatocyte Nuclear Factor 4a", Molecular and Cellular Biology, Feb. 1, 2014, vol. 34, No. 3, p. 485-497.

Shimizu et al., "Conservation of the Hydroxysteroid Sulfotransferase SULT2B1 Gene Structure in the Mouse: Pre- and Postnatal Expression, Kinetic Analysis of Isoforms, and Comparison with Prototypical SULT2A1"; Endocrinology, Apr. 2003, pp. 1186-1193, vol. 144, No. 4, The Endocrine Society.

(56) References Cited

OTHER PUBLICATIONS

Song et al. "Auto-oxidized cholesterol sulfates are antagonistic ligands of liver X receptors: implications for the development and treatment of atherosclerosis". Steroids. 2001. pp. 473-479, vol. 66, Elsevier.
Strott; Higashi, "Cholesterol sulfate in human physiology: what's it all about?", Journal of Lipid Research, 2003, pp. 1268-1278, vol. 44.
Su et al., "Hypercholesterolemia in Primary Biliary Cirrhosis"; N Eng J Med 357;15:1561-1562.
Treuter, "New wrestling rules of anti-inflammatory transrepression by oxysterol receptor LXR revealed", Cell Research, 2011, pp. 711-714, vol. 21.
Trousson et al., "25-hydroxycholesterol provokes oligodendrocyte cell line apoptosis and stimulates the secreted phospholipase A2 type IIA via LXR beta and PXR"; Journal of Neurochemistry, 2009, pp. 945-958, vol. 109.
Wagner BL, et al. "Promoter-Specific Roles for Liver X Receptor/Corepressor Complexes in the Regulation of ABCA1 and SREBP-1 Gene Expression"; Mal. Cell. Biol. 2003; 23(16):5780.
Weinberg (2006) "Lipotoxicity"; Kidney International 70:1560.
Wojcicka et al., "Liver X receptors (LXRs). Part I: Structure, function, regulation of activity, and role in lipid metabolism", Postepy Hig Med Dosw., Dec. 3, 2007, pp. 736-759, vol. 61.
Xu et al., "25-Hydroxycholesterol (25HC) and 25HC-3-Sulfate (25HC3S) Mediate Nuclear Orphan Receptors in Opposite Direction in Hepatocytes", Abstract, XX International Bile Acid Meeting, Falk Symposia 165, Jun. 13-14, 2008.
Xu et al., "25-Hydroxycholesterol-3-sulfate (25HC3S) Attenuates Hepatocyte Intracellular Lipid Levels and Inflammatory Response via LXR/SREBPs and 1[kappa]B[alpha]/NF-[kappa]B Pathways", Abstract, Dow Annual Meeting 2008, May 3, 2010.
Xu et al., "25-Hydroxycholesterol-3-sulfate attenuates inflammatory response via PPAR [gamma]signaling in human THP-1 macrophages", Am J Physiol Endocrinol Metab, Jan. 24, 2012, pp. E788-E799, vol. 302.
Xu et al.., "25-Hydroxycholesterol-3-Sulfate Decreases Hepatic Steatosis and Inflammation in Mouse Models of Nonalcoholic Fatty Liver Disease by Down-Regulating Sterol Regulatory Element Binding Protein-1c", Abstract, Dow Annual Meeting 2011, May 7-10, 2011.
Xu et al., "Induction of 1[kappa]B [alpha] Expression as a Mechanism Contributing to the Anti-inflammatory Response by 25-Hydroxycholesterol-3-Sulfate (25HC3S) in Primary Rat Hepatocytes and THP-1 Macrophages", Abstract, Dow Annual Meeting 2011, May 7-10, 2011.
Xu et al., "Regulation of Hepatocyte Lipid Metabolism and Inflammatory Response by 25-Hydroxycholesterol and 25-Hydroxycholesterol-3-sulfate", Lipids, 2010, pp. 821-832, vol. 45, AOCS.
Xu et al. "Reversal of Diet-induced Serum and Hepatic Lipid Accumulation by 5-cholesten-3beta.25-diol 3-sulfate in Mouse Models of Nonalcoholic Fatty Liver Diseases". Hepatology, Jun. 9, 2011.
Xu et al., "5-Cholesten3[beta],25-Diol 3-Sulfate Decreases Lipid Accumulation in Diet-Induced Nonalcoholic Fatty Liver Disease Mouse Model", Molecular Pharmacology, Mar. 2013, 648-658, vol. 83.
Zager et al. (2011) "Acute unilateral ischemic renal injury induces progressive renal inflammation, lipid accumulation, histone modification, and "end-stage" kidney disease."; Am J Physiol Renal Physiol 30:F1334.
Zelcer N and Tontonoz P. "Liver X receptors as integrators of metabolic and inflammatory signaling"; J Clin Invest. 2006; 116(3):607-614.
Zhang et al., "Cholesterol metabolite, 5-cholesten-3[bela]-25-diol-3-sulfate, promotes hepatic proliferation in mice", Journal of Steroid Biochemistry and Molecular Biology, 2012, pp. 262-270, vol. 132, Elsevier.
Zhang et al., "Cytosolic sulfotransferase 2B1b promotes hepatocyte proliferation gene expression in vivo and in vitro", Am J Physiol Gastrointest Liver Physiol, Jun. 7, 2012, pp. G344-G355, vol. 303.
Zhang et al., "Effects of 25-hydroxycholesterol sulfation on liver regeneration in normal and partial hepatectomy (PHX) mouse models.", Abstract, DOW Annual Meeting 2011, May 7-10, 2011.
Zhang et al., "SULT2B1b overexpression promotes liver regeneration via inhibiting LXR signaling pathway in mouse with or without Partial Hepatectomy", Poster.
Zhang Hengai et al., "Advances in the research on drugs for the prevention and treatment of renal diseases with PPAR as target site", China Pharmaceutical Journal, vol. 45, No. 7, Apr. 30, 2010.
Zitvogel et al. (2010) "Decoding cell death signals in inflammation and immunity"; Cell 140(6); pp. 798-804.
Zuercher et al., "Discovery of Tertiary Sulfonamides as Potent Liver X Receptor Antagonists", J. Med. Chem., 2010, pp. 3412-3416, vol. 53, No. 8, American Chemical Society.
U.S. Appl. No. 16/320,079, filed Jan. 23, 2019, Ren, et al.
U.S. Appl. No. 16/320,074, filed Jan. 23, 2019, Ren, et al.
U.S. Appl. No. 16/320,400, filed Jan. 24, 2019, Ren, et al.
U.S. Appl. No. 16/368,553, filed Mar. 28, 2019, Ren, et al.
U.S. Appl. No. 16/430,895, filed Jun. 4, 2019, S. Ren.
U.S. Appl. No. 16/593,460, filed Oct. 4, 2019, Ren, et al.
U.S. Appl. No. 16/599,044, filed Oct. 10, 2019, S. Ren.
Blaton, "Dyslipidemia at chronic renal failure," International Federation of Clinical Chemistry and Laboratory Medicine, 2009, vol. 20, No. 1, pp. 59-60 Ejifcc 20/01 http://www.ifec.crg.
Cases et al. (2005) "Dyslipidemia and the progression of renal disease in chronic renal failure patients"; Kidney International vol. 68, supplement 99, pp. s87-s93.
Considine et al., "Serum immunoreactive-leptin concentration in normal-weight and obese humans," The New England Journal of Medicine, 1996, vol. 334, No. 5, pp. 292-295.
DePass, et al; "In Vivo Tissue Distribution and Elimination of DUR-928, a First in ClassTherapeutic for Treatment of Hepatic and Renal Disease"; Abstract #3355/Poster Board #P137, Late Breaking SOT Poster, Toxicokinetics, 57thAnnual Meeting of the Society of Toxicology, San Antonio, Texas, Mar. 11-15, 2018.
DePass, et al; "A 14-Day Intravenous Infusion Toxicity and ToxicokineticStudy of DUR-928, a Novel, First in Class, Investigational Therapeutic in Sprague-DawleyRats"; American College of Toxicology's 39th Annual Meeting, West Palm Beach, Florida, Nov. 4-7, 2018.
Durect, (2018) "A Research Study to Assess the Safety, Pharmacokinetics and Pharmacodynamics of DUR-928 in Patients With Alcoholic Hepatitis (AH)"; U.S. National Library of Medicine, ClinicalTrials.gov Identifier: NCT03432260; 14 pages.
Durect (2018) "A Research Study to Evaluate Safety and Efficacy of DUR-928 in Subjects With Primary Sclerosing Cholangitis (PSC)"; U.S. National Library of Medicine, ClinicalTrials.gov Identifier: NCT03394781; 13 pages.
Feng et al., "The role of leptin in obesity and the potential for leptin replacement therapy" Endocrine, 2013, vol. 44, pp. 33-39 (Year: 2013).
Gross et al., Quality of Life Before and After Liver Transplantation for Cholestatic Liver Disease. H Epatology 1999;29:356-364 (Year: 1999).
Itoh, et al (1999) "Synthesis of 6- and 7-hydroxyestradiol 17-sulfates: The potential metabolites of estradiol 17-sulfate by female rat liver microsomes"; Steroids 64; pp. 363-370.
Jones et al., (1997) "Hepatocellular Carcinoma in Primary Biliary Cirrhosis and its impact on outcomes. Hepatology"; 26:1138-1142.
Kawata et al., "Effect of pravastatin on survival in patients with advanced hepatocellular carcinoma. A randomized controlled trial"; British Journal of Cancer (2001) 84(7), 886-891 (Year:2001).
Khan and Glenton (2008) "Calcium oxalate crystal deposition in kidneys of hypercalciuric mice with disrupted type IIa sodium-phosphate cotransporter"; Am J Physiol Renal Physiol. 294(5):F1109-15.
Kim MJ, et al; "Attenuation of Renal Ischemic Reperfusion Injury in Rats with DUR-928, a Novel, First-in-Class Therapeutic in Development for Renal Disease"; Poster #: SA-PO650, Kidney Week, San Diego, CA—Oct. 23-28, 2018.
Li et al. (1999) "Sterol synthesis. Preparation and characterization of fluorinated and deuterated analogs of oxygenated derivatives of cholesterol"; Chemistry and Physics of Lipids 99; pp. 33-71.

(56) References Cited

OTHER PUBLICATIONS

Perez et al., Bile-acid-induced cell injury and protection. World J Gastroenterol Apr. 14, 2009; 15(14): 1677-1689 (Year: 2009).
Shah, et al; "A Clinical Drug-Drug Interaction Study with Midazolam to Assess the Effect of DUR-928 on CYP3A4"; Meeting of the American College of Clinical Pharmacology, Bethesda, Maryland, Sep. 23-25, 2018; 1 page.
Shah, et al; "Safety and Single Ascending Dose Pharmacokinetic Study of DUR-928 in Patients with Chronic Kidney Disease versus Matched Control Subjects"; Poster #: SA-PO63; Kidney Week, San Diego, CA—Oct. 23-28, 2018; 1 page.
Shah, et al; "Pharmacokinetic and Pharmacodynamic Response in Individual NASH Patients Receiving Two Dose Levels of DUR-928"; NASH Summit—2019, Apr. 22-25, 2019. 1 page.
Shepherd et al. (2007) "Effective of intensive lipid lowering with atorvastatin on renal function in patients with coronary heart disease: the treatment of new targets study," Clin. J. Am. Soc. Nephrol. vol. 2, pp. 1131-1139.
Taddei et al., "High incidence of cholesterol gallstone disease in type 1 Gaucher disease: characterizing the biliary phenotype of type 1 Gaucher disease"; J. Inherit Metab Dis. 2010, vol. 33, pp. 291-300.
Tan et al., "Leptin Deficiency contributes to the pathogenesis of alcoholic fatty liver disease in mice" The American Journal of Pathology, 2012, vol. 181, No. 10, pp. 1279-1286 (Year: 2012).
Thakar et al., "Acute kidney injury episodes and chronic kidney disease risk in diabetes mellitus," Clin. J. Am. Soc. Nephrol. 2011, vol. 6, pp. 2567-2572. (Year: 2011).
Therapeutics, Inc. (2019) "Safety and Efficacy Study of DUR-928 Topical Solution in Subjects With Plaque Psoriasis"; U.S. National Library of Medicine, ClinicalTrials.gov Identifier: NCT03837743; 14 pages.
Teh et al., Hepatic Resection of Hepatocellular Carcinoma in Patients with Cirrhosis: Model of End-Stage Liver Disease 9MELD) Score Predicts Perioperative Mortality. Journal of Gastrointestinal Surgery. vol. 9, No. 9, 200-5, pp. 1207-1215 (Year:2005).
Zhang et al., "Effects of 25-Hydroxycholesterol Sulfation on Liver Regeneration in Normal and Partial Hepatectomy (PHX) Mouse Models"; (May 2011) Gastroenterology vol. 140, Issue 5, Supplement 1, p. S-967.
Bai, et al "Overexpression of Oxysterol Sulfotransferase (Sult2B1 b) Decreases Intracellular Lipid Levels via SREBPs Signaling Pathway in Primary Human Aorta Endothelial Cells"; Abstract, Arteriosclerosis, Thrombosis, and Vascular Biology 2010 Scientific Sessions, American Heart Association; Apr. 8-10, 2010.
Kanjanabuch T, et al (2007) "PPAR-γ agonist protects podocytes from injury"; Kidney Int. 71(12); pp. 1232-1239.
Pandak, et al., "The cholesterol metabolite, 5-cholesten-3beta, 25-diol 3-sulfate, promotes hepatic proliferation in mice"; Poster Abstract, XXII International Bile Acid Meeting: Hepatic and Extrahepatic Targets of Bile Acid Signalling, Falk Symposium 184; Sep. 14-15, 2012.
Pandak, et al., "Reversal of NAFLD through selective increased intracellular hepatic cholesterol catabolism"; Poster Abstract, XXIII International Bile Acid Meeting: Bile Acids as Signal Integrators and Metabolic Modulators, Falk Symposium 194; Oct. 8-9, 2014.
Ren et al., "25-Hydroxycholesterol-3-sulfate (25HC3S) regulates lipid metabolism by activation/inactivation of receptors in hepatocytes and macrophages", Abstract, XX International Bile Acid Meeting, Falk Symposium 165; Jun. 13-14, 2008.
Ren, et al "25-Hydroxycholesterol-3-Sulfate Activates PPARgamma and Attenuates Inflammatory Responses in Human Macrophages"; Poster Abstract, Arteriosclerosis, Thrombosis, and Vascular Biology Annual Conference 2009, American Heart Association; Apr. 29-May 1, 2009.
Ren S., et al; "The acidic pathway of bile acid biosynthesis: Role in oxysterol sulfation, lipid metabolism and inflammatory responses"; Poster Abstract, XXII International Bile Acid Meeting, Falk Symposia 184; Sep. 14-15, 2012.
Ren, et al; "Oxysterol sulfates alleviate injured liver function and decrease mortality in mouse models"; Poster Abstract, XXV International Bile Acid Meeting:Bile Acids in Health and Disease, Symposium 211; Jul. 6-7, 2018.
Wang, et al (2020) "High Glucose Induces Lipid Accumulation via 25-Hydroxycholesterol DNA-CpG Methylation"; iScience 23(5); pp. 1-28.
Xu et al., "25-Hydroxycholesterol-3-Sulfate (25HC3S) Suppresses NF-κB Activatioand Inflammatory Response in Human Macrophages and Hepatocytes", Abstract, Arteriosclerosis, Thrombosis, and Vascular Biology 2010 Scientific Sessions, American Heart Association; Apr. 8-10, 2010.
Xu et al., "Induction of IKBa Expression Mediates the Anti-Inflammatory Response to 25Hydroxycholesterol-3-Sulfate (25HC3S) in Primary Rat Hepatocytes and THP-1 Macrophages"; AASLD Abstract; 2011.
Zuo, et al (2012) "Protective effects of PPARγ agonist in acute nephrotic syndrome"; Nephrol Dial Transplant. 27(1); pp. 174-181.

(M.W. 482)
5-cholesten-3β, 25-diol 3-sulphate

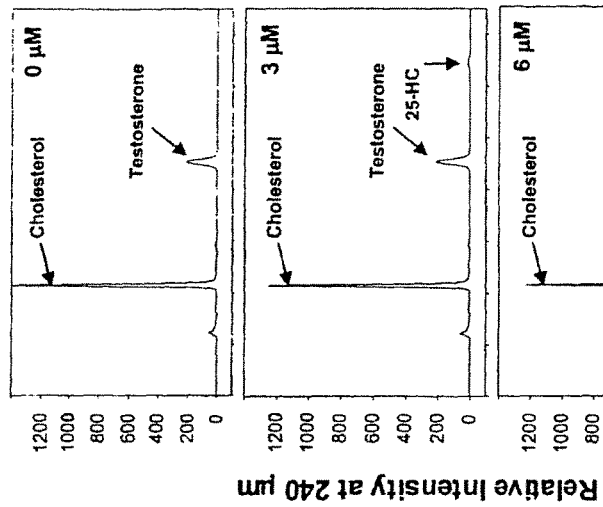
Figure 14E
Figure 14F
Figure 14G
Figure 14H
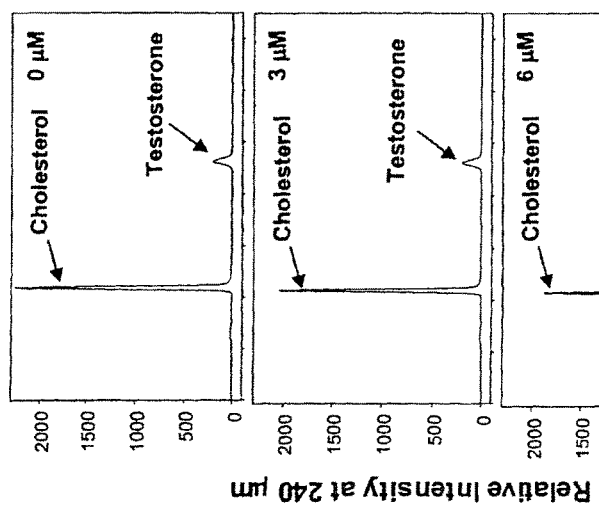
Figure 14A
Figure 14B
Figure 14C
Figure 14D

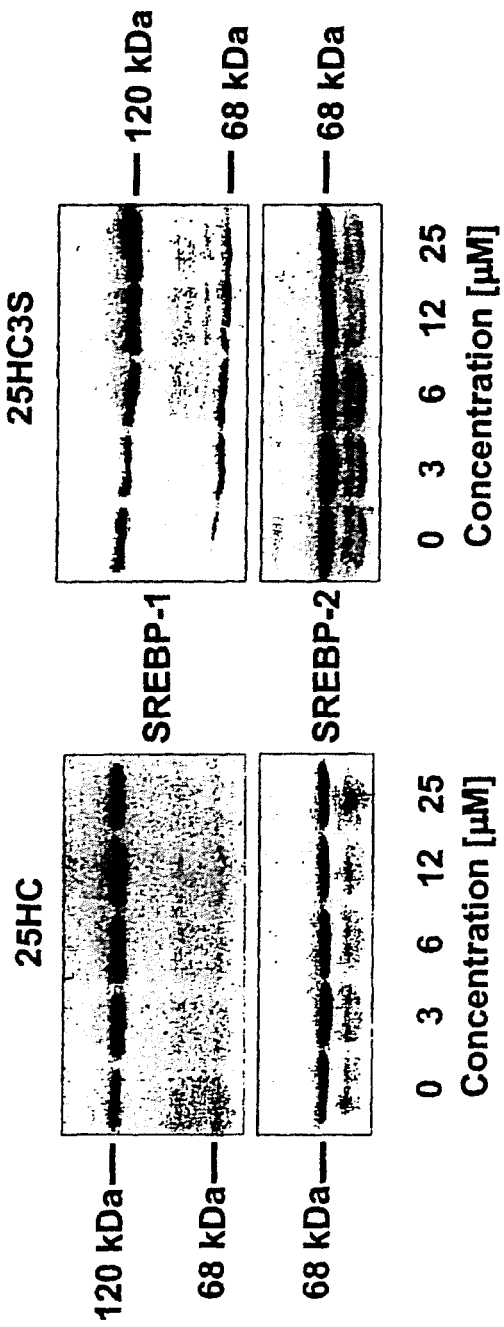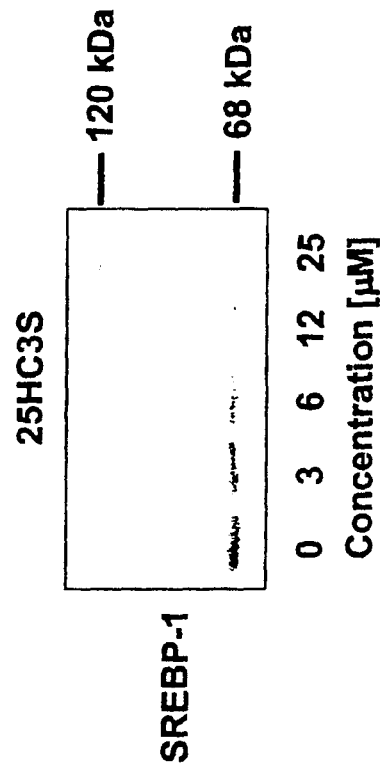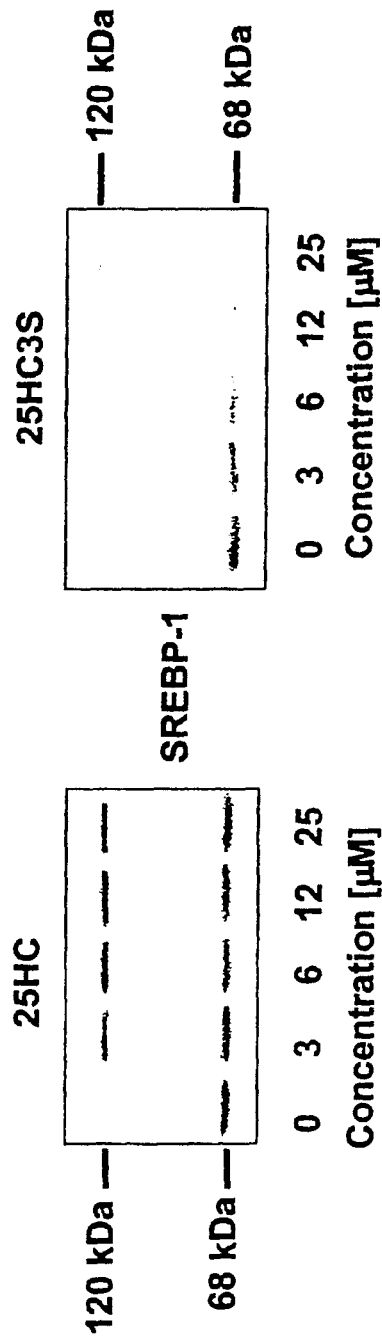

NUCLEAR SULFATED OXYSTEROL, POTENT REGULATOR OF LIPID HOMEOSTASIS, FOR THERAPY OF HYPERCHOLESTEROLEMIA, HYPERTRIGLYCERIDES, FATTY LIVER DISEASES, AND ATHEROSCLEROSIS

CROSS REFERENCE TO RELATED APPLICATIONS

This application is a continuation of U.S. patent application Ser. No. 15/042,244, filed Feb. 12, 2016, now U.S. Pat. No. 10,144,759, which application is continuation of U.S. patent application Ser. No. 13/766,839, filed Feb. 14, 2013, now U.S. Pat. No. 9,321,802, which application is a continuation of U.S. patent application Ser. No. 12/708,803, filed Feb. 19, 2010, now U.S. Pat. No. 8,399,441, which application is a continuation-in-part (CIP) of U.S. patent application Ser. No. 11/739,330, filed Apr. 24, 2007, and claims benefit of U.S. provisional patent application Ser. No. 61/154,063, filed Feb. 20, 2009. U.S. application Ser. No. No. 11/739,330 is a national stage CIP claiming benefit of International patent application PCT/US2005/033874, filed on Sep. 21, 2005, which in turn claims benefit of U.S. Provisional Application 60/621,537, filed on Oct. 25, 2004. The complete contents of each of these applications are herein incorporated by reference.

STATEMENT OF FEDERALLY SPONSORED RESEARCH AND DEVELOPMENT

This invention was made, in part, with government support under Grant Nos. R01 HL078898 and P01 DK038030 awarded by the National Institutes of Health (NIH). The government has certain rights in the invention.

BACKGROUND OF THE INVENTION

Field of the Invention

The invention generally relates to lipid-lowering therapies. In particular, the invention provides a nuclear cholesterol metabolite, 5-cholesten-3β, 25-diol 3-sulphate, that decreases lipid biosynthesis and increases cholesterol secretion and degradation, and is thus useful for the treatment and prevention of hypercholesterolemia, hypertriglyceridemia, atherosclerosis, and conditions related to fat-accumulation and inflammation (e.g. nonalcoholic fatty liver disease, NAFLD, and atherosclerosis).

Background of the Invention

Cholesterol is used by the body for the manufacture and repair of cell membranes, and the synthesis of steroid hormones and vitamin D, and is transformed to bile acids in the liver. There are both exogenous and endogenous sources of cholesterol. The average American consumes about 450 mg of cholesterol each day and produces an additional 500 to 1,000 mg in the liver and other tissues. Another source is the 500 to 1,000 mg of biliary cholesterol that is secreted into the intestine daily; about 50 percent is reabsorbed (enterohepatic circulation).

High serum lipid levels (hypercholesterolemia and hypertriglyceridemia) are associated with the accumulation of cholesterol in arterial walls, and can result in NAFLD and atherosclerosis. The plaques that characterize atherosclerosis inhibit blood flow and promote clot formation, and can ultimately cause death or severe disability via heart attacks and/or stroke. A number of therapeutic agents for the treatment of hyperlipidemia have been developed and are widely prescribed by physicians. Unfortunately, only about 35% of patients are responsive to the currently available therapies.

Nonalcoholic fatty liver disease (NAFLD) is the most common liver disease in the United States. This condition is associated with obesity, type-II adult onset diabetes, sedentary lifestyle, and diets high in fat. The earlier stage of NAFLD, fatty liver, is potentially reversible when proper treatment steps are taken. However, left unchecked, it can progress to inflammation of liver cells (nonalcoholic steatohepatitis, or NASH) which is much more difficult to treat. Without treatment, NASH can result in irreversible scarring of liver tissue (steatonecrosis), with the potential to cause cirrhosis, liver failure, and liver cancer.

There is an ongoing need to develop agents and methodologies to decrease intracellular and serum lipid levels, and to prevent or treat disease conditions involving the inflammation caused by elevated lipid levels.

SUMMARY OF THE INVENTION

The present invention provides a novel sulfated oxysterol, 5-cholesten-3β, 25-diol 3-sulphate, with potent serum lipid lowering properties. 5-Cholesten-3β, 25-diol 3-sulphate is a nuclear sterol metabolite that decreases lipid biosynthesis and increases cholesterol secretion and degradation (bile acid synthesis). The increase in cholesterol degradation and decrease in lipid synthesis can lead to lower levels of intracellular and serum lipid levels. Thus, the sulfated oxysterol is useful for preventing or treating diseases associated with elevated lipid levels, such as hypercholesterolemia, hypertriglyceridemia, gallstones, cholestatic liver disease, atherosclerosis, NAFLD, NASH, etc.

It is an object of this invention to provide a substantially purified 5-cholesten-3β, 25-diol 3-sulphate having the following chemical formula:

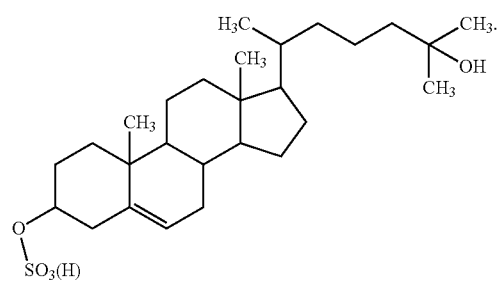

It is a further object of the invention to provide a lipid-lowering composition. The composition comprises 5-cholesten-3β, 25-diol 3-sulphate, and a pharmaceutically acceptable carrier.

It is a further object of the invention to provide a method for lowering serum lipids levels (such as cholesterol and triglyceride levels) in a patient in need thereof. The method comprises the step of administering 5-cholesten-3β, 25-diol 3-sulphate to the patient in an amount sufficient to lower serum lipid levels, e.g. cholesterol and triglyceride levels, in the patient.

The invention further provides a method to treat or prevent pathological conditions associated with high serum lipids (e.g. cholesterol and triglyceride) levels in a patient in need thereof The method comprises the step of administering 5-cholesten-3β, 25-diol 3-sulphate to the patient in an amount sufficient to lower serum lipid levels in the patient, and to prevent or treat the pathological condition. The pathological condition is, for example, hypercholesterolemia, hypertriglyceridemia, atherosclerosis, or NAFLD.

The invention further provides a method of preventing or treating inflammation caused by or associated with lipid accumulation, or conditions or diseases associated with lipid accumulated-inflammation in a patient in need thereof The method comprises the step of administering 5-cholesten-3β, 25-diol 3-sulphate to the patient in an amount sufficient to prevent or treat the inflammation or the condition associated with inflammation in the patient. In one embodiment, the conditions associated with inflammation are non-alcoholic fat liver diseases and atherosclerosis.

The invention also provides a method of decreasing lipid synthesis in a patient in need thereof The method comprises the step of administering 5-cholesten-3β, 25-diol 3-sulphate to the patient in an amount sufficient to decrease lipid synthesis in the patient.

The invention further provides a method of increasing cholesterol secretion or degradation in cells. The method comprises the step of increasing a level of 5-cholesten-3β, 25-diol 3-sulphate in the cells. The method may be carried out by exposing the cells to 5-cholesten-3β, 25-diol 3-sulphate.

BRIEF DESCRIPTION OF THE DRAWINGS

FIG. 4A, Nuclear inner membrane (Fraction E). FIG. 4B, Nuclear digests (Fraction F).

FIG. 5A, nuclear extracts (Fraction D) 195 nm profiles: control; FIG. 5B, nuclear extracts (Fraction D) 195 nm profiles: StarD1; FIG. 5C, nuclear extracts (Fraction D) 195 nm profiles: CYP7A1; FIG. 5D, nuclear extracts (Fraction D) $^{14}$C profiles: control; FIG. 5E, nuclear extracts (Fraction D) $^{14}$C profiles: StarD1; FIG. 5F, nuclear extracts (Fraction D) 195 nm profiles: CYP7A; FIG. 5G, non-nuclear extracts (Fraction A) $^{14}$C profiles: control; FIG. 5H, non-nuclear extracts (Fraction A) $^{14}$C profiles: StarD1; FIG. 5I, non-nuclear extracts (Fraction A)$^{14}$C profiles: CYP7A. In each case, nuclear methanol/water extracts of the equivalent of 5×10$^6$ cells were loaded.

FIGS. 6A-6C, 195 nm profiles. FIGS. 6D-6A-6F, radioactivity profiles.

FIG. 7A, HPLC elution profile of the sulfatase digestion products. FIG. 7B, HPLC elution profile of [$^{14}$C]27-hydroxycholesterol. FIG. 7C, HPLC elution profile of [$^{14}$C]25-hydroxycholesterol . FIG. 7D, products from the chloroform phase were further analyzed by TLC using a mixture of toluene:ethyl acetate (2:3) as developing solvent. 27-C represents 27-hydroxycholesterol; P, sulfatase digestion products of the purified nuclear oxysterols; 25-C, 25-hydroxycholesterol.

(FIG. 8A) A selected ion chromatogram of mass ion at m/z 481; (FIG. 8B) the Q1 full scan spectrum; (FIG. 8C) product scan spectrum of m/z 481. The amu represents atomic mass units, and cps, counts per second.

(FIG. 12A) addition of sulfate group onto 3β-position of 25-hydroxycholesterol for the synthesis of the novel nuclear oxysterol by incubation with sulfur trioxide triethyl amine complex; (FIG. 12B) mass spectrophometric analysis of the product after incubation with the sulfur trioxide and purified by HPLC. Mass ion, m/z 481, represents 25-hydroxycholesterol (M.W. 482)+Sulfate group (M.W. 80); (FIG. 12C) nuclear magnetic resonance (NMR) analysis of the 25-hydroxycholesterol 3-sulfate as starting material for the synthesis. The chemical shift of the proton at C3 in the molecule can be seen at 3.35 ppm; and (FIG. 12D) NMR analysis of the product shows the proton at C3 in the molecule has been shifted to 4.12 ppm from 3.35 ppm in its original compound.

FIG. 13A. TLC analysis of the [$^{14}$C]-acetate derivatives: the chloroform phase extracts of the equivalent of 5×10$^6$ cells were loaded onto each lane, separated by developing system of tuluene:acetyl acetate, and visualized by Imagine Reader. FIG. 13B. HPLC analysis of the [$^{14}$C]-acetate derivatives: the chloroform phase extracts of the equivalent of 5×10$^6$ cells were loaded onto silica gel column. The effluents were collected, 0.5 min/fraction. The radioactivities in each fraction were determined by Scintillation Counting. FIG. 13C. A summary of three experiments of HPLC analysis. Each bar represents the mean of three experiments±standard deviation.

FIGS. 14A-14H. HPLC analysis of cholesterol levels in microsomal fractions. The total lipids were extracted from 25HC3 S-treated (left panels) or 25HC-(right panels) treated HepG2 cells. α,β-Unsaturated ketones were generated by incubating the extracted sterols with cholesterol oxidase and were analyzed by normal phase HPLC: FIGS. 14A-C: the lipids from the cells treated with 0, 3, and 6 μM of 25HC3S; FIG. 14D. A summary of a series experiments, the lipids from the cells treated with 0, 3, 6, 12, and 25 μM of 25HC3S. FIGS. 14E-G: the lipids from the cells treated with 0, 3, and 6 μM of 25HC; FIG. 14H. A summary of a series experiments, the lipids from the cells treated with 0, 3, 6, 12, and 25 μM of 25HC. The data represent a typical result from one of three independent experiments.

FIGS. 17A-17E: the lipids from the cells treated with 0, 3, 6, 12, 25 μM of 25HC as indicated; The data represent a typical result from two independent experiments.

FIGS. 18A-18D. Western blot analysis of SREBPs activation following 25HC3S or 25HC treatment in HepG2 cells. Total proteins were extracted from HepG2 cells treated with 25HC in ethanol (0.1%) (FIGS. 18A and 18C) or 25HC3S in DMSO (0.1%) (FIGS. 18B and 18D), cultured in the media in absence (FIGS. 18A and 18B) or presence (FIGS. 18C and 18D) of mevinolin (50 mM) and mevalonate (0.5 mM). SREBP-1 and SREBP-2 protein levels in the cells were determined by Western blot analysis. The extracted protein (100 μg) was loaded onto each lane for each condition as indicated. The data represent a typical result from one of three independent experiments. The trends of the protein levels are highly reproducible.

DETAILED DESCRIPTION OF THE PREFERRED EMBODIMENTS OF THE INVENTION

Figure 1:
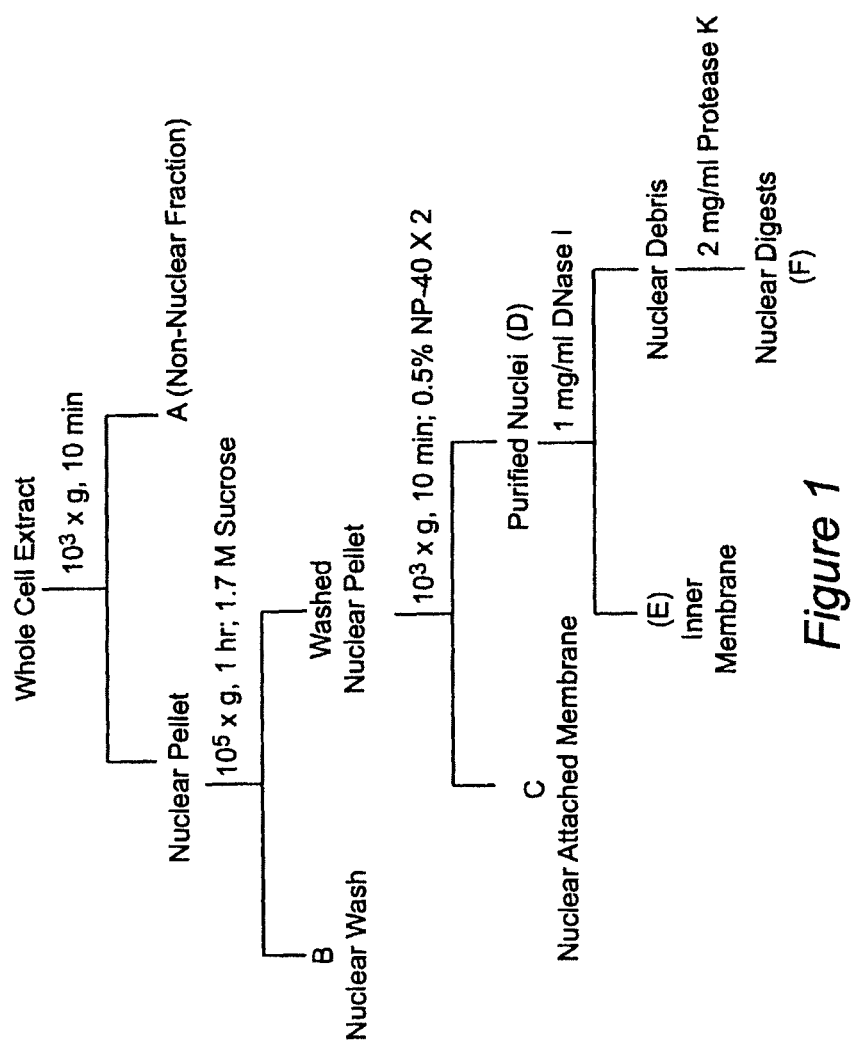
FIG. 1. Subcellular fractionation protocol. For details see "Experimental Procedures" in Example 1.

Disordered lipid metabolism and inflammatory responses play important roles in the pathogenesis of many fatal diseases, including atherosclerosis and nonalcoholic fatty liver diseases (NAFLD). The "two-hit" theory is widely accepted for explaining the occurrence and development of the diseases. The "first hit" is the initial intracellular lipid accumulation, whilst the "second hit" is inflammation and injury. Therefore, decreasing intracellular lipid levels and repressing the inflammatory response is the key to developing a new generation of therapeutic agents against these devastating diseases.

Recently, we have discovered the novel nuclear regulatory oxysterol (5-cholesten-3β, 25-diol 3-sulphate), and elucidated its metabolic pathway, and studied its role in lipid metabolism and inflammation. The oxysterol down-regulates key enzymes involved in lipid biosynthesis and subsequently decreases intracellular lipid levels by blocking the activation of liver oxysterol receptor (LXR)/sterol regulatory element binding protein signaling pathway. On the other hand, oxysterol decreases pro-inflammatory cytokine expression and secretion, and represses inflammatory response by activating peroxisome proliferation activator receptor gamma (PPARγ) and PPARγ/IκB/NFκB signaling pathway in macrophages and hepatocytes. A large body of experimental evidence has demonstrated that the oxysterol plays an important role in both "hits".

Most importantly, in vivo experimental studies showed that only one administration of the oxysterol decreases serum cholesterol and triglyceride by 20~40% and significantly increases HDL. Small molecule PPARγ agonists have been used for therapy of diabetes for a couple of decades and small molecule LXR agonists have been tested for therapy of hypercholesterolemia for couple of years. However, these agonists inevitably carry serious side effects. The new oxysterol, a naturally occurring PPARγ agonist and LXRs antagonist, has been shown to inhibit cholesterol and lipid biosynthesis in both hepatocytes and macrophages via LXR/SREBP and repress inflammatory responses via PPARγ/IκB/NFκB signaling pathway. Therefore, this naturally occurring oxysterol serves as a new class of medication for the treatment and the prevention of atherosclerosis, fatty liver, diabetes, and inflammatory diseases.

Both in vivo and in vitro data demonstrated that nuclear oxysterol increases nuclear PPARγ and decreases nuclear LXR levels in hepatocytes and macrophages. The nuclear oxysterol can decrease not only intracellular lipid levels but also repress the inflammatory response. Therefore the therapeutic concept of nuclear oxysterol represents a new approach to treating and preventing fatal diseases such as atherosclerosis and nonalcoholic fatty liver diseases.

The present invention is based on the discovery of 5-cholesten-3β, 25-diol 3-sulphate (25HC3S), a novel sulfated oxysterol with potent lipid (e.g cholesterol and triglyceride) lowering properties. The chemical structure of the sulfated oxysterol is as follows:

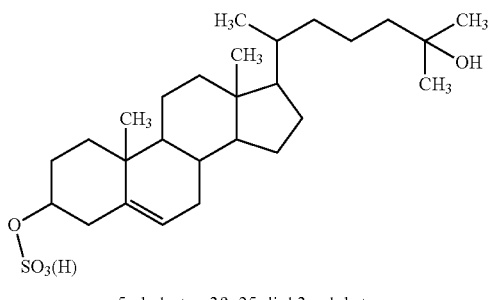

5-cholesten-3β, 25-diol 3-sulphate

This sulfated oxysterol is a nuclear cholesterol metabolite that decreases cholesterol and triglyceride levels in serum. The compound increases cholesterol secretion by increasing expression of cholesterol transporters in hepatocytes. The increase in cholesterol secretion and degradation ultimately leads to lower levels of serum cholesterol and triglycerides. Without being bound by theory, it appears that the sulfated oxysterol is made in the mitochondrion and translocates to the nucleus of the cell, where it acts to up-regulate genes involved in cholesterol and triglyceride metabolism. 5-cholesten-3β, 25-diol 3-sulphate is thus useful for preventing or treating diseases associated with elevated cholesterol (hypercholesterolemia) and triglycerides (hypertriglyceridemia), such as hyperlipidemia, atherosclerosis, coronary heart disease, stroke, non-alcoholic fatty liver diseases, etc. This sulfated oxysterol is especially suitable for in vivo use because it is an authentic natural compound that is biosynthesized in vivo by hydroxylation and sulfation of cholesterol. Thus, 5-cholesten-3β, 25-diol 3-sulphate should have few or no toxic side effects when administered to patients. In addition, the invention provides methods of preparing and administering 5-cholesten-3β, 25-diol 3-sulphate.

Example 6 shows that 5-cholesten-3β, 25-diol 3-sulphate also inhibits inflammation. Without being bound by theory, it appears that 25HC3S acts in macrophages as a PPARγ activator, and suppresses inflammatory responses via PPARγ/IκB/NFκB signaling pathway. 25HC3S appears to attenuate the inflammatory response by increasing IκB expression and decreasing IκB ubiquitination and degradation, thus exerting its effect through the PPARγ/IκB/NFB signaling pathway. As such, this compound is also useful for treating conditions that are caused or exacerbated by inflammation, particularly inflammation caused by lipid accumulation in cells, such as arthrosclerosis and fatty liver diseases.

The compound of the invention will be provided in a substantially purified form for use in the methods of the invention. By "substantially purified" we mean that the sulfated oxysterol is provided in a form that is at least about 75%, preferably at least about 80%, more preferably at least about 90%, and most preferably at least about 95% or more free from other chemical species, e.g. other macromolecules such as proteins or peptides, nucleic acids, lipids, and other cholesterol-related species (e.g. other cholesterol derivatives such as cholesterol metabolites, chemically modified forms of cholesterol such as various other hydroxylated cholesterol species, etc.). In one embodiment of the invention, the sulfated oxysterol of the invention may be isolated and purified from living cells. One embodiment of this method is described in Example 1 in the Examples section below. However, those of skill in the art will recognize that in order to generate larger quantities of the sulfated oxysterol, the compound may also be synthesized, either by synthetic chemical means, or by methods which involve the use of recombinant DNA technology (e.g. by using cloned enzymes to carry out suitable modifications of cholesterol). An exemplary synthesis scheme for 5-cholesten-3β, 25-diol 3-sulphate is as follows: A mixture of 25-hydroxycholesterol (0.1 mmol) and sulfur trioxide triethyl amine complex (0.12 mmol) in dry pyridine was stirred at room temperature for 2 hrs. The solvent was evaporated at 40° C. under nitrogen stream, and the pellets were dissolved in 500 ul of alkalined $CH_3OH$, pH 8.0. The sodium 5-cholesten-3b, 25-diol 3-sulfate was purified by flash chromatography to afford the product as a white solid.

The methods of the invention are useful for the treatment or prevention of conditions associated with high levels of cholesterol and triglyceride (hyperlipidemia). Such conditions may be either caused or exacerbated by high cholesterol and triglyceride, and include but are not limited to hyperlipidemia, atherosclerosis, heart disease, stroke, Alzheimer's, gallstone diseases, cholestatic liver diseases, non-alcoholic fatty liver disease (NAFLD), etc. As used herein NAFLD is intended to encompass early stages of the diseases (e.g. fat accumulation in liver cells), stages in which the fatty liver cells become inflamed (e.g. NASH or hepatitis), etc. The compound is also useful to treat inflammation or conditions caused or exacerbated by inflammation, for example, atherosclerosis, inflammatory bowel diseases, and diabetes (e.g. type 2 adult onset diabetes). By "treat" we mean that a disease condition has already developed, and the methods of the invention are used to ameliorate symptoms of the disease condition, either to stop or decrease progression of the disease, or to reverse symptoms of the disease, either partially or fully. Alternatively, by "prevent" we mean that the compounds of the present invention may be administered to patients prophylactically prior to the development of disease symptoms, e.g. to one who has high cholesterol but has not yet developed atherosclerosis, or to one who does not yet have high cholesterol but is at high risk for developing high cholesterol (e.g. as determined by genetic factors, family history, etc.); or to a patient diagnosed with fatty liver disease who is at risk of developing NASH or other conditions associated with high lipids, fat accumulation in cells, etc.

Those of skill in the art will recognize that the phrases "high lipid level", "high cholesterol level" and "high triglyceride level" generally relate to cholesterol levels in serum in the range of about 200 mg/dl or more, and triglyceride levels in serum greater than about 150 mg/dl. A determination of "high cholesterol" or "high triglyceride" is typically made by a health professional such as a physician, and the established meaning of "high" levels may vary somewhat from professional to professional. Further, the precise definition may vary somewhat depending on the state of the art, e.g. on findings from studies which investigate the relationship between lipid levels and diseases. Nevertheless, those of skill in the art will be able to identify suitable candidates for administration of the sulfated oxysterol of the present invention. By "lowering lipid levels" or "lowering triglyceride levels" or "lowering cholesterol levels" we mean that the level of free serum lipid/cholesterol/triglyceride in a patient is decreased by at least about 10% to 30%, and preferably at least about 30 to 50%, and more preferably at least about 50 to 70%, and most preferably at least about 70 to about 100%, or more, in comparison to the level of lipid in the patient prior to administration of the sulfated oxysterol. Alternatively, the extent of the decrease may be determined by comparison to similar untreated control individuals to whom the compound is not administered. Those of skill in the art are familiar with such determinations, e.g. the use of controls, or the measurement of lipid levels in the blood before and after administration of an agent that lowers lipids.

Implementation of the methods of the invention will generally involve identifying patients suffering from or at risk for developing conditions associated with high lipids, and administering the compound of the present invention in an acceptable form by an appropriate route. The exact dosage to be administered may vary depending on the age, gender, weight, and overall health status of the individual patient, as well as the precise etiology of the disease. However, in general for administration in mammals (e.g. humans), dosages in the range of from about 0.1 to about 100 μg or more of compound per kg of body weight per 24 hr., and preferably about 0.1 to about 50 μg of compound per kg of body weight per 24 hr., and more preferably about 0.1 to about 10 μg of compound per kg of body weight per 24 hr. are effective.

Administration may be oral or parenteral, including intravenously, intramuscularly, subcutaneously, intradermal injection, intraperitoneal injection, etc., or by other routes (e.g. transdermal, sublingual, oral, rectal and buccal delivery, inhalation of an aerosol, etc.). In a preferred embodiment, administration is oral. Further, administration of the compound may be carried out as a single mode of therapy, or in conjunction with other therapies, e.g. other cholesterol lowering drugs, exercise and diet regimens, etc.

The compounds may be administered in the pure form or in a pharmaceutically acceptable formulation including suitable elixirs, binders, and the like (generally referred to a "carriers") or as pharmaceutically acceptable salts (e.g. alkali metal salts such as sodium, potassium, calcium or lithium salts, ammonium, etc.) or other complexes. It should be understood that the pharmaceutically acceptable formulations include liquid and solid materials conventionally utilized to prepare both injectable dosage forms and solid dosage forms such as tablets and capsules and aerosolized dosage forms. In addition, the compounds may be formulated with aqueous or oil based vehicles. Water may be used as the carrier for the preparation of compositions (e.g. injectable compositions), which may also include conventional buffers and agents to render the composition isotonic. Other potential additives and other materials (preferably those which are generally regarded as safe [GRAS]) include: colorants; flavorings; surfactants (TWEEN, oleic acid, etc.); solvents, stabilizers, elixirs, and binders or encapsulants (lactose, liposomes, etc). Solid diluents and excipients include lactose, starch, conventional disintegrating agents, coatings and the like. Preservatives such as methyl paraben or benzalkium chloride may also be used. Depending on the formulation, it is expected that the active composition will consist of about 1% to about 99% of the composition and the vehicular "carrier" will constitute about 1% to about 99% of the composition. The pharmaceutical compositions of the present invention may include any suitable pharmaceutically acceptable additives or adjuncts to the extent that they do not hinder or interfere with the therapeutic effect of the sulfated oxysterol.

The administration of the compound of the present invention may be intermittent, or at a gradual or continuous, constant or controlled rate to a patient. In addition, the time of day and the number of times per day that the pharmaceutical formulation is administered may vary and are best determined by a skilled practitioner such as a physician. Further, the effective dose can vary depending upon factors such as the mode of delivery, gender, age, and other conditions of the patient, as well as the extent or progression of the disease condition being treated. The compounds may be provided alone, or in combination with other medications or treatment modalities.

In addition, the compound of the invention may also be used for research purposes.

EXAMPLES

Example 1

Sterol ligands play key roles in the maintenance of lipid homeostasis. The present study has identified a novel regulatory nuclear sulfated oxysterol, which is generated in mitochondria, translocates to the nucleus, and upregulates the rate of bile acid synthesis. At forty-eight hrs after infection with recombinant adenovirus encoding a mitochondria cholesterol transport protein (StarD1) in primary rat hepatocytes, bile acid synthesis increased by 5-fold. Concurrently, $[^{14}C]$ oxysterol derivatives with retention time at 11.50 min in HPLC elution profile was dramatically increased both in the mitochondria and in the nucleus, but not in culture media. The oxysterol product could be extracted into the chloroform phase from the methanol/water phase after sulfatase treatment, and had the same physical properties as 25-hydroxycholesterol. LC/MS/MS analysis showed the nuclear oxysterol with a molecular ion, m/z 481, in the Q1 full scan spectrum, and the presence of fragment ions at m/z 59, 80, 97, and 123 in its product scan spectrum. Thus, the nuclear oxyserol derivative can be characterized as 5-cholesten-3β, 25-diol 3-sulphate. The addition of nuclear extract from the cells overexpressing StarD1 or the addition of the purified oxysterol to primary rat hepatocytes significantly increased the rates of bile acid synthesis (>3.5 fold), suggesting this oxysterol derivative is an active regulator. These results provide evidence for a new regulatory pathway by which a novel potent regulatory nuclear sulfated oxysterol is generated in mitochondria, translocates to the nucleus, and upregulates bile acid synthesis.

Introduction

The biotransformation of cholesterol to primary bile acids occurs via two main pathways in hepatocytes (1). The "neutral" pathway is considered to be the major pathway at least in humans and rats (2). In this pathway the sterol nucleus is modified before the side-chain, beginning with hydroxylation of cholesterol at the 7α position. This reaction is catalyzed by cholesterol 7α-hydroxylase (CYP7A1), the first and rate-limiting step of this pathway. The ability to lower plasma cholesterol levels via the pharmacological control of CYP7A1 expression represents a therapeutic approach that has been in use for the last 30 years and is still of intense research interest. Multiple negative and positive modulators of CYP7A1 transcription have been identified both in tissue culture systems and in vivo (3) and many of these modulators are oxysterols, such as hydroxy-cholesterol molecules and bile acids. They function by activating nuclear receptors, such as liver X receptor (LXR) and farnesoid X receptor (FXR), which in turn regulate the expression of regulatory genes involved in bile acid biosynthesis, such as CYP7A1 and sterol 12α-hydroxylase (CYP8B1), the enzyme specific for cholic acid synthesis. Oxysterols are also key regulatory molecules for the expression of many other genes involved in the homeostasis of cholesterol, and other lipids, such as 3-hydroxy-3-methylglutaryl coenzyme A (HMG-CoA) reductase, low density lipoprotein (LDL) receptor, some ATP-binding cassette transporters, like the ABCA1 and ABCG8, and many others. They function by modulating the activity of either nuclear receptors or other transcriptional factors, such as the sterol regulatory binding proteins (SREBPs) (4-6). Thus, characterizing endogenous synthesized oxysterols and their mechanism of action is critical for a better understanding of lipid homeostasis.

The initial step in the "acidic" pathway is catalyzed by the enzyme mitochondrial sterol 27-hydroxylase (CYP27A1). The oxysterol intermediates of the "acidic" pathway such as 25-, or 27-hydroxycholesterol have been shown in vitro to be potent regulators in cholesterol homeostasis (7). Increased CYP27A1 activity in peripheral tissues may both down-regulate cholesterol synthesis through the SREBP pathway, and enhance the efflux of cholesterol and its elimination via LXR (8). However, the physiological and authentic in vivo LXR ligand is unknown (9).

We have recently found that overexpression of steroidogenic acute regulatory protein (StarD1), a protein which facilitates cholesterol transport to the mitochondria, dramatically increases cholesterol transport into mitochondria, the hydroxylation of cholesterol to oxysterol, and cholesterol catabolism to bile acids both in primary hepatocytes in culture and in vivo (10;11). This suggests that cholesterol delivery to the mitochondria, where the enzyme CYP27A1 is localized, is the rate-determining step for bile acid synthesis via the acidic pathway. Subsequently, StarD1 was found in isolated hepatocytes (12).

Overexpression of StarD1 in vivo increases bile acid synthesis not only to the same level as overexpression of CYP7A1, but also produces a similar composition of bile acids in mouse bile in vivo (11). Thus, it is reasonable to hypothesize that potent oxysterol molecule(s) might be generated in the mitochondria, thereby regulating bile acid synthesis, and playing an important role in maintenance of intracellular cholesterol homeostasis.

To test this hypothesis, a recombinant adenovirus encoding StarD1 was used to overexpress StarD1 in primary rat hepatocytes in order to increase bile acid synthesis. In this study we present evidence for previously unappreciated sulfated oxysterols in the nucleus of cells infected with the StarD1 adenovirus. The chemical structure of the most abundant nuclear oxysterol was characterized by HPLC, Triple Quadrupole LC/MS/MS, enzymatic digestion, and TLC analysis and was identified as 5-cholesten-3β, 25-diol 3-sulphate. We also provide evidence for a potential function (s) of this newly identified nuclear oxysterol in cholesterol catabolism.

Abbreviations: The abbreviations used are: CYP8B1, sterol 12α-hydroxylase; CYP27A1, cholesterol 27-hydroxylase; CMV, cytomegalovirus; CYP7A1, cytochrome P450 7α-hydroxylase; FXR, farnesil X receptor; SRE, sterol regulatory element; SREBP, sterol regulatory binding protein; HMG-CoA, 3-hydroxy-3-methylglutaryl-coenzyme A; Q-RT-PCR, quantitative reverse transcription PCR.

Experimental Procedures

Materials

Cell culture reagents and supplies were purchased from GIBCO BRL (Grand Island, NY). [$^{14}$C]Cholesterol and [$^{3}$H] 25-Hydroxycholesterol were purchased from New England Nuclear (Boston, MA). [$^{14}$C]27-Hydroxycholesterol was prepared as previously described (13). Cyclodextrin was purchased from Cyclodextrin Technologies Development Inc. (Gainsville, Fla.). Silica gel thin-layer chromatography plates (LK6 D) were from Whatman (Clifton, N.J.). Silica gel 1B TLC sheets were purchased from VWR (Bridgeport, N.J.). All other reagents were from Sigma Chemical Co (St. Louis, Mo.), unless otherwise indicated.

Adenovirus Preparation and Propagation

The adenovirus construct used in this study was obtained through the Massey Cancer Center Shared Resource Facility of the Virginia Commonwealth University as previously described (14).

RNA Preparation and Quantification

RNA was isolated and CYP7A1 was quantified using Northern blot assays (20 μg of total RNA) as previously described (15).

Culture and Subcellular Fractionation of Primary Rat Hepatocytes and Lipid Fractionation Primary rat hepatocyte cultures, prepared as previously described (16), were plated on 150 mm tissue culture dishes (~2.5×10$^7$ cells) in Williams' E medium containing dexamethasone (0.1 μM). Cells were maintained in the absence of thyroid hormone. Twenty-four hrs after plating, culture medium was removed, and 2.5 ml of fresh medium was added. Cells were then infected with recombinant adenovirus encoding either the StarD1 (Ad-CMV-StarD1) or the CYP7A1 (Ad-CMV-CYP7A1) cDNAs in front of the human cytomegalovirus promoter (CMV) or no cDNA, as a control virus. The viruses were allowed to incubate for at least 2 hrs in minimal culture medium with gentle shaking of the plates every 15 min. After 2 hrs of infection, unbound virus was removed, replaced with 20 ml of fresh medium, and 2.5 μCi of [$^{14}$C]cholesterol was added. After 48 hrs, cells were then harvested and processed for nuclei isolation as described (17) with minor modification (FIG. 1). Briefly, cells were disrupted by Dounce homogenization in buffer A (10 mM HEPES-KOH at pH 7.6, 1.5 mM MgCl$_2$, 10 mM KCl, 0.5 mM dithiothreitol, 1 mM sodium EDTA, 1 mM EGTA) and spun at 1,000× g for 10 min. The nuclear pellet was further fractionated by resuspension in 2.5 ml of a 1:1 mixture of buffer A and buffer B (2.4 M Sucrose, 15 mM KCl, 2 mM sodium EDTA, 0.15 mM spermine, 0.15 mM spermidine, 0.5 mM dithiothreitol) and centrifuged at 100,000× g for 1 hr at 4° C. through a 1 ml cushion of 3:7 mixture of buffer A and B. The washed nuclear pellet was resuspended in buffer A containing 0.5% (v/v) Nonidet P-40 and centrifuged at 1000×g for 10 min at 4° C. The supernatant is designated as nuclear attached membrane (fraction C) and the pellets as purified nuclei (fraction D).

The purified nuclei (Fraction D) were resuspended and digested by 2 mg/ml of DNase I in 50 mM of acetic buffer, pH 5.0, 10 mM $MgCl_2$ at 37° C. for 2 hrs. After centrifugation at 10,000×g for 20 min, the supernatant was designed as inner nuclear membrane (fraction E). The pellets were further digested by 2 mg/ml of proteinase K in phosphate buffered saline solution (PBS) at 50° C. for 16 hrs and the solution was designed as nuclear protease digests (fraction F). Total lipids in each fraction were extracted by adding 3.3 volumes of chloroform:methanol (1:1) and separated into two phases, methanol/water and chloroform phases as previously described (18). The counts of [$^{14}$C]cholesterol derivatives in the methanol/water and chloroform phases were measured by liquid scintillation counting (LC 60001C, Beckman, Fullerton, Calif.).

TLC and HPLC Analysis of Cholesterol Derivatives

The [$^{14}$C]cholesterol/cholesterol derivatives in chloroform and methanol/water phases were examined by thin layer chromatograph (TLC) (E. Merck, Darmstadt, Germany) using different developing solvent systems: toluene:ethyl acetate (2:3, v/v) for the [$^{14}$C]cholesterol/oxysterols in chloroform phase, and ethyl acetate:cyclohexane:acetic acid (92:28:12; v/v/v) for those in methanol/water phases. The [$^{14}$C]cholesterol/cholesterol derivatives were visualized in Phosphorimager using Fuji imaging plates (Fujifilm BAS-1800II, Fuji Photo Film Co., LTD, Japan).

Total [$^{14}$C]-cholesterol derivatives in chloroform phase were analyzed by HPLC on an Ultrasphere Silica column (5 µx4.6 mm×25 cm; Backman, USA) using HP Series 1100 solvent delivery system (Hewlett Packard, Japan) at 1.3 ml/min flow rate. The column was equilibrated and run in a solvent, Hexane:Isopropanol:Glacial Acetic Acid (965:25:10, v/v/v), as the mobile phase. The effluents were collected every 0.5 min (0.4 ml per fraction) except as indicated. The counts of [$^{14}$C]cholesterol/cholesterol derivatives were determined by Scintillation Counter. The column was calibrated with cholesterol, [$^{3}$H]25-hydroxycholesterol, and [$^{14}$C]27-hydroxycholesterol.

Total [$^{14}$C]-cholesterol derivatives found in methanol/water phases were analyzed on an Ultrasphere PTH C-18 column (5 µx4.6 mm×25 cm; Backman, USA) at 0.8 ml/min flow rate. The column was equilibrated and run in 20 mM $KH_2PO_4$, pH 4.2:acetonitrile:methanol (1:3:6, v/v/v) as the mobile phase. The effluents were monitored at 195 nm and collected every 0.5 min (0.4 ml per fraction) except as indicated. The column was calibrated with tauroursodeoxycholic acid, glycoursodeoxycholic acid, taurocholic acid, glycocholic acid, taurochenodeoxycholic acid, taurodeoxycholic acid, and progesterone.

Sulfatase Treatment of Purified Nuclear [$^{14}$C]cholesterol Derivatives

The purified nuclear [$^{14}$C]cholesterol derivatives were digested with 2 mg/ml of sulfatase (EC 3.1.6.1) (Sigma, St Louis, Mo.) in 50 mM of acetic buffer, pH 5.0 by incubation at 37° C. for 4 hrs. The products were extracted into chloroform phase from methanol/water phase by adding 3.3 volume of methanol:chloroform (1:1, v/v) to reaction solution. [$^{14}$C]Cholesterol derivatives in both chloroform and methanol/water phases were then analyzed by TLC and HPLC as stated above.

Reverse Phase Liquid Chromatography/Mass Spectrometry/Mass Spectrometry (LC/MS/MS) Analysis of Nuclear Cholesterol Derivatives Reverse phase liquid chromatographic separation was performed on an HP series 1100 system (Agilent Technologies, Palo Alto, Calif.) and CTC HTS-PAL autosampler (Leap Technologies, Carrboro, N.C.). Separation was carried on a ThermoKeystone Aquasil C18 column (5 µm, 2.1 mm×100 mm). The mobile phase consisted of (A), 0.1% formic acid in water, and (B), 0.1% formic acid in acetonitrile. The 20 min gradient was as follows: 0-10.0 min, 10%-95% B linear; 10.0-15.0 min, 95% B; 15.0-15.1 min, 95%-10% B linear; 15.1-20.0 min, 10% B. The mass detector was an API 4000 (MDS Sciex, Toronto, Canada)

The elution stream (0.3 ml/min) from the HPLC apparatus was introduced into a MDS Sciex API 4000 Triple Quadrapole Mass Spectrometer with a Turbo IonSpray ionization (ESI) source for the analyses. The mass spectrometer was operated in negative ion modes and data were acquired using both full scan mode as well as the product ion mode for MS/MS.

The sample was reconstituted into methanol:water (20:80, v/v). The solution containing the fraction of 11.50 min peak was infused into the LC/MS/MS system to optimize ESI-MS-MS parameters. The optimized parameters for Q1 full scan under the negative mode were: CUR:10; GS1: 40; GS2: 40; TEM:400; IS: −4500; DP: −150; EP: −10. The optimized parameters for the product scan of 481 under the negative mode were: CUR:10; GS1:40; GS2: 40; TEM: 400; IS: −4500; CAD: 5; DP: −150; EP: −10; CE: 50; CXP: -15.

Bile Acid Biosynthesis and Analysis

Bile acid synthetic rates were determined by the addition of 2.5 µCi of [$^{14}$C]cholesterol to each P150 mm plate of confluent primary rat hepatocyte cultures (~2.5×10$^7$ cells) 24 hrs after plating. Media and cells were harvested 48 hrs after viral infection. Conversion of [$^{14}$C]cholesterol into [$^{14}$C]-methanol-water soluble products was determined by scintillation counting after extraction with chloroform-methanol (2:1, vol/vol) of cells and of culture media. Rates of bile acid biosynthesis following recombinant adenovirus infection were calculated as the ratio of [$^{14}$C]-methanol-water soluble counts to the sum of chloroform plus methanol-water counts. Individual bile acids were identified by HPLC analysis as described above.

Time course of bile acid synthesis: Time points for conversion of [$^{14}$C]-cholesterol to [$^{14}$C]-bile acids were carried out using P150 mm tissue culture dishes Aliquots (1/100) of media were collected in duplicate in a microfuge tube and kept frozen until analysis. A mini Folch extraction was carried out by adding 3 volume of methanol:chloroform (1:1) to the culture medium. The tubes were vigorously vortexed and centrifuged at 16,000 g for 6 min. The phases were collected separately and counted.

Statistics

Data are reported as mean ±standard error. Where indicated, data were subjected to t-test analysis and determined to be significantly different if P<0.05.

Results

Figure 2A:
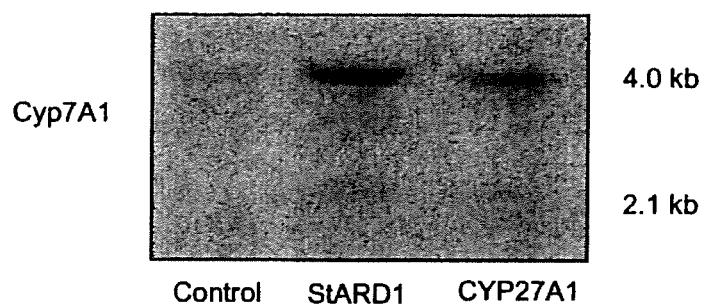
FIGS. 2A-2C. Effects of overexpression of StarD1 on Cyp7A1 mRNA expression in primary rat hepatocytes. At day five following infection of virus control, virus encoding StarD1, and CYP27A1 as indicated, cells were harvested and total RNAs were extracted. To each lane, 20 μg of total RNA was loaded. Specific Cyp7A1 mRNAs (FIG. 2A) were determined by Northern blot analysis. Cyclophilin was used as control (FIG. 2B). The expressions of Cyp7A1 mRNAs were increased by 6-fold (n=3) following overexpression of StarD1 and 2.5 fold following CYP27A1 as indicated (FIG. 2C).
Figure 2B:
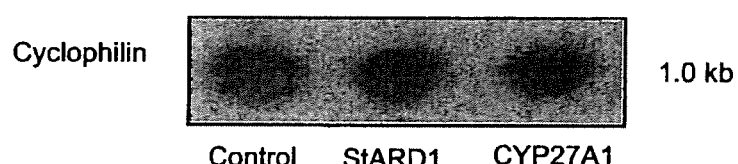
Figure 2C:
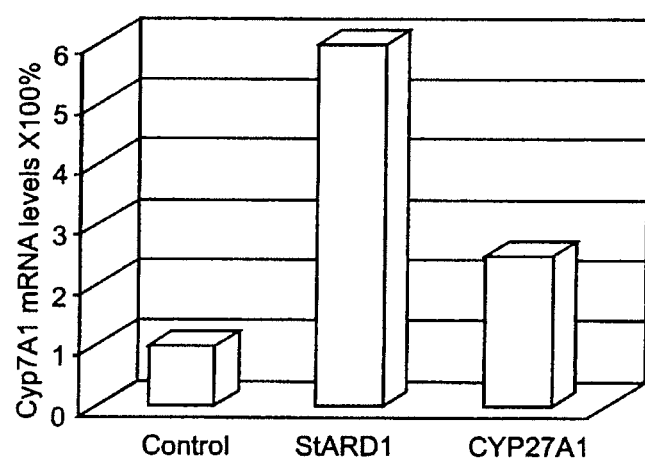

A Novel Nuclear Oxysterol is Generated in Mitochondria and Translocated to the Nucleus in Primary Rat Hepatocytes Upon StarD1 Overexpression Primary rat hepatocytes were infected with an adenovirus encoding either StarD1 or CYP7A1 as explained in Experimental Procedures. Forty-eight hrs after infection, bile acid synthesis increased 4-fold and 7-fold respectively, as we previously reported (18). Cells infected with control virus have similar levels of bile acid synthesis as uninfected cells. To test whether overexpression of StarD1 affects the expression of LXR targeting genes following generation of the nuclear oxysterol, the regulation of CYP7A1 expression was investigated following StarD1 overexpression. CYP7A1 mRNA levels increased by 6-fold (n=3) at day 3 following StarD1 overexpression (FIGS. 2A-2C).

Figure 3:
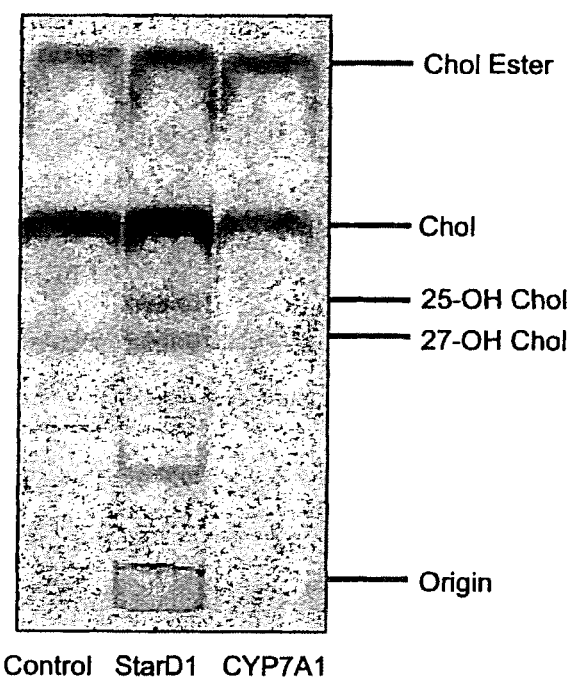
FIG. 3. Thin layer chromatographic analysis of the chloroform extractable cholesterol derivatives. Rat primary hepatocytes were infected with the indicated viruses. Forty-eight hrs later cells were harvested and nuclear lipids extracted and analyzed as explained under "Experimental Procedures".
Figure 4A:
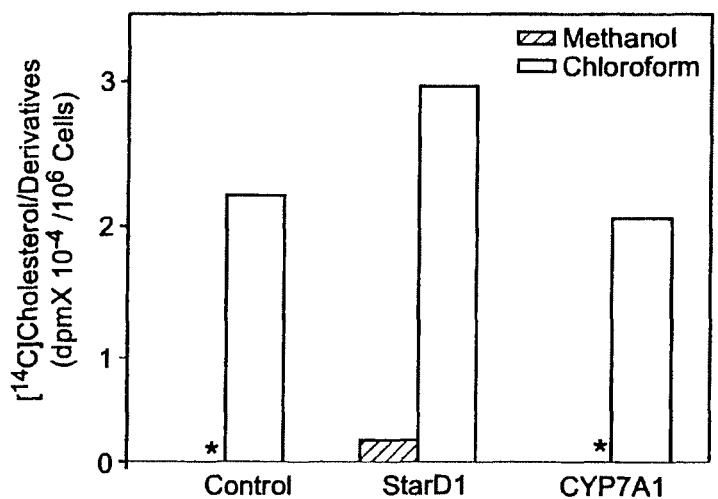
FIGS. 4A and 4B. Phase distribution of [$^{14}$C]cholesterol derivatives in nuclei of primary rat hepatocytes following overexpression of StarD1 and CYP7A1. Rat primary hepatocytes were infected with the indicated viruses. Forty-eight hrs later cells were harvested and subcellular fractions prepared. Fractions E and F were processed for lipid analysis as explained under Experimental Procedures".
Figure 4B:
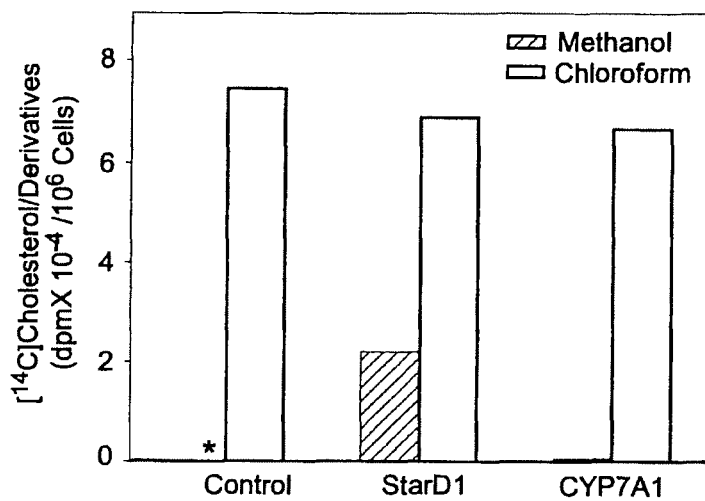

The subcellular distribution of [$^{14}$C]-cholesterol derivatives was monitored by adding exogenous [$^{14}$C]cholesterol to the hepatocyte culture 2 hrs after infection and is summarized in Table 1. Approximately 50% of the total counts of [$^{14}$C]cholesterol/cholesterol derivatives were found in nuclear-related fractions. The other 50% were located in other subcellular organelles including cytosol, plasma membranes, lysosomes, and mitochondria (Fractions A and B). Only a small number of counts were detected in the inner membrane fraction (Fraction E). Interestingly, the total extractable [$^{14}$C]cholesterol/cholesterol derivatives in nuclear debris from StarD1-infected cells was significantly (25%) higher than those of CYP7A1-infected or control nuclear extracts (Fraction F). TLC analysis of the chloroform-extractable cholesterol derivatives found in the nuclear fraction (Fraction D) in StarD1-infected hepatocytes showed four bands, which migrated like cholesterol ester, cholesterol, 25-hydroxycholesterol, and 27-hydroxycholesterol respectively (FIG. 3). Only cholesterol ester, cholesterol, and 27-OH cholesterol were detected in control-infected cells, with cholesterol ester and cholesterol in CYP7A1-infected cells. These results suggested that StarD1 overexpression increased translocation of cholesterol derivatives, 25-hydroxycholesterol, to the nucleus. The presence of 25-hydroxycholesterol in the nucleus following StarD1 overexpression has been confirmed by mass spectrometry/mass spectrometry (MS/MS) analysis (data not shown). 25-Hydroxycholesterol is a minor oxysterol that may be formed in different types of tissues by a specific enzyme that may not belong to the cytochrome P-450 family (19). Interestingly, cholesterol-derivatives in the methanol/water phase extracted from the nuclear debris were dramatically increased in the StarD1-overexpressing cells compared with control and CYP7A1-overexpressing cells (FIGS. 4A and 4B).

TABLE 1

Distribution of [$^{14}$C]cholesterol derivatives in primary rat hepatocytes following StarD1 or CYP7A1 overexpression*.

| Subcellular Fraction | Non-nuclear | | Nuclear | | |
|---|---|---|---|---|---|
| | A | B | C | E | F |
| Control | 43 ± 2 | 23 ± 5 | 47 ± 3 | 1.0 ± 0.2 | 7 ± 3 |
| StarD1 | 38 ± 8 | 3.1 ± 2 | 36 ± 6 | 1.7 ± 0.1 | 10 ± 2 |
| CYP7A1 | 43 ± 3 | 2.9 ± 4 | 49 ± 8 | 1.1 ± 0.2 | 8 ± 2 |

*[$^{14}$C]Cholesterol was added at 2 hrs after adenovirus infection and cells were harvested 48 hrs later. Subcellular fractions were prepared as described under "Experimental Procedures". An aliquot from each fraction was taken for liquid scintillation counting. Values represent the mean of three experiments ± SD of the percentage of radioactivity found in each fraction with respect to the total radioactivity found in all fractions.

Figure 5A:
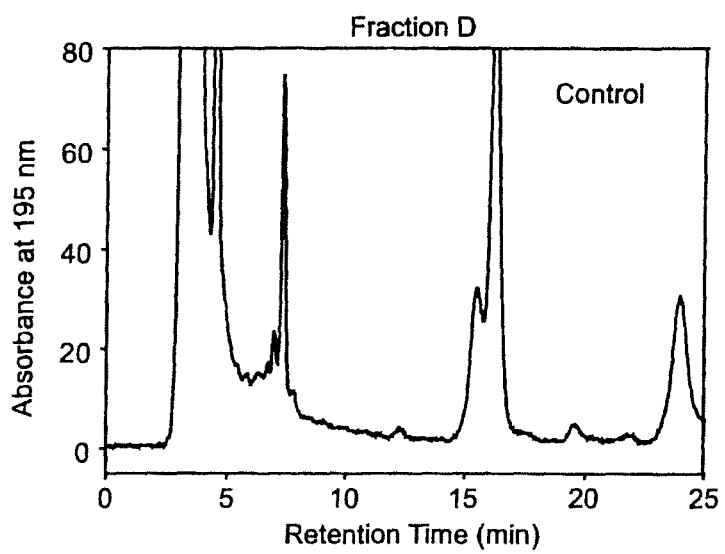
FIGS. 5A-5I. HPLC analysis of [$^{14}$C]cholesterol derivatives in the nuclear fraction (Fraction D) and non-nuclear fraction (Fraction A). Twenty-four hrs following the indicated recombinant adenovirus infection, cells were harvested and nuclear and non-nuclear fractions (Fractions A and D) were isolated, extracted by the Folch method and the methanol/water phase analyzed.
Figure 5B:
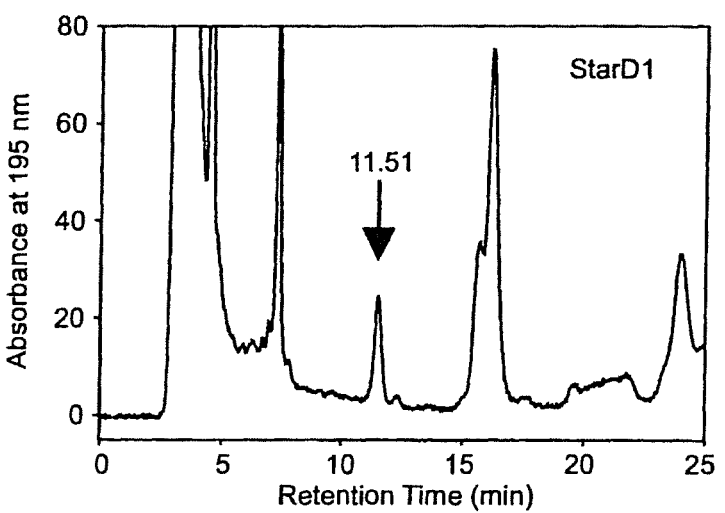
Figure 5C:
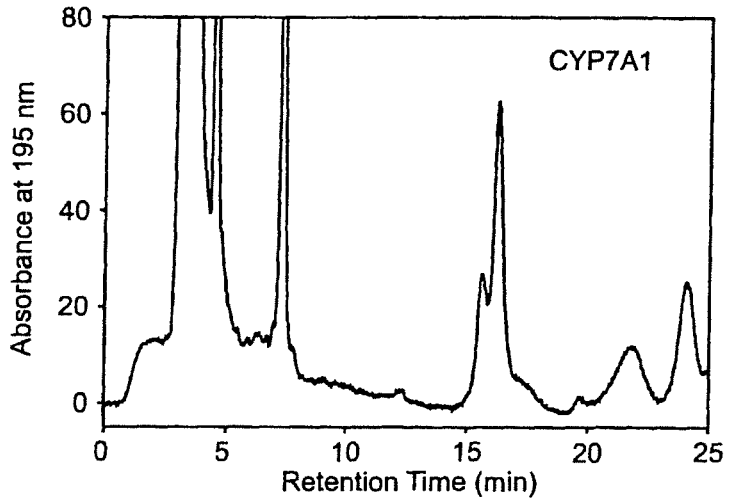
Figure 5D:
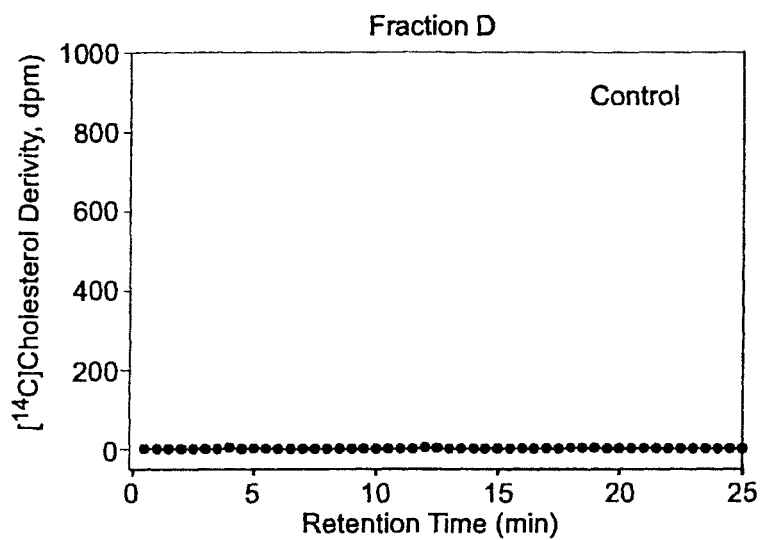
Figure 5E:
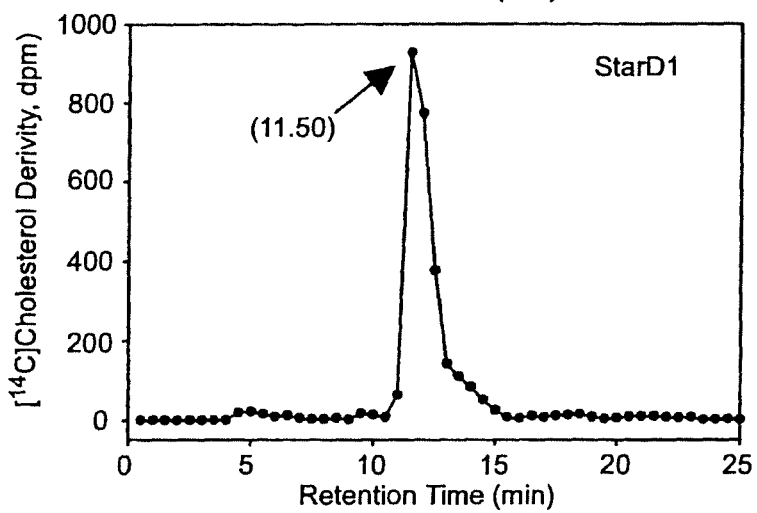
Figure 5F:
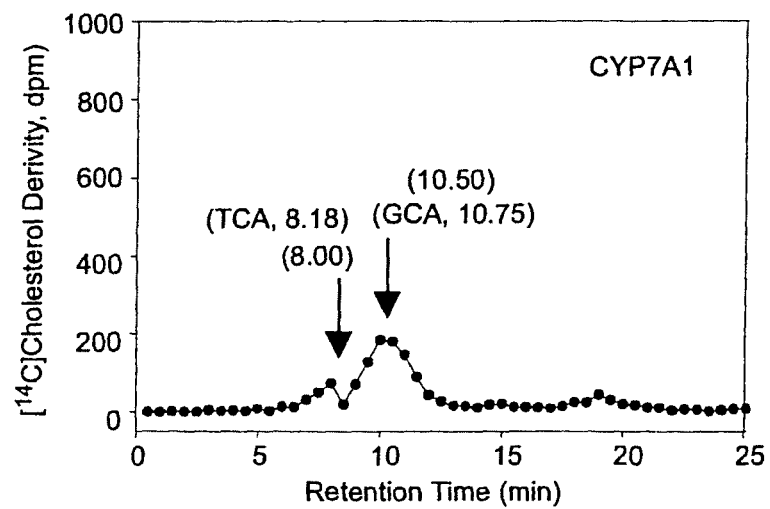
Figure 5G:
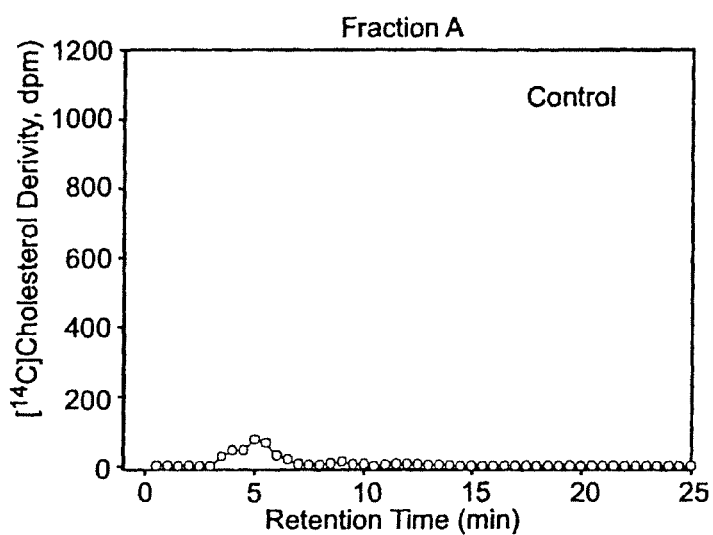
Figure 5H:
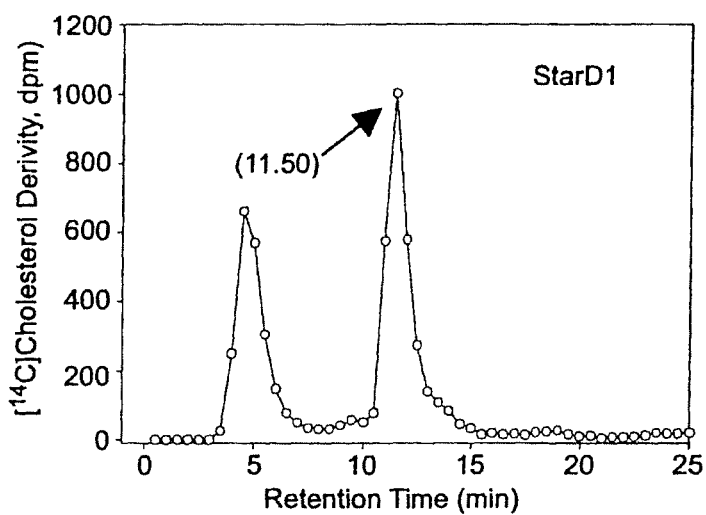
Figure 5I:
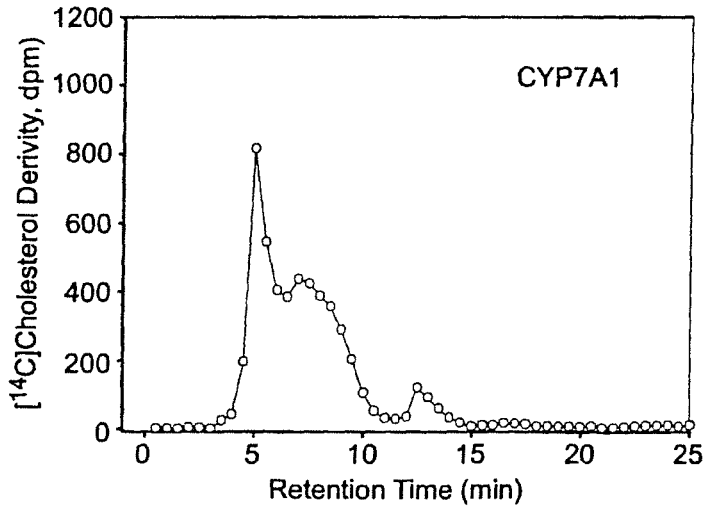

We then proceeded to analyze the composition of the cholesterol derivatives in the different subcellular fractions of StarD1 overexpressing hepatocytes. We first performed HPLC analysis of [$^{14}$C]cholesterol derivatives in the methanol/water phases from the nuclear and non-nuclear fractions. FIGS. 5A-5I showed the 195 nm profiles, which nonspecifically detected double bonds containing molecules, and the specific radioactivity incorporated in each fraction derived from the [$^{14}$C]cholesterol that had been added to the cultures after infection. The 195 nm profiles were relatively similar in the nuclear fraction (Fraction D) from cells infected either with the StarD1, CYP7A1, or null recombinant viruses, except for an extra peak with retention time of 11.51 min, which was located between glycocholic acid (10.75 min) and taurochenodeoxycholic acid (12.50 min) (FIG. 5A). This 11.50 min peak was the only fraction that contained $^{14}$C-labelled cholesterol derivatives and was detectable only in StarD1 overexpressing cells (FIG. 5B). The non-nuclear fraction (Fraction A) from the StarD1 overexpressing cells contained two major [$^{14}$C]cholesterol derivative peaks with retention times at 5 and 11.50 min. The 11.50 min peak was not detected in cells infected with either the control or the CYP7A1 viruses (FIG. 5C).

Figure 6A:
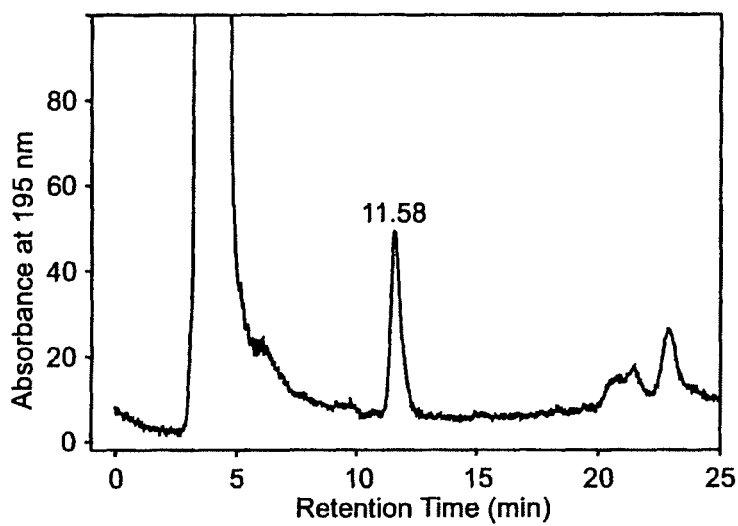
FIGS. 6A-6F. HPLC analysis of the cholesterol derivatives extracted from the nuclei, mitochondria, and culture media. Rat primary hepatocytes were infected with the StarD1 adenovirus and two hrs later [$^{14}$C]cholesterol was added to the media. Twenty-four hrs following, cells and culture media were harvested. Nuclei and mitochondria were isolated as described under "Experimental Procedures". Total lipids were extracted from the nuclei, mitochondria, and culture media by Folch partitioning into methanol phase, and analyzed by HPLC as described in "Experimental Procedures".
Figure 6B:
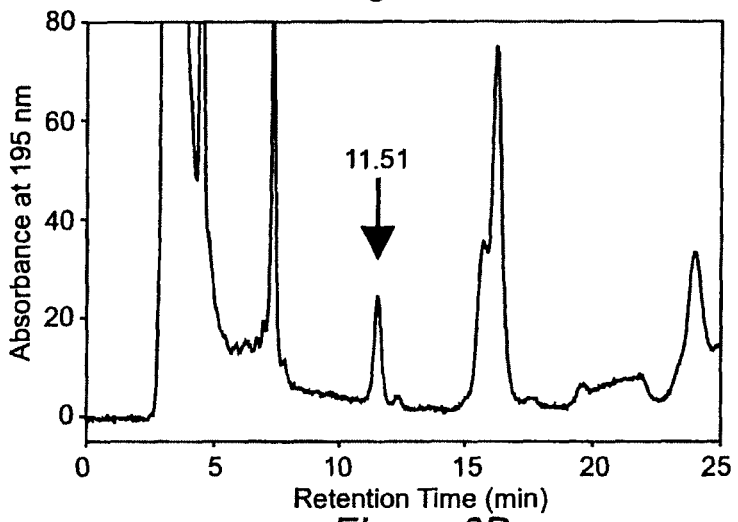
Figure 6C:
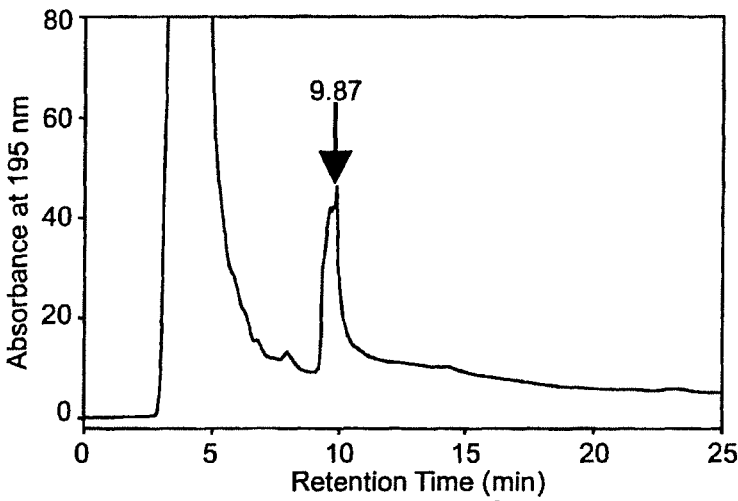
Figure 6D:
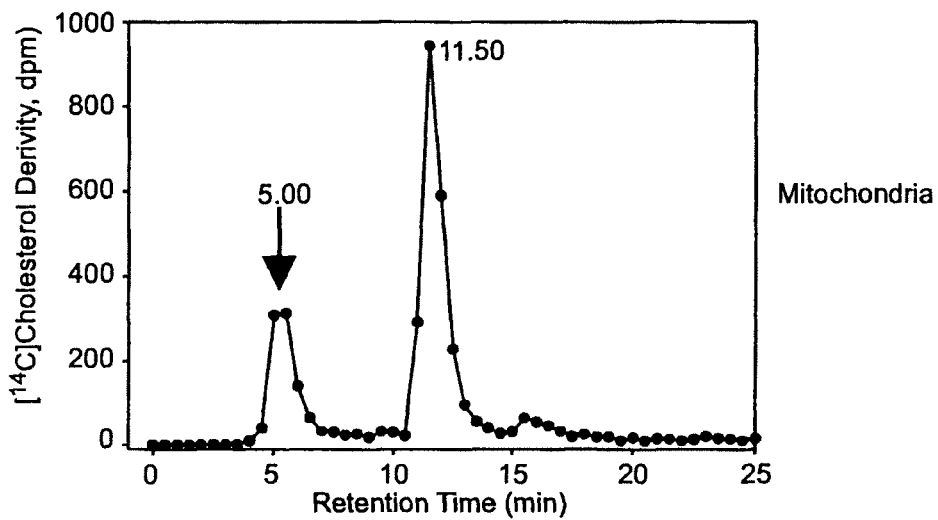
Figure 6E:
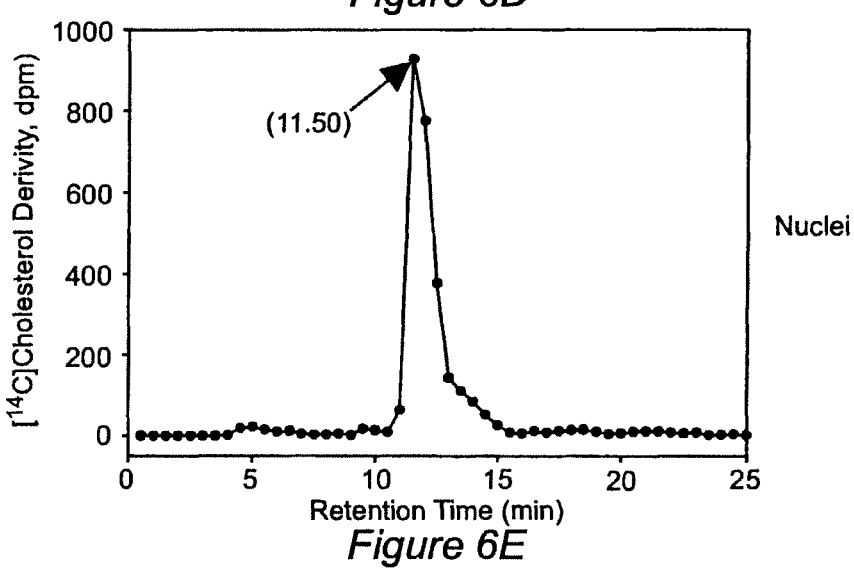
Figure 6F:
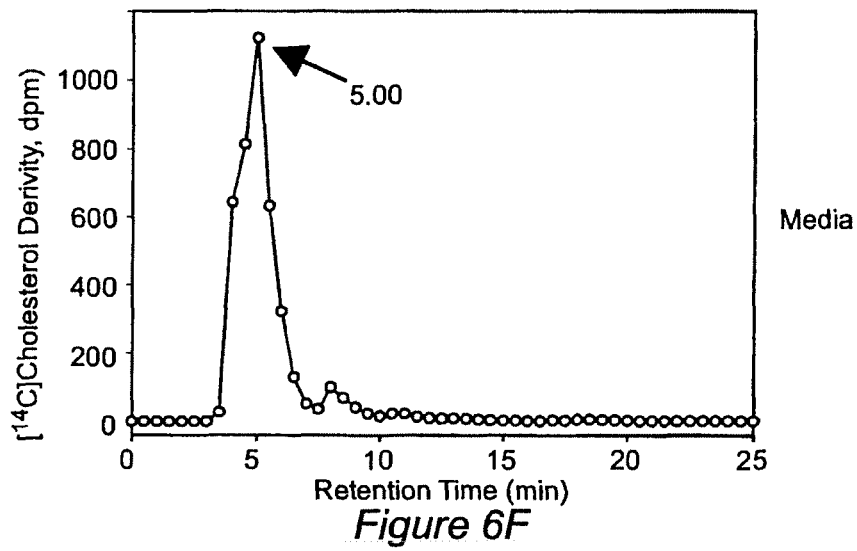

Further analysis of the cholesterol derivatives in the methanol/water phases extracted from mitochondrial, nuclear fractions, and culture media following overexpression of StarD1 protein showed that two [$^{14}$C]cholesterol derivatives with retention times at 5.00 min and 11.5 min were found in mitochondria (FIGS. 6A and D). Furthermore, the 11.5 min peak was present only in mitochondria and nuclei but not in the media (FIGS. 6B and E) suggesting that a cholesterol-derived molecule should be generated in mitochondria and translocated to the nucleus. The peak with retention time at 5.00 min was found only in mitochondria and culture media, but not in the nucleus (FIGS. 6C and F) suggesting that the molecule presented in that peak was secreted from the cells. Therefore, the cholesterol derivative with a retention time of 11.50 min in the HPLC system, which is generated in the mitochondria and translocates to the nucleus, is defined as a nuclear oxysterol, and the other as a secretory oxysterol.

Figure 7A:
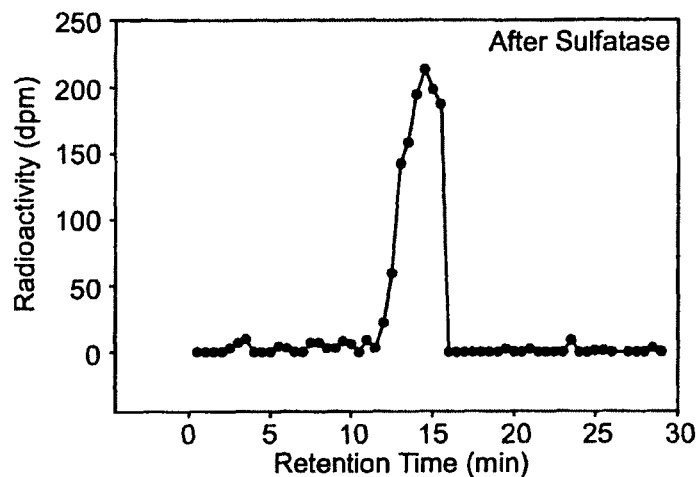
FIGS. 7A-7D. Characterization of the nuclear oxysterol by enzymatic digestion followed by HPLC and TLC. Nuclear [$^{14}$C]oxysterol derivatives were isolated from StarD1 overexpressing rat primary hepatocytes and digested with 1 mg/ml of sulfatase in acetic acid buffer, pH 5.0, overnight. Total lipids were extracted with chloroform/methanol and separated by Folch partitioning. The products in the chloroform and methanol/water phase were analyzed by HPLC using a mixture of 965 ml hexane, 25 ml isopropanol, and 10 ml acetic acid as mobile phase, 1.3 ml/min flow rate and $^{14}$C quantified.
Figure 7B:
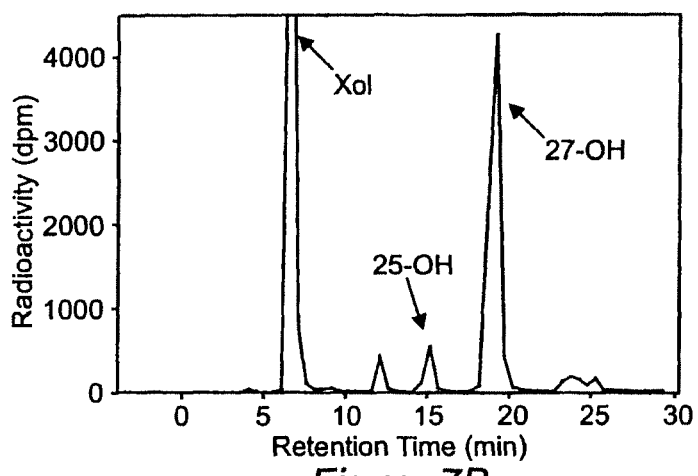
Figure 7C:
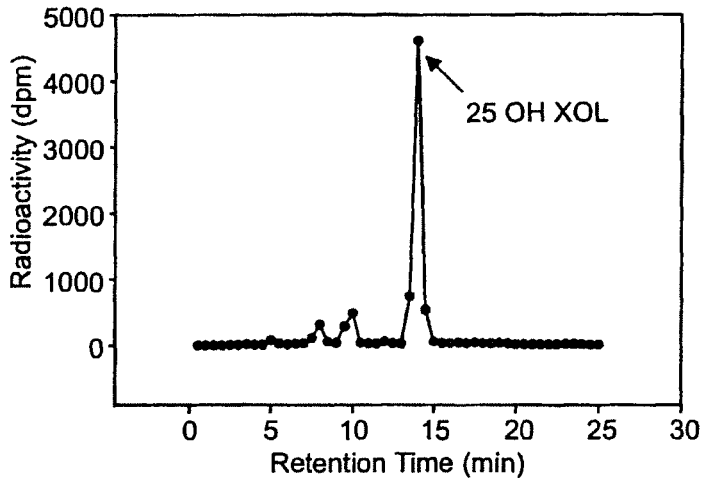
Figure 7D:
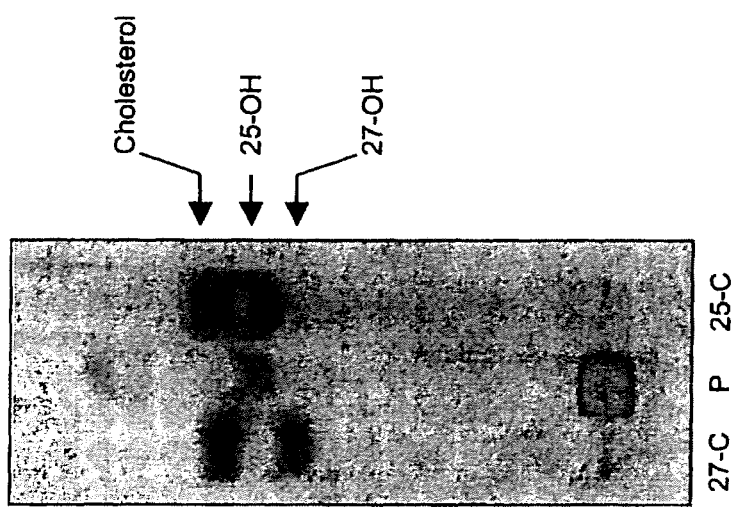

To characterize the chemical structure of the nuclear oxysterol, we proceeded to purify it by HPLC using C18 and silica columns, and analyze it by enzymatic digestion, TLC, and HPLC analysis. First, to detect the potential presence of sulfate group(s) in the nuclear oxysterol molecule, the purified nuclear oxysterol was digested with sulfatase. The products were extracted with methanol/chloroform, separated by Folch partitioning, and characterized by HPLC and TLC analysis. Following sulfatase treatment, the nuclear oxysterol products were extracted into the chloroform phase from the methanol/water phase and show the same retention time as 25-hydroxycholesterol, but not 27-, no 24-hydroxycholesterol in our HPLC system (FIG. 7A-C), and the same relative mobility as 25-hydroxycholesterol on the TLC plate (FIG. 7D), suggesting that the nuclear oxysterol derivative is a sulfated 25-hydroxycholesterol.

Figure 8A:
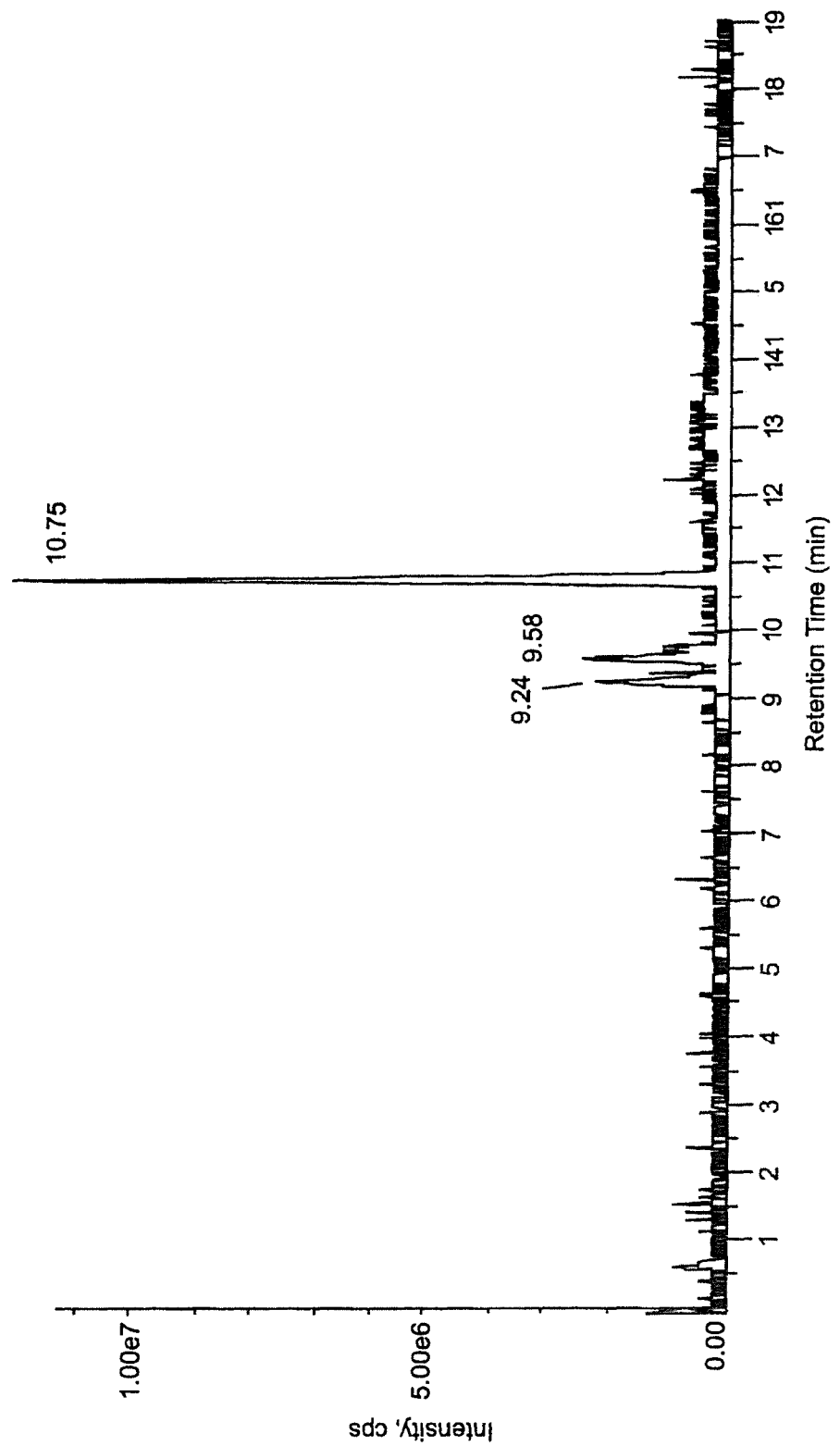
FIGS. 8A-8C. Characterization of nuclear oxysterol by negative ion-triple quadruple mass spectrometry (LC/MS/MS).
Figure 8B:
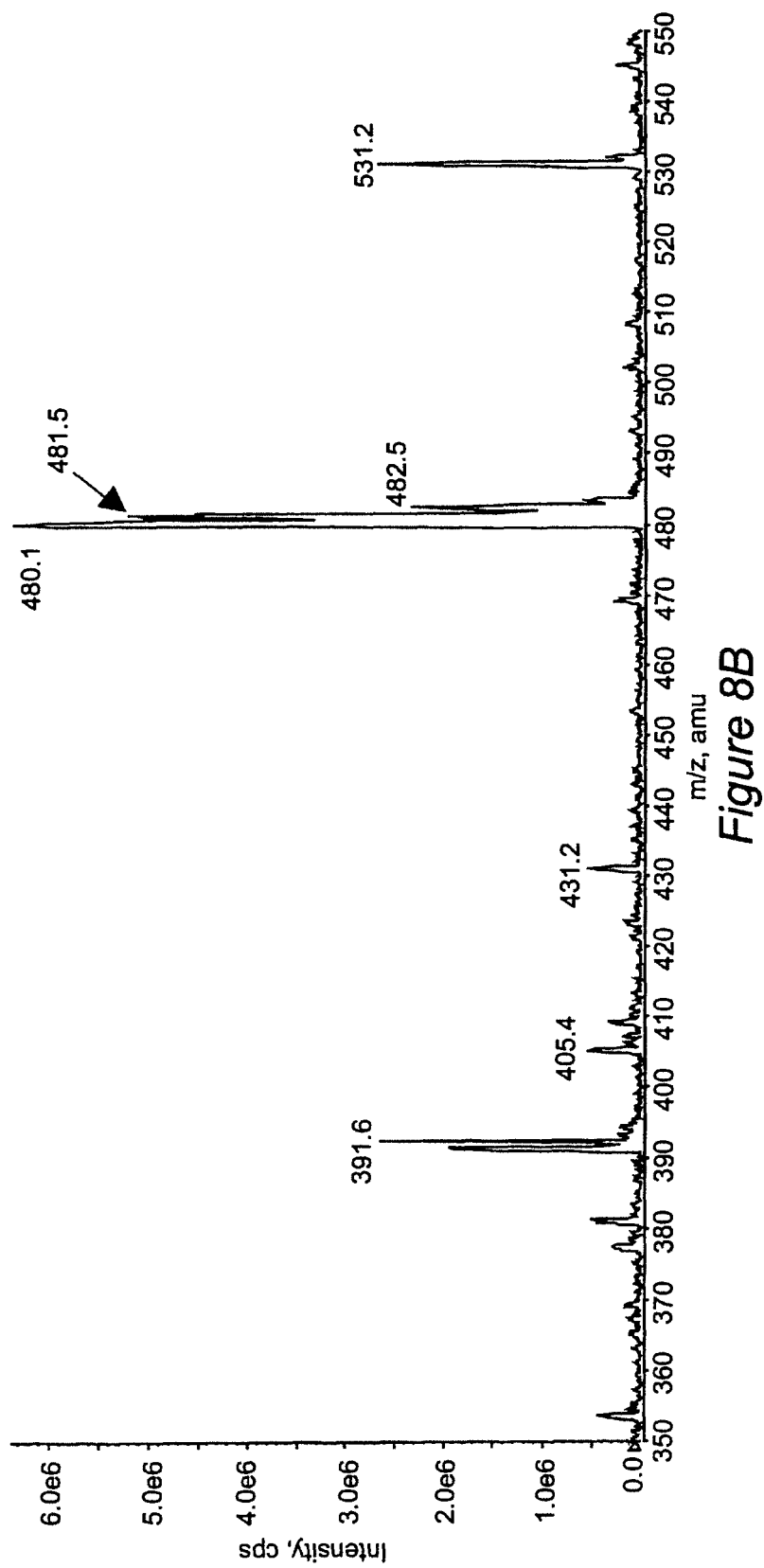
Figure 8C:
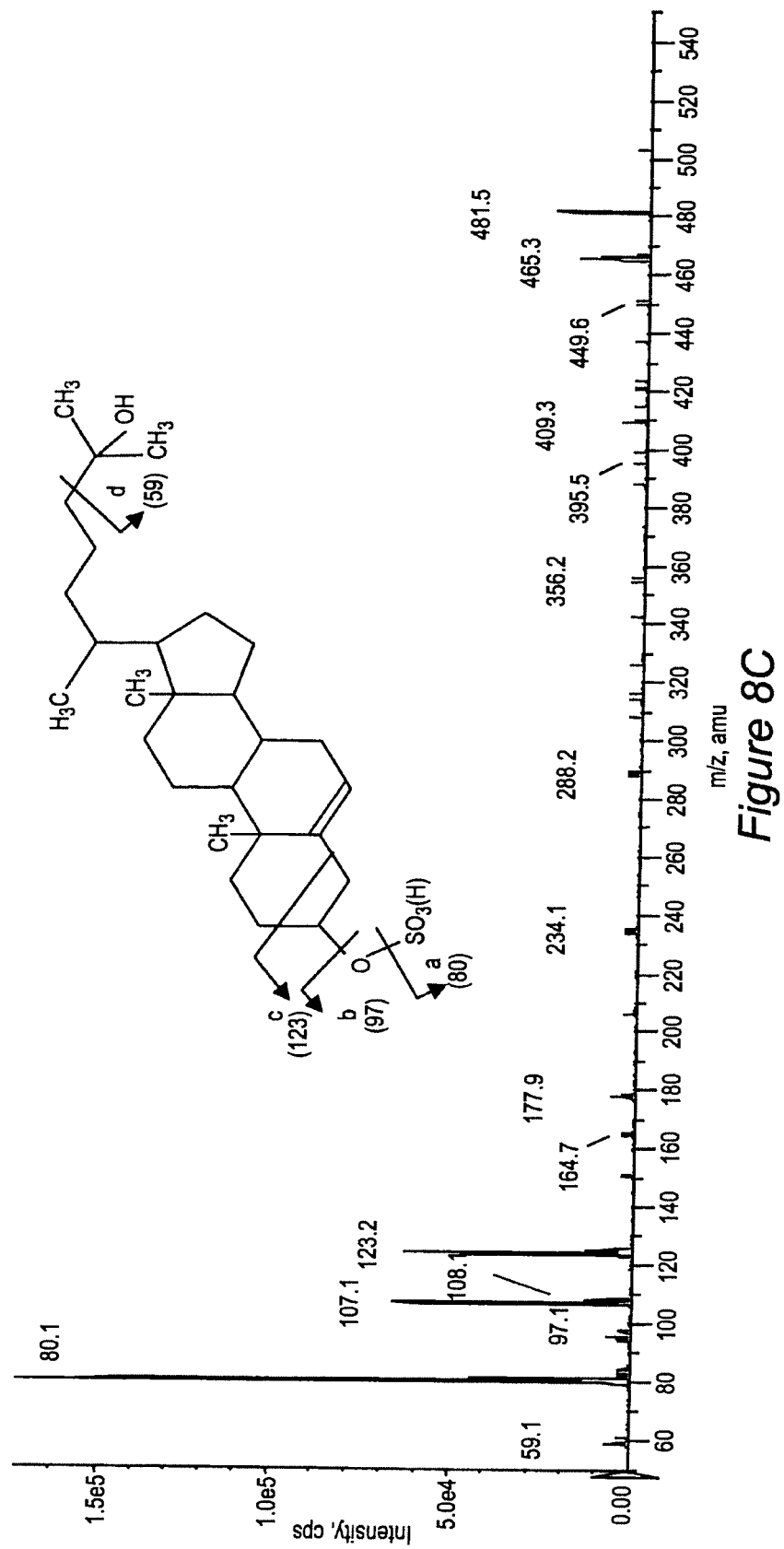

To confirm the chemical structure of the nuclear oxysterol derivative, the purified nuclear sulfated oxysterol was further analyzed by LC/MS/MS Mass Spectrometry. After we performed LC/MS (Q1 full scan mode, 350 to 550 atomic mass units, amu) under negative ionization mode, a prominent peak was observed at a retention time of 10.75 min in a selected ion chromatogram of mass ion at m/z=481 as shown in FIG. 8A. The Q1 full scan spectrum showed the peak at 10.75 min mainly contained molecule ions, m/z 480.1 and 481.5 (FIG. 8B). Further analysis showed the molecule ion, m/z 480.1 did not contain a sulfate group on hydroxyl group (m/z 97) (data not shown). However, the molecule ion, m/z 481.5, corresponds to sulfate group 97 and cholesterol (MW 386). This molecule ion was further analyzed by LC/MS/MS (product scan of m/z 481) under negative ionization mode (FIG. 8C). The characteristic fragment ions were observed at m/z=80(a), 97(b), 107, 123(c), 288, 465, and 59(d) in the product scan spectrum of m/z 481 (FIG. 8C). These observed fragment ions indicate that the nuclear oxysterol is a sulfated oxysterol with a sulfate group on 3-OH position (20) and a hydroxyl group on side chain, m/z 59, (molecular mass 482=80 (sulfate)+16 (O)+386 (cholesterol). Combined with data from HPLC, enzymatic digestion, and TLC analysis, the nuclear oxysterol derivative can be characterized as 5-cholesten-3β, 25-diol 3-sulphate (25-hydroxycholesterol 3-sulfate) as shown in (FIG. 8C).

Figure 9A:
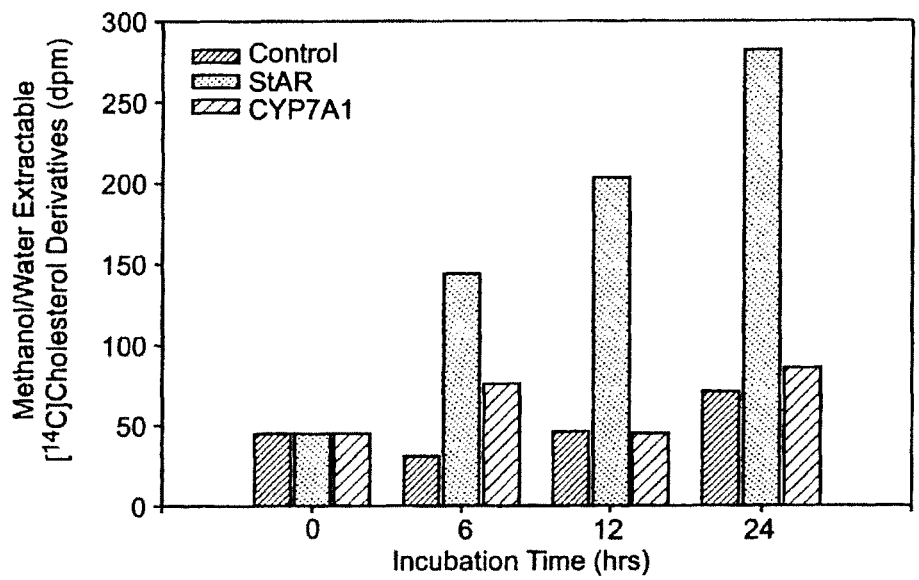
FIGS. 9A-9B. Effect of the nuclear oxysterol on cholesterol uptake and bile acid biosynthesis. Rat primary hepatocyes were treated with nuclear extracts (methanol/water phase) (A and B) or purified nuclear oxysterol dissolved in control nuclear extract (C) 24 hrs after plating them. Then [$^{14}$C]cholesterol was added as described in FIG. 1. Culture media were then harvested at 0, 6, 12, and 24 hrs and radioactivity quantified (A). Bile acid synthesis rates (B and C) were measured as the conversion of [$^{14}$C]cholesterol into methanol/water extractable counts as described in (9).

Nuclear Oxysterol Derivatives From Primary Rat Hepatocytes Overexpressing StarD1 Increase Cholesterol Uptake and Bile Acid Synthesis To examine the function of the newly characterized nuclear oxysterol derivative in cholesterol homeostasis, the effects of the purified oxysterol on cholesterol uptake and bile acid synthesis were determined by measurement of cholesterol and conversion of [$^{14}$C]cholesterol into methanol/water-extractable [$^{14}$C]products in primary rat hepatocytes. The rate of cholesterol uptake was slightly higher in cells treated with nuclear extracts extracted from StarD1 overexpressing cells than those in hepatocytes treated with nuclear extracts isolated from CYP7A1 overexpressing cells or from control cells (data not shown). Similarly, rates of bile acid synthesis were significantly higher in hepatocytes treated with nuclear extracts from StarD1 overexpressing cells, and increased by 4-fold at 24 hrs after addition of the nuclear extracts. In contrast, nuclear extracts from CYP7A1 overexpressing cells did not significantly change bile acid synthetic rates compared with control nuclear extracts (FIG. 9A). To further confirm the role of the nuclear oxysterol derivatives in bile acid biosynthesis, the purified oxysterol derivative was dissolved in nuclear extracts (methanol/water phase) from cells infected with the control virus and added to primary rat hepatocytes. The results were very similar to those in cells directly treated with the nuclear extracts from the StarD1 overexpressing cells and in a time- and concentration-dependent manner (FIG. 9B), providing evidence that the nuclear oxysterol is a potent regulator of bile acid synthesis.

Discussion

Evidence for the first time to identify a novel nuclear regulatory oxysterol derivative, which is generated in mitochondria, translocated to the nucleus, and upregulates bile acid synthesis, gives rise to a new hypothesis that a new regulatory transduction pathway may play an important role in maintenance of intracellular cholesterol homeostasis.

Figure 11:
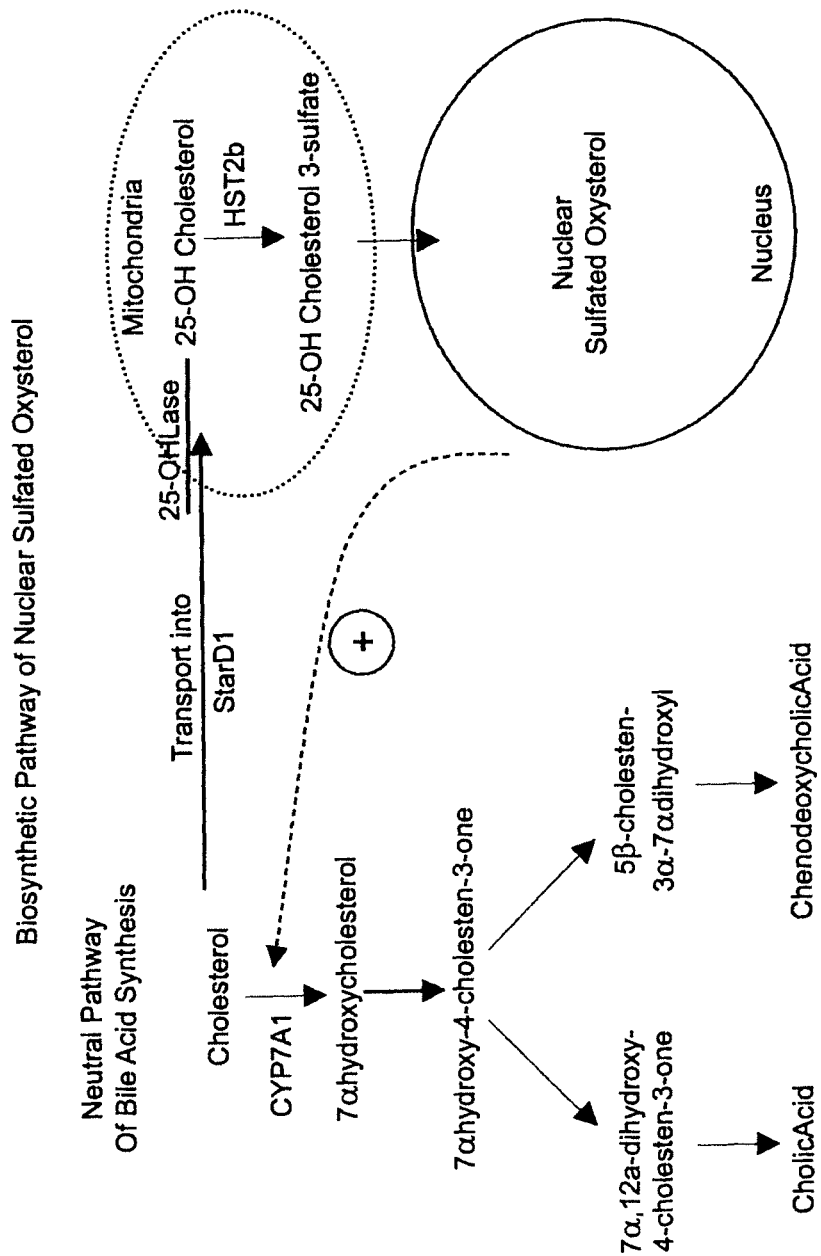
FIG. 11. Biosynthesis pathway of nuclear sulfated oxysterol. In the presence of StarD1 protein, cholesterol is delivered into mitochondria where 25-hydroxylase (25-OHLase) and hydroxylcholesterol sulfate transferase 2b (HST2b) locate, and converted to be 25-hydroxycholesterol 3-sulfate. This sulfated oxysterol translocates to nucleus and regulates gene expressions involved in cholesterol metabolism.

The present results suggested that mitochondrial cholesterol transport proteins, such as StarD1, could serve as sensors of intracellular cholesterol levels. When cholesterol levels increase, StarD1 proteins deliver cholesterol into mitochondria where it is metabolized to 25-OH cholesterol 3-sulfate (the nuclear sulfated oxysterol). The generated nuclear oxysterol derivative is then translocated into the nucleus probably by binding and activating the nuclear oxysterol receptor(s). Without being bound by theory, it appears plausible that the nuclear sulfated oxysterol-nuclear receptor(s) complex may enter into the nuclei and regulate gene expression involved in cholesterol metabolism. A possible mechanism is proposed in FIG. 11.

25-Hydroxycholsterol 3-Sulfate May be a Potential Authentic Ligand of Nuclear Sterol Receptor(s)

Figure 9B:
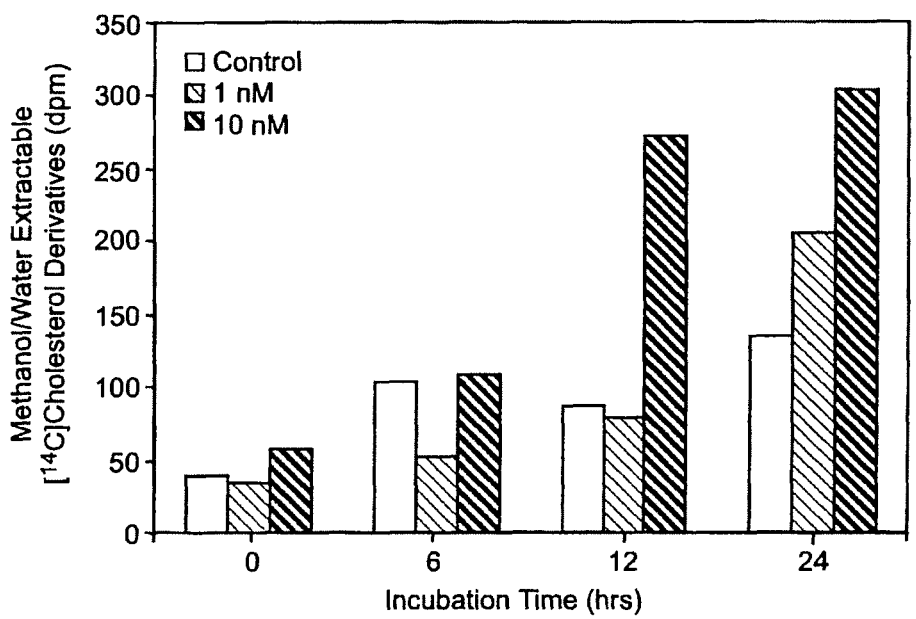
Figure 10:
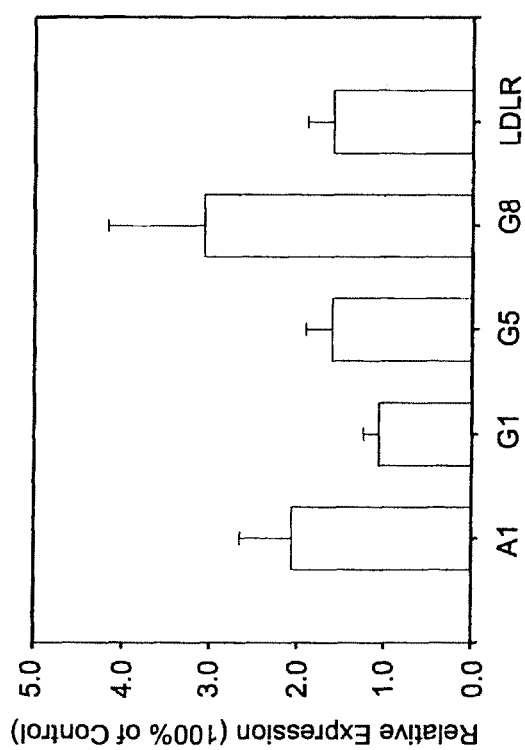
FIG. 10. ABCA1 (A1), ABCG1 (G1), LDL receptor (LDLR), ABCGS (G5), and ABCG8 (G8) gene expression in primary mouse hepatocytes following addition of the purified nuclear oxysterol. At 24 hrs following the addition, cells were harvested and total RNAs were extracted and gene expression levels were quantitated by real time RT-PCR. β-Actin mRNA was used as total mRNA internal standard. The gene expression levels in cells with StarD1 overexpression were compared with those in control cells. Ten μg of total RNA was used for cDNA preparation (RT) and 10 ng of cDNA was used for PCR. The expression levels were normalized to β-actin.

In the presence of StarD1 protein, cholesterol enters the mitochondria where it is oxidized to 25-hydroxycholesterol and is then sulfated to the nuclear sulfated oxysterol. The present results showed that both 25-hydroxycholesterol and 25-hydroxycholesterol 3-sulfate entered the nucleus. To date, 25-hydroxycholesterol has been believed to be the most potent regulator of gene transcription (21-23). To identify which one exhibits a more potent regulatory function, 25-hydroxycholesterol and 25-hydroxycholesterol 3-sulfate in nuclear extracts were separated by Folch partitioning: 25-hydroxycholesterol partitions to the chloroform phase and 25-hydroxycholesterol 3-sulfate partitions to the methanol/water phase. Interestingly, addition of the chloroform phase extracts containing 25-hydroxycholesterol to cells slightly increased the rates of bile acid synthesis (data not shown). However, the addition of methanol phase extracts dramatically increased bile acid synthesis (FIGS. 9A and 9B). Moreover, 25-hydroxycholesterol 3-sulfate is a water-soluble compound. It is thus reasonable to propose that 25-hydroxycholesterol 3-sulfate serves as a potent nuclear sterol regulators in vivo.

25-Hydroxylases (25-OHLase) and Hydroxycholesterol Sulfotransferase 2 (HST2) May be Involved in the Generation of the Potent Nuclear Sulfated Oxysterol StarD1 delivers cholesterol into the mitochondria and generates a novel nuclear sulfated oxysterol, 25-hydroxycholesterol 3-sulphate. This data suggests that a new pathway of cholesterol metabolism is responsible for generating this nuclear oxysterol. Our present report shows the presence of 25-hydroxycholesterol 3-sulfate in both the mitochondria and the nucleus but not in culture media, suggesting that 25-hydroxycholesterol 3-sulfate is generated in mitochondria and translocates exclusively to the nucleus. To biosynthesize this potent nuclear sterol regulator, two reactions should be involved: 25-hydroxylation and 3β-sulfation of cholesterol. It is not clear at this time whether 25-hydroxylation is catalyzed by CYP27A1 or 25-hydroxylase because 25-hydroxylase has not yet been identified in hepatocytes or in mitochondria, although it has been cloned (19). Since we did not see any cholesterol-3β-sulfate in the HPLC elution profile, we believe the first step is likely to be 25-hydroxylation of cholesterol catalyzed by 25-hydroxylase to form 25-hydroxycholesterol. Subsequently, sulfation of 25-hydroxycholesterol at the 3β position, is catalyzed by hydroxycholesterol sulfotransferases HST2(a, b), enzymes which have recently been cloned and identified (24;25). In addition, 25-hydroxycholesterol 3-sulfate may be glucuronidated for further catabolism and secretion via the bile as 24-hydroxycholesterol 3-sulfate (26) . However, at the present time it is not clear that the [$^{14}$C]-cholesterol derivative with a retention time of 5 min is the glucuronidation product of 25-hydroxycholesterol 3-sulfate (FIGS. 5A-5I and 6A-6F).

Steroid sulfate conjugates may play an important role in the maintenance of cholesterol homeostasis. An interesting development in recent years has been the realization that steroid sulfoconjugates play important roles in well-characterized biological effects, such as serving as potent neuro-excitatory agents, which are distinct from the well-known role of unconjugated steroids as ligands for nuclear receptors to regulate gene expression (27). Several sulfated sterols have been reported to be widely distributed in steroidogenesis tissues (26) and to circulate in plasma at concentrations ranging from 328-924 μg/100 ml, with a blood production rate of 35-163 mg/day (28). A similar sulfated oxysterol derivative, 24-hydroxycholeterol 3-sulfate 24-glucuronide (based on MS/MS analysis) was reported to be in the serum and urine of children with severe cholestatic liver diseases (26). The 3-sulfate of 24-hydroxycholesterol is the major hydroxycholesterol sulfate found in meconium and infant feces (29;30), and is most likely excreted via bile. Bile excretion of this oxysterol would be impaired in cholestasis, leading to its increased concentration of 24-hydroxycholesterol 3-sulfate in hepatocytes and conceivably leading to its glucuronidation. However, where the compound came from and what function this oxysterol plays in the cholestatic liver is still a mystery. Although high levels of the double conjugate of 24-hydroxycholesterol are an indicator of grave liver disease, and can be used as a criterion for recommending liver transplantation, the physiological role and metabolism of this compound have never been identified. Sulfated sterols have been implicated in a wide variety of biological processes, e.g. regulation of cholesterol synthesis, sperm capacitation, thrombin and plasmin activities, and activation of protein kinase C isozymes (24). Furthermore, sulfated sterols can serve as a substrate for adrenal and ovarian steroidogenesis (31;32). Sulfated sterols play an important, but unclear, role in the normal development and physiology of skin, where an epidermal sterol sulfate cycle has been described (24). The present results show that the nuclear extract containing the sulfated oxysterol and the purified nuclear sulfated oxysterol dramatically increased the rates of bile acid synthesis, strongly suggesting that the nuclear sulfated oxysterol may play an important role in cholesterol metabolism.

Activation of LXRs by oxysterols is believed to be responsible for regulation of the metabolism of several important lipids, including cholesterol and bile acids (33). The identification of an LXR response element in the promoter of the rat cholesterol CYP7A1 suggested that LXRs play an important role in the regulation of cholesterol homeostasis(34;35). LXRα-deficient mice (LXRα-/-) dysregulate the CYP7A1 gene and several other important lipid-associated genes (3). Studies utilizing these animals confirmed the essential function of LXRα as a major sensor of dietary cholesterol and an activator of the bile acid synthetic pathway in mice. The finding of authentic oxysterol ligands for LXRs is one of the most important investigative methods for developing new therapeutic methods for the prevention and treatment of hyperlipidemia and atherosclerosis. To date, there is still only indirect evidence of the important role of oxysterols, such as 24-, 25-, or 27-hydroxycholesterol, as authentic ligands in the normal regulation of cholesterol homeostasis. Soluble and nuclear oxysterol-binding proteins with a high affinity for oxysterols exist, but the physiological ligands for these proteins have not yet been defined with certainty (36). The present report, with evidence showing that a potent regulatory nuclear sulfated oxysterol that is generated in the mitochondria translocates into the nucleus, provides a new clue regarding the role of oxysterol(s) in the regulation of intracellular cholesterol homeostasis. It is reasonable to hypothesize that the regulatory nuclear sulfated oxysterol generated in mitochondria translocates into nucleus, activates nuclear oxysterol receptor(s), and up-regulates bile acid synthesis. The nuclear sulfated oxysterol serves as a ligand of nuclear sterol receptor(s).

REFERENCES FOR EXAMPLE 1

1. Russell, D. W. (2003) Annu. Rev. Biochem. 72, 137-174
2. Hylemon, P. B., Gurley, E. C., Stravitz, R. T., Litz, J. S., Pandak, W. M., Chiang, J. Y., and Vlahcevic, Z. R. (1992) J. Biol. Chem. 267, 16866-16871
3. Chiang, J. Y., Kimmel, R., and Stroup, D. (2001) Gene 262, 257-265
4. Saucier, S. E., Kandutsch, A. A., Taylor, F. R., Spencer, T. A., Phirwa, S., and Gayen, A. K. (1985) J. Biol. Chem. 260, 14571-14579
5. Schroepfer, G. J., Jr. (2000) Physiol Rev. 80, 361-554
6. Szanto, A., Benko, S., Szatmari, I., Balint, B. L., Furtos, I., Ruhl, R., Molnar, S., Csiba, L., Garuti, R., Calandra, S., Larsson, H., Diczfalusy, U., and Nagy, L. (2004) Mol. Cell Biol. 24, 8154-8166
7. Dubrac, S., Lear, S. R., Ananthanarayanan, M., Balasubramaniyan, N., Bollineni, J., Shefer, S., Hyogo, H., Cohen, D. E., Blanche, P. J., Krauss, R. M., Batta, A. K., Salen, G., Suchy, F. J., Maeda, N., and Erickson, S. K. (2005) J. Lipid Res. 46, 76-85
8. Fu, X., Menke, J. G., Chen, Y., Zhou, G., Macnaul, K. L., Wright, S. D., Sparrow, C. P., and Lund, E. G. (2001) J. Biol. Chem. 276, 38378-38387
9. Bjorkhem, I. (2002) J. Clin. Invest 110, 725-730
10. Pandak, W. M., Ren, S., Marques, D., Hall, E., Redford, K., Mallonee, D., Bohdan, P., Heuman, D., Gil, G., and Hylemon, P. (2002) J. Biol. Chem. 277, 48158-48164
11. Ren, S., Hylemon, P. B., Marques, D., Gurley, E., Bodhan, P., Hall, E., Redford, K., Gil, G., and Pandak, W. M. (2004) Hepatology 40, 910-917
12. Hall, E. A., Ren, S., Hylemon, P. B., Rodriguez-Agudo, D., Redford, K., Marques, D., Kang, D., Gil, G., and Pandak, W. M. (2005) Biochim. Biophys. Acta 1733, 111-119
13. Rodriguez-Agudo, D., Ren, S., Hylemon, P. B., Redford, K., Natarajan, R., Del Castillo, A., Gil, G., and Pandak, W. M. (2005) J. Lipid Res. 46, 1615-1623
14. Pandak, W. M., Schwarz, C., Hylemon, P. B., Mallonee, D., Valerie, K., Heuman, D. M., Fisher, R. A., Redford, K., and Vlahcevic, Z. R. (2001) Am. J. Physiol Gastrointest. Liver Physiol 281, G878-G889
15. Ren, S., Marques, D., Redford, K., Hylemon, P. B., Gil, G., Vlahcevic, Z. R., and Pandak, W. M. (2003) Metabolism 52, 636-642
16. Pandak, W. M., Bohdan, P., Franklund, C., Mallonee, D. H., Eggertsen, G., Bjorkhem, I., Gil, G., Vlahcevic, Z. R., and Hylemon, P. B. (2001) Gastroenterology 120, 1801-1809

17. Dignam, J. D., Lebovitz, R. M., and Roeder, R. G. (1983) Nucleic Acids Res. 11, 1475-1489
18. Ren, S., Hylemon, P., Marques, D., Hall, E., Redford, K., Gil, G., and Pandak, W. M. (2004) J. Lipid Res. 45, 2123-2131
19. Lund, E. G., Kerr, T. A., Sakai, J., Li, W. P., and Russell, D. W. (1998) J. Biol. Chem. 273, 34316-34327
20. Lemonde, H. A., Johnson, A. W., and Clayton, P. T. (1999) Rapid Commun. Mass Spectrom. 13, 1159-1164
21. Kandutsch, A. A., Taylor, F. R., and Shown, E. P. (1984) J. Biol. Chem. 259, 12388-12397
22. Lehmann, J. M., Kliewer, S. A., Moore, L. B., Smith-Oliver, T. A., Oliver, B. B., Su, J. L., Sundseth, S. S., Winegar, D. A., Blanchard, D. E., Spencer, T. A., and Willson, T. M. (1997) J. Biol. Chem. 272, 3137-3140
23. Peet, D. J., Turley, S. D., Ma, W., Janowski, B. A., Lobaccaro, J. M., Hammer, R. E., and Mangelsdorf, D. J. (1998) Cell 93, 693-704
24. Javitt, N. B., Lee, Y. C., Shimizu, C., Fuda, H., and Strott, C. A. (2001) Endocrinology 142, 2978-2984
25. Her, C., Wood, T. C., Eichler, E. E., Mohrenweiser, H. W., Ramagli, L. S., Siciliano, M. J., and Weinshilboum, R. M. (1998) Genomics 53, 284-295
26. Meng, L. J., Griffiths, W. J., Nazer, H., Yang, Y., and Sjovall, J. (1997) J. Lipid Res. 38, 926-934
27. Paul, S. M. and Purdy, R. H. (1992) FASEB J. 6, 2311-2322
28. Gurpide, E., Roberts, K. D., Welch, M. T., Bandy, L., and Lieberman, S. (1966) Biochemistry 5, 3352-3362
29. Montelius, J., Gustafsson, J. A., Ingelman-Sundberg, M., and Rydstrom, J. (1977) Biochim. Biophys. Acta 488, 502-511
30. Gustafsson, J. A. and Sjovall, J. (1969) Eur. J. Biochem. 8, 467-472
31. Korte, K., Hemsell, P. G., and Mason, J. I. (1982) J. Clin. Endocrinol. Metab 55, 671-675
32. Tuckey, R. C. (1990) J. Steroid Biochem. Mol. Biol. 37, 121-127
33. Komuves, L. G., Schmuth, M., Fowler, A. J., Elias, P. M., Hanley, K., Man, M. Q., Moser, A. H., Lobaccaro, J. M., Williams, M. L., Mangelsdorf, D. J., and Feingold, K. R. (2002) J. Invest Dermatol. 118, 25-34
34. Edwards, P. A., Kennedy, M. A., and Mak, P. A. (2002) Vascul. Pharmacol. 38, 249-256
35. Peet, D. J., Janowski, B. A., and Mangelsdorf, D. J. (1998) Curr. Opin. Genet. Dev. 8, 571-575
36. Bjorkhem, I. and Diczfalusy, U. (2002) Arterioscler. Thromb. Vasc. Biol. 22, 734-742

Example 2

Demonstration of Up-Regulation of LXR Targeting Gene Expression

Preliminary experiments have shown that the purified nuclear oxysterol up-regulates bile acid synthesis. To further investigate the mechanism of this activity, the effect of purified 5-cholesten-3β, 25-diol 3-sulphate on gene expression of LXR-targeted cholesterol transport proteins ABCA1, ABCG1, ABCGS, ABCG8, and LDLR was investigated. Purified nuclear sulfated oxysterol was added to primary hepatocytes in culture, and mRNA levels of the transport proteins were quantitated by real time RT-PCR. The primer sets and TagMan probes for detection of mRNA levels were purchased from AB Applied Biosystem (Foster City, Calif.) and the reactions were performed on an MJ Research DNA Engine Opticon instrument. The results are presented in FIGS. 12A and 12B and show that the addition of purified nuclear oxysterol to primary hepatocytes in culture increased expression of ABCA1 (2-fold) and ABCGS (1.6-fold), and ABCG8 (3 fold). The expression of ABCG1 is typically low in primary hepatocytes and did not change compared with control cells. The correlation of increased levels of the sulfated oxysterol in nuclei with increased levels of LXR targeting gene expression suggests that the nuclear oxysterol receptor, LXR, is activated by exposure to the sulfated oxysterol. These data do not rule out the activation of other nuclear receptor(s) as well.

Example 3

Synthesis of 5-cholesten-3β, 25-diol 3-sulphate

Figure 12A:
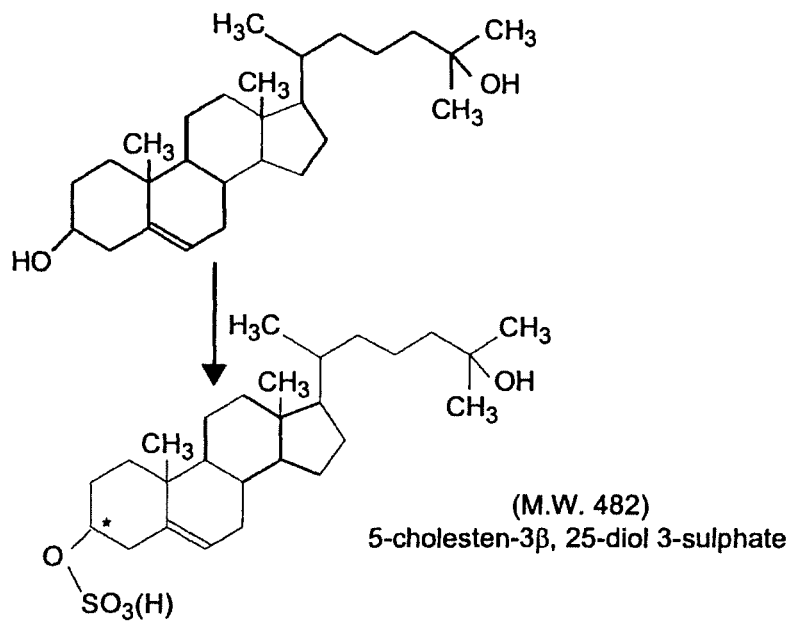
FIGS. 12A-12D.
Figure 12B:
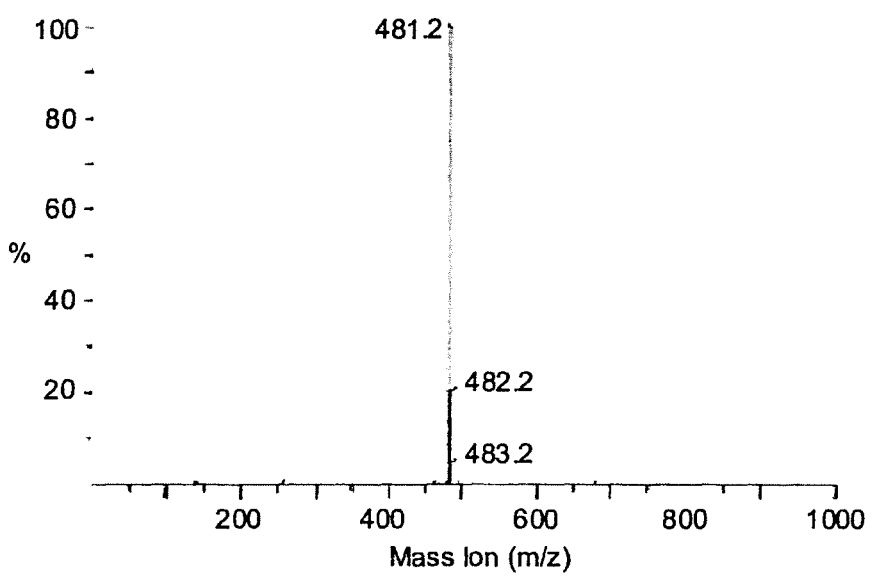

FIG. 12A shows a schematic illustration of the synthesis of the novel sulfated oxysterol of the invention by addition of a sulfate group to the 3β-position of 25-hydroxycholesterol. Synthesis was carried out as follows: A mixture of 25-hydroxycholesterol (0.1 mmol) and sulfur trioxide tri-ethyl amine complex (0.12 mmol) in dry toluene was heated to 60 degree for 24 hours under nitrogen, then cooled and the solvent was evaporated under reduced pressure. The residue was purified by flash chromatography to afford the product as a white solid using the method of described above. FIG. 12B shows the mass spectrophotometric analysis of the HPLC purified product, which suggests that the sulfate group has been successfully added to 25-hydroxycholesterol.

Figure 12C:
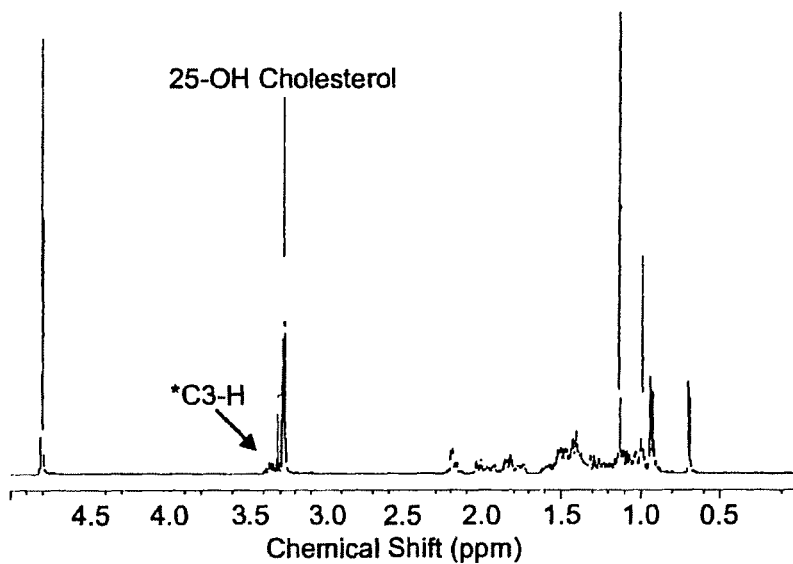
Figure 12D:
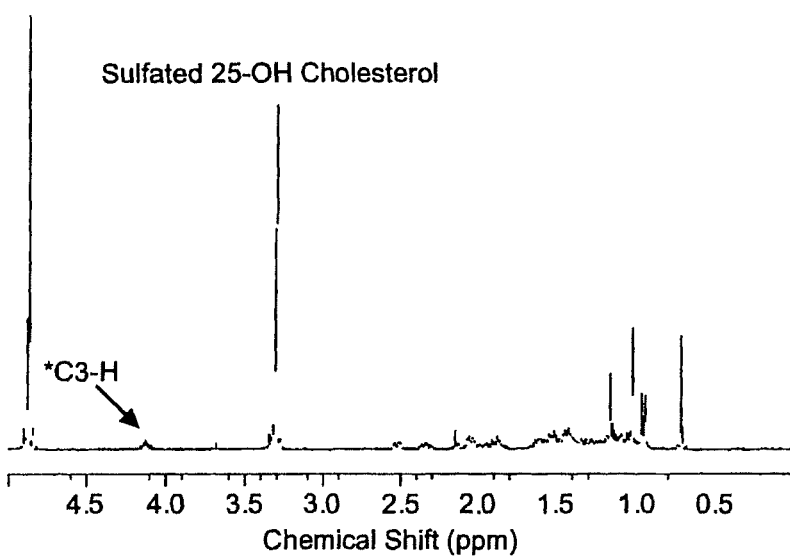

FIGS. 12C and 12D show NMR data for the starting material, 25-hydroxycholesterol, and product, respectively. As can be seen, the resonance of C3 in the molecule has been shifted from 3.35 ppm in the original compound to 4.12 ppm in the product, suggesting that the desired product, 3β-sulfated 25-hydroxycholesterol, has been formed.

Example 4

A Nuclear Oxysterol, 25HC3S, Decreases Cholesterol Synthesis via Inhibition of SREBP-1 Activation in Hepatocytes Abstract Recently, a novel oxysterol, 5-cholesten-3β, 25-diol 3-sulfate (25HC3S) was discovered, characterized, and identified in mitochondria and nuclei of primary hepatocytes following overexpression of the cholesterol transport protein, StarD1. This oxysterol was also detected in human liver nuclei. In the present study, 25HC3S was chemically synthesized. Addition of varying concentrations of 25HC3S to HepG2 cells markedly inhibited cholesterol biosynthesis and significantly decreased microsomal cholesterol. Real time RT-PCR and Western blot analysis shows that 25HC3S strongly decreased HMG CoA reductase mRNA levels in HepG2 cells and primary human hepatocytes. In comparison, 25-hydroxycholesterol (25HC) inhibited HMG CoA reductase mRNA levels in HepG2 cells but not in primary human hepatocytes when the cells were culture in serum-free media. Coincidently, 25HC3S inhibited the activation of steroid response element binding protein (SREBP-1) in absence or presence of mevinolin and mevalonate, indicating that cholesterol biosynthesis inhibition occurred through blocking SREBP-1 activation, and subsequently the expression of HMG CoA reductase in the human hepatocytes. In conclusion, the presented findings indicate that 25HC3S regulates intracellular cholesterol biosynthesis via inhibiting SREBPs activation in human hepatocytes.

Introduction

The "acidic" pathway of bile acid biosynthesis is initiated by the mitochondrial enzyme sterol 27-hydroxylase (CYP27A1). Oxysterol intermediates of the "acidic" pathway such as 27-hydroxycholesterol (27HC) and 25-hydroxycholesterol (25HC) have been shown to be regulators of cholesterol homeostasis (1;2). These oxysterols represent regulatory molecules for the expression of many other genes encoding enzymes involved in cholesterol biosynthesis and transport (3-5). In theory, increased CYP27A1 activity in peripheral tissues could both down-regulate cholesterol synthesis through generating regulatory oxysterols and the steroid response element binding proteins (SREBPs) pathway, and enhance the cellular efflux of cholesterol, i.e. its elimination, via liver oxysterol receptor, LXR (6). However, the relationship between the CYP27A1 activity and intracellular cholesterol metabolism is unknown.

Previous reports showed that overexpression of the steroidogenic acute regulatory protein (StarD1), a protein which facilitates cholesterol transport into mitochondria, dramatically increases cholesterol catabolism to bile acids both in primary hepatocytes in culture and in vivo (7;8). These findings suggest that cholesterol delivery to the mitochondria, where the enzyme CYP27A1 is localized, is the rate-determining step for bile acid synthesis via the "acidic" pathway. Subsequently, StarD1 was detected in hepatocytes (9). Overexpression of StarD1 in vivo not only increases bile acid synthesis to the same level as overexpression of CYP7A1, but also produces a similar composition of bile acids in bile (8). As described in Examples 1-3, a novel oxysterol, 5-cholesten-3β, 25-diol 3-sulfate (25HC3S) was found and characterized in mitochondria and nuclei of primary hepatocytes following overexpression of StarD1. This oxysterol was also present in human liver nuclei (10). The results suggested that the oxysterol is synthesized in the mitochondria and tranlocated to the nuclei. Oysteorls in nuclei should be able to play important roles in maintenance of intracellular cholesterol homeostasis. However, the function of this nuclear oxysterol, 25HC3S, remains unknown.

In the present study, we chemically synthesized 25HC3S and presented evidence that this oxysterol strongly regulates HMG CoA reductase, a key enzyme in cholesterol biosynthesis via SREBP regulatory system in hepatocytes.

Materials and Methods

Materials: Cell culture reagents and supplies were purchased from GIBCO BRL (Grand Island, N.Y.); [$^{14}$C]Cholesterol and [$^3$H]25-hydroxycholesterol ([$^3$H]25HC) from New England Nuclear (Boston, Mass.). [$^{14}$C]27-OH Cholesterol was prepared as previously described (11). HepG2 cells were obtained from American Type Culture Collection (Rockville, Md.). Fetal bovine serum was obtained from Bio Whittaker (Walkersville, Md.). Tissue culture flasks were purchased from Costar Corp. (Cambridge, Mass.). The reagents for real time RT-PCR were from AB Applied Biosystem (Warrington WA1 4 SR, UK). The chemicals used in this research were obtained from Sigma Chemical Co. (St. Louis, Mo.) or Bio-Rad laboratories (Hercules, Calif.) unless otherwise specified. All solvents were obtained from Fisher (Fair Lawn, N.J.) unless otherwise indicated. The enhanced chemilluminescence (ECL) reagents were purchased from Amersham Biosciences (Piscataway, N.J.). The testosterone and 27HC were obtained from Research Plus Inc. (Bayonne, N.J.). LK6 20×20 cm thin layer chromatography (TLC) plates were purchased from Whatman Inc. (Clifton, N.J.). Nylon membranes were purchased from Micron Separation Inc. (Westborough, Mass.).

Chemical Synthesis of 5-cholesten-3β, 25-diol 3-sulfate

A mixture of 25HC (402 mg, 1 mmol) and triethylamine-sulfur trioxide pyridine complex (160 mg, 1 mmol) in 5 ml of dry pyridine was stirred at room temperature for 2 hrs. After the solvent was evaporated at reduced pressure, the products were purified by HPLC using silica gel column and solvent of methylene chloride and methanol (5%) as mobile phase to afford the product as a white solid powder. The structure of the product was characterized by mass spectrum (MS) and nuclear magnetic resonance (NMR) spectroscopy analysis.

Mass Spectral Analysis

The synthesized compound was analyzed by a MDS Sciex ABI 4000 Triple Quadrapole Mass Spectrometer (MDS Sciex, Toronto, Canada) with a Turbo IonSpray ionization (ESI) source and the mass spectrometer was operated in negative ion modes and data were acquired using full scan mode as previously described (10).

Proton Nuclear Magnetic Resonance Spectroscopy

Samples were prepared for $^1$H NMR analysis as described previously (12). Briefly, each sample, 1 mg, was dissolved in 0.5 ml of D$_2$O and lyophilized to remove exchangeable protons. The residue was dissolved in 0.5 ml of dimethyl sulfoxide-d6/D$_2$O (98:2, v/v). NMR spectra were obtained on spectrometers operating at $^1$H frequencies of 300 MHz.

Cell Culture

HepG2 cells were grown in MEM containing non-essential amino acids, 0.03 M NaHCO$_3$, 10% FBS, 1 mM L-glutamine, 1 mM sodium pyruvate and 1% Pen/Strep and incubated at 37° C. in 5% CO$_2$. When cells reached at ~90% confluency, the oxysterols in DMSO or in ethanol (final concentration, 0.1%) and/or [1-$^{14}$C]acetate for cholesterol synthesis was added or otherwise as indicated. Microsomal and cytosol fractions were isolated from broken cells as described previously (10).

Primary human hepatocytes were purchased from an NIH-approved facility (Liver Tissue Procurement Distribution System, Univ. of Minnesota). Cells were obtained from a random sampling of males and females 18-69 yr of age. Experiments were performed as cells became available to corroborate findings in experiments conducted in HepG2 cells as previous described (13).

Determination of Cholesterol Biosynthesis by TLC and HPLC

After incubation of HepG2 cells with media containing 25HC3S for 6 hrs, cultures in 25-cm2 flasks were given 3 ml of the same fresh medium containing 5 µCi of the [1-$^{14}$C] acetate. After 4 hr incubation at 37° C., the media were removed and the cells were washed twice with phosphate-saline buffer (PBS), harvested with rubber police as described, and collected in Eppendoff tubes. The cells were sedimented by centrifugation and the pellets were washed three times by resuspension and sedimentation. The pellets were resuspended in 0.3 ml of PBS. The total lipids were extracted and separated by adding 3 volume of chloroform: methanol (v/v, 1:1). [$^{14}$C]Cholesterol and 27-hydroxycholesterol was isolated into chloroform phase and separated on TLC (tuluene:acetyl acetate, 2/3, v/v/). [1-$^{14}$C]acetate derivatives were visualized by Image Reader, Fujifilm BAS-1800 II.

HPLC Analysis of Cholesterol Derivatives

[1-$^{14}$C]Acetate derivatives in the chloroform phase were analyzed by HPLC on an Ultrasphere Silica column (5 µx4.6 mmx25 cm; Backman, USA) using HP Series 1100 solvent delivery system (Hewlett Packard) at 1.3 ml/min flow rate. The column was equilibrated and run in a solvent system of hexane:isopropanol:glacial acetic acid (965:25:10, v/v/v), as the mobile phase. The effluents were collected every 0.5 min (0.65 ml per fraction) except as indicated. The counts in [$^{14}$C]acetate derivatives were determined by Scintillation Counting. The column was calibrated with [$^{14}$C]cholesterol, [$^{3}$H]25HC, and [$^{14}$C]27-hydroxycholesterol.

Determination of HMG CoA Reductase mRNA by Real-Time RT-PCR

Total RNA was isolated from HepG2 cells using SV Total RNA Isolation Kit (Promega). Two µg of total RNA was used for first-strand cDNA synthesis as recommended by manufacture (Invitrogen). Real-time PCR was performed using SYBR Green on ABI 7500 Fast Real-Time PCR System (Applied Biosystems). The final reaction mixture contained 5 ng of cDNA, 100 nM of each primer, 10 µl of 2x SYBR® Green PCR Master Mix (Applied Biosystems), and RNase-free water to complete the reaction mixture volume to 20 µl. All reactions were performed in triplicate. The PCR was carried out for 40 cycles at 95° C. for 15 s and 60° C. for 1 min. The fluorescence was read during the reaction, allowing a continuous monitoring of the amount of PCR product. The data was normalized to internal control-β-actin or GAPDH mRNA. The sequences of primers for HMG CoA reductase used in real-time PCR are ACCTTTC-CAGAGCAAGCACATT (SEQ ID NO: 1) (Forward) and AGGACCTAAAATTGCCATTCCA (SEQ ID NO: 2) (Reverse).

Western Blot Analysis

Microsomal proteins (80 µg) were separated on a 7.5% SDS-polyacrylamide denaturing gel according to the method of Laemmli (14). Following SDS-PAGE (Hoefer Vertical Slab Gel Unit; Heofer, San Francisco, Calif.), proteins were electrophoretically transferred overnight (4° C.) to Immobilon-P membranes using a Hoefer Trans Blot Electrophoretic Transfer cell. The membranes were then blocked for 90 minutes (25° C.) in blocking buffer (PBS, pH 7.4, 0.1% Tween, 5% non-fat dry milk). Proteins were then incubated for 90 minutes (25° C.) or overnight (4° C.) with a rabbit polyclonal IgG (1:2500-1:20,000) against human SREBP-1, SREBP-2, or HMG CoA reductase. After washing, a secondary antibody (goat anti-rabbit IgG-Horse-radish peroxidase conjugate, 1:2500) was added to the blocking solution (25° C., 90 minutes). Protein bands were detected using the Amersham ECL plus Kit.

Results

Chemical synthesis of the nuclear oxysterol, 5-cholesten-3β, 25-diol 3-Sulfate To study the role that 25HC3S may play in cellular cholesterol homeostasis, this oxysterol was chemically synthesized. Using a modified triethylamine-sulfur trioxide complex protocol as described in Methods, the nuclear oxysterol was successfully synthesized as outlined in FIG. 12A. MS analysis of the synthesized compound shows the same molecular mass ion, m/z 481 as the "authentic" nuclear oxysterol (FIG. 12B). $^{1}$H NMR analysis shows that the proton resonance at C3 with multiple small (1.5 Hz) splits near 3.65 ppm in the spectrum of 25-OH cholesterol (starting material) (FIG. 12C) is shifted to 4.20 ppm in the product spectrum (FIG. 12D) as indicated, which confirms that $HSO_3^-$ group is added at the C3 position of 25-OH cholesterol. HPLC analysis shows the same retention time of the synthesized oxysterol as the authentic nuclear oxysterol (data not shown). Combined with the results from the MS analysis, it is concluded that the synthesized molecule is 5-cholesten-3β, 25-diol 3-sulphate (25HC3S). The results also confirmed the structure of the nuclear oxysterol as previously reported (10 and Examples 1-3).

Figure 13A:
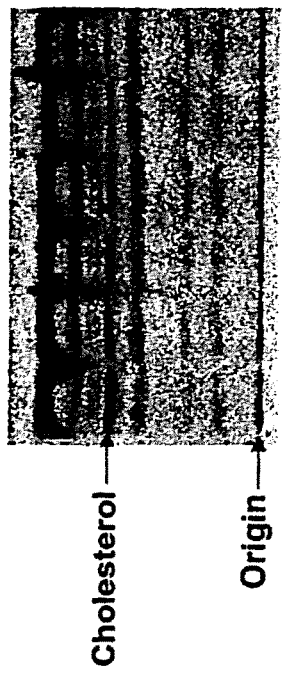
FIGS. 13A-13C. TLC and HPLC analysis of the newly synthesized [$^{14}$C]cholesterol. After incubation of the 25HC3S-treated cells with [1-$^{14}$C]acetate for 2 hrs, the cells were harvested. The total neutral lipids were extracted with chloroform/methanol and partitioned into chloroform phase. The [$^{14}$C]-acetate derivatives were analyzed by thin layer chromatography (TLC) and HPLC.
Figure 13B:
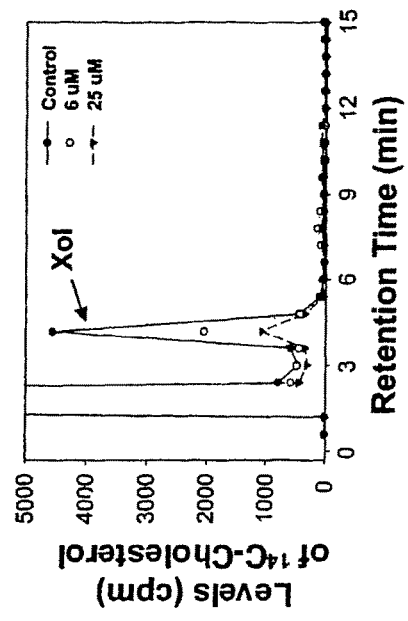
Figure 13C:
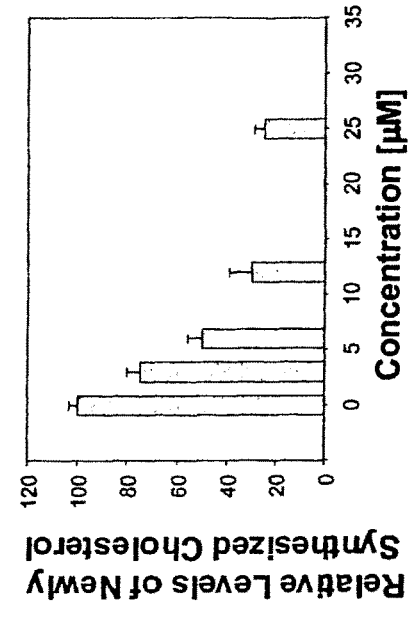

25HC3S Inhibits Cholesterol Biosynthesis and Decreases Cholesterol Levels in Microsomal Fractions To examine the effects of 25HC3S on cholesterol biosynthesis, the rates of cholesterol synthesis were determined by adding [1-$^{14}$C]acetate following the addition of varying concentration of 25HC3S to HepG2 cells in culture. FIGS. 13A-13C summarize the effects of 25HC3S on cholesterol biosynthesis. After incubation of the cells in the media containing 25HC3S for 6 hrs and [$^{14}$C]acetate for additional 4 hrs, total lipids were extracted and partitioned. Neutral lipids in the chloroform phases including [$^{14}$C]acetate derivatives were analyzed by TLC and HPLC, TLC analysis shows that [$^{14}$C]cholesterol ether, [$^{14}$C]cholesterol, and [$^{14}$C]25HC were synthesized but no detectable [$^{14}$C]27HC (FIG. 13A). Free [$^{14}$C]cholesterol was found to be significantly decreased following addition of 25HC3S while the other labeled sterols did not significantly change. The decreases were concentration dependent (FIG. 13A). The decreased amounts of [$^{14}$C]cholesterol bands on the TLC were confirmed by HPLC analysis as shown in FIG. 13B. The results from three experiments are summarized in FIG. 13C.

To study the distribution of intracellular cholesterol following the addition of 25HC3S, microsomal, nuclear, and cytosol fractions were isolated and total lipids from each fraction were extracted with chloroform/methanol/water. The cholesterol concentration in each fraction was determined by HPLC after cholesterol oxidase treatment which converts sterols to 3-oxo-β4 derivatives. As shown in FIGS. 14A-14H, 25HC3S significantly decreased cholesterol levels in the microsomal fraction (FIGS. 14A-14D) as well as 25HC (FIGS. 14E-14H) but not in cytosol and nuclear fractions (data not shown). The decreases in cholesterol concentration were dose dependent as indicated in FIGS. 14A-14H. It was also observed that no 25HC could be detected in the fractions from cells treated with 25HC3S. In contrast, dose dependent levels of 25-hydroxycholeterol could be detected in the fractions treated with 25HC as shown in FIGS. 14E-14H. These results suggest that 25HC3S directly inhibits cholesterol biosynthesis and decreases cholesterol levels in microsomal fractions and not through its degradation to be 25HC.

Figure 15A:
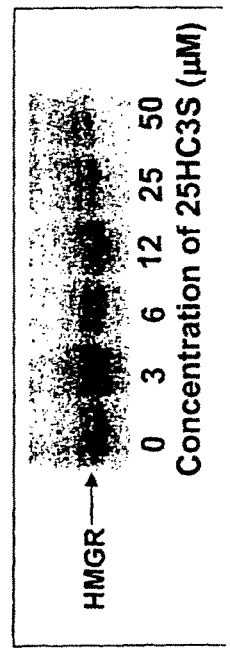
FIGS. 15A-15D. 25HC3S regulates HMGR mRNA Expression. Real time RT-PCR analysis of HMG CoA R reductase expression in HepG2 cells (FIGS. 15A and 15B). Western blot analysis of protein levels of HMG CoA reductase (FIG. 15C). Total RNAs were purified using SV Total RNA Isolation Kit (Promega) from the cells treated with 25HC3S at concentrations as indicated (FIG. 15A) and incubation at 12 μM of 25HC3S for the different times (effect on HMG CoA mRNA) (FIG. 15B). Two μg of total RNA was used for cDNA preparation (RT) and performed as manufacture recommended (Invitrogen), and 10 ng of cDNA was used for real time PCR. The expression levels were normalized to GAPDH. The total extracted protein, 100 μg, was loaded in each well for each condition as indicated in FIG. 15C. The bands of HMG CoA reductase (HMGR) were quantitated by laser density scanning. The data from three experiments were summarized in FIG. 15D. Each value represents mean of three experiments±standard derivation.
Figure 15C:
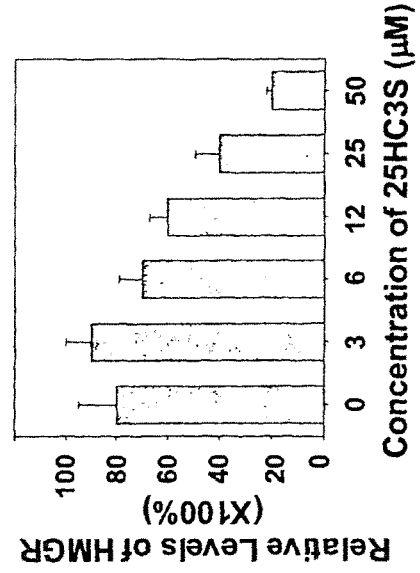
Figure 15B:
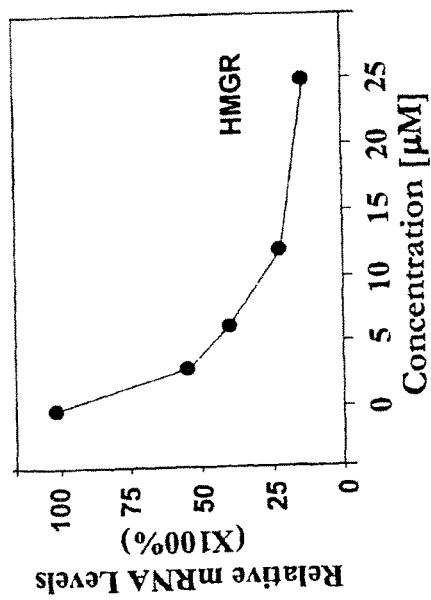
Figure 15D:
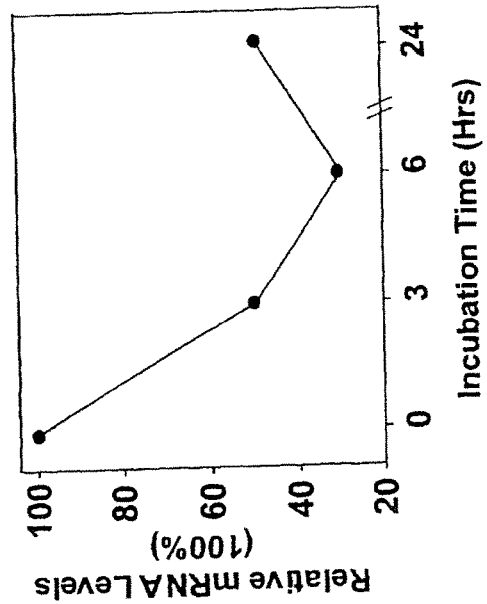

The Nuclear Oxysterol Inhibits Cholesterol Biosynthesis by Decreasing HMG CoA Reductase mRNA Levels To investigate how 25HC3S inhibits cholesterol biosynthesis, total mRNA were isolated from HepG2 cells following incubation in 10% FBS fresh media containing different concentrations of 25HC3S (FIG. 15A). The mRNA levels of HMG CoA reductase were determined by real time RT-PCR. As shown in FIG. 15A, there was concentration dependent decreases in HMG CoA reductase mRNA following the addition of 25HC3S to the cells in culture. The addition of 25HC3S to HepG2 cells also lead to a marked decrease in the levels of HMG CoA reductase protein (FIGS. 15C and D). Western blot analysis shows that 50% of its protein level was decreased in a concentration dependent following the addition of 25HC3S to culture media (FIGS. 15C and D).

Figures 16A, 16B, 16C:
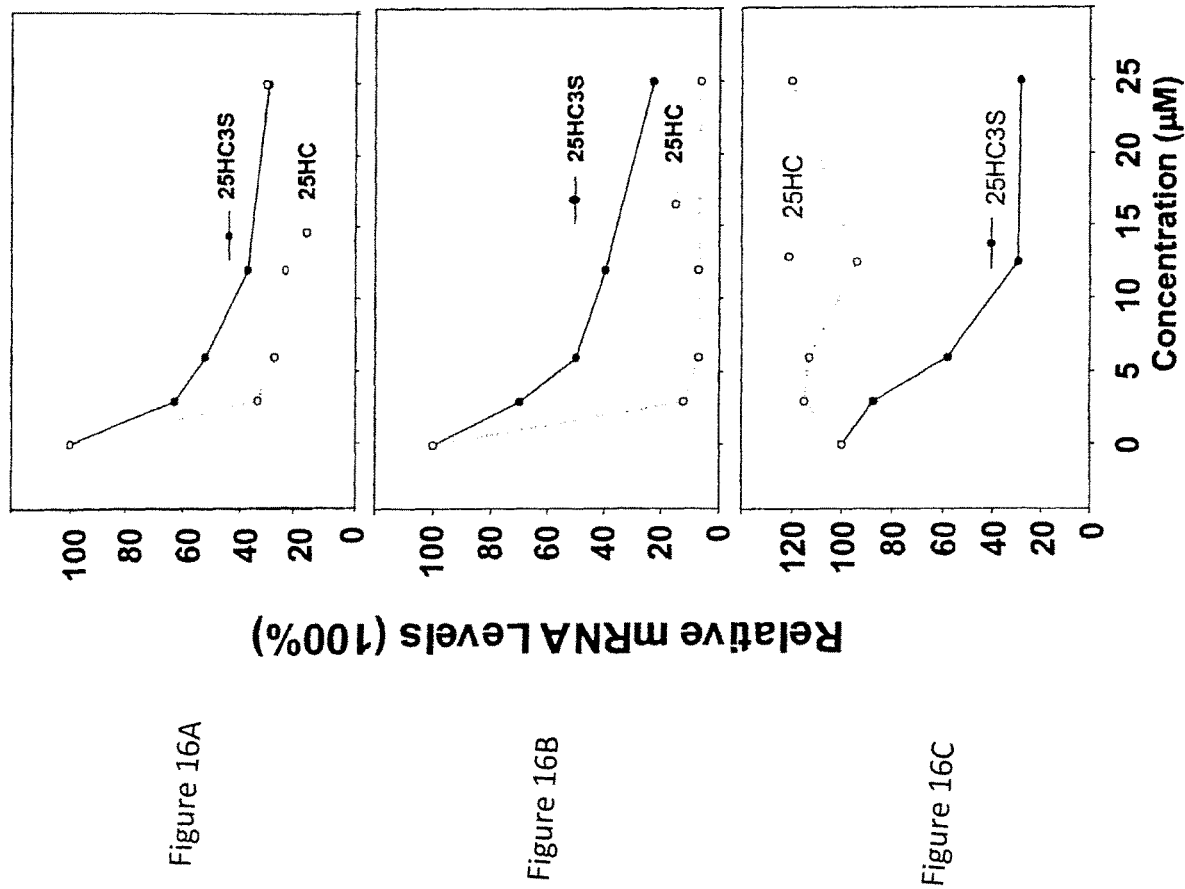
FIGS. 16A-16C. Effects of 25HC and 25HC3S on the levels of HMG CoA reductase mRNA in hepatocytes. Total RNA was extracted from the HepG2 cells cultured either in 10% FBS media (FIG. 16A) or in 10% lipid-depleted sera (FIG. 16B) and treated with either 25HC or 25HC3S as indicated. The real time RT-PCR analysis was performed as described in FIG. 16. The data represent a typical result from one of three independent experiments. The 25HC or 25HC3S affects the HMG CoA reductase expression in primary human hepatocytes (FIG. 16C). The data represent a typical result from one of three independent experiments.

To compare with 25HC, mRNA levels of HMG CoA reductase in 25HC or 25HC3S-treated HepG2 cells were analyzed by real time RT-PCR. Both of the compounds can inhibit HMG CoA reductase in a similar fashion as shown in FIG. 16A. To further distinguish whether 25HC3S inhibits HMG CoA reductase expression via lipids uptake in the culture media, HepG2 cells were incubated in media containing lipid-depleted serum for 2 hrs, which increases expression of HMG CoA reductase by four-fold as previously reported (15). Cells were incubated for another 6 hrs following the addition of 25HC3S. Real time RT-PCR analysis shows that 25HC3S still strongly inhibits HMG CoA reductase mRNA levels (FIG. 16B). Interestingly, 25HC shows much more potent inhibition of the reductase mRNA in lipid-depleted media as compared to cells cultured in medium containing FBS (FIGS. 16A and 16B). Under these conditions, 25HC is more potent inhibition than 25HC3S on HMG CoA reductase mRNA levels. The result of inhibition of HMG CoA reductase by 25HC is consistent with previous report (16;17). To confirm its physiological role that 25HC3S plays in the cholesterol biosynthesis, primary human hepatocytes (PHH) cultured in serum-free media were used. Surprisingly, 25HC did not significantly affect the levels of HMG CoA reductase mRNA (~15% at 25 mM). In contract, 25HC3S inhibited HMG CoA reductase mRNA at a similar level (~75%) as that in HepG2 cells (FIG. 16C). HPLC analysis showed that the increasing levels of 25HC in the cells are concentration dependent (FIG. 17A-E), indicating that 25HC can still enter to the cells under this culture condition as in FBS containing media. These results suggest that 25HC3S and 25HC inhibit HMG CoA reductase mRNA by different mechanisms.

The Nuclear Oxysterol Inhibits HMG CoA Reductase Expression by Inhibition of Both SREBP-1 and SREBP-2 Activation It has been well documented that HMG CoA reductase gene expression is regulated by SREBP-1 and SREBP-2 (18). When SREBPs are activated, the cholesterol biosynthesis will increase (19). To study whether SREBP regulatory system is involved in the inhibition of HMG CoA reductase mRNA levels and inhibition of cholesterol biosynthesis by 25HC3S, total cellular protein was extracted from HepG2 cells treated with 25HC3S or 25HC at different concentration (FIGS. 18A-18D). The precursor and mature forms of SREBPs were determined by Western blot analysis. As expected, the decreases of the mature forms of SREBP-1 and the increases of the precursor form of SREBP-1 following addition of 25HC3S and 25HC were dose dependent (FIGS. 18A and 18B). However, the mature form of SREBP-2 only slightly decreased (FIGS. 18A and 18B). It was observed that the activation of SREBP-1 was much more sensitive to the treatment with 25HC and 25HC3S than that of SREBP-2. The inhibition of SREBP-1 maturation fits the decrease in HMG CoA reductase mRNA, at 3 µM of 25HC or 12 µM of 25HC3S, 85% of the mRNA of HMG CoA reductase and SREBP1 was inhibited. To confirm the mechanism, HepG2 cells were incubated in media containing 50 µM of mevinolin and 0.5 µM of mevalonate. Under this condition, SREBPs and HMG CoA expressions are upregulated. Following the treatment with 25HC or 25HC3S, SREBPs activation in the cells was determined by Western blot as described above. As shown in FIGS. 18C and 8D, 25HC3S shows more potent inhibition on SREBP-1 activation than 25HC. Thus, the nuclear oxysterol, 25HC3S, is most likely to inhibit the activation of SREBP-1 and subsequently inhibits the expression HMG CoA reductase.

Discussion

The current study shows that the chemically synthesized oxysterol, 25HC3S as well as 25HC, inhibits the cholesterol biosynthesis and the expression of the key enzyme, HMG CoA reductase. Unlike 25HC, 25HC3S inhibits this expression in primary human hepatocytes as well as HepG2. 25HC3S was found in the human liver nuclei and its levels were dramatically increased following overexpression of mitochondrial cholesterol delivery protein, StarD1, in primary rat hepatocytes, indicating that 25HC3S is most likely synthesized in the mitochondria and translocated to the nuclei for the regulation of gene expression involved in cholesterol homeostasis (10). The present results provided evidence that the oxysterol, 25HC3S, plays an important role in maintenance of the intracellular cholesterol homeostasis, and suggested that the StarD1 protein may serve as a sensor of intracellular cholesterol levels. When cholesterol levels are too high in the cells, StarD1 protein may deliver cholesterol to mitochondria where cholesterol is converted to be potent regulatory oxysterols such as 25HC, 27HC, and 25HC3S. Those oxysterols play important roles in maintenance of cholesterol homeostasis.

Figure 17A:
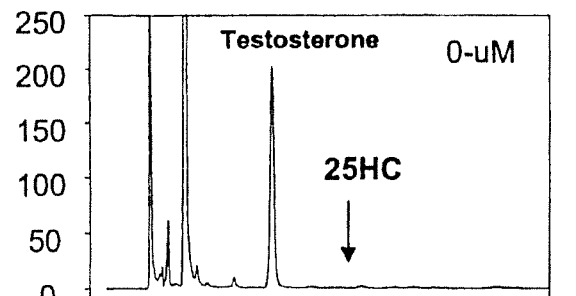
FIGS. 17A-17E. HPLC analysis of 25HC in PHH cells treated with 25HC. The total lipids were extracted from 25HC-treated PHH cells. α,β-Unsaturated ketones were generated by incubating the extracted sterols with cholesterol oxidase and were analyzed by normal phase HPLC.
Figure 17B:
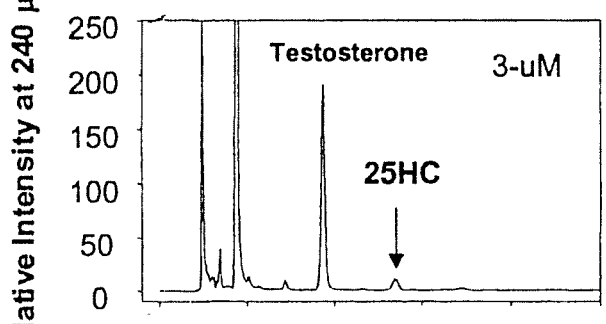
Figure 17C:
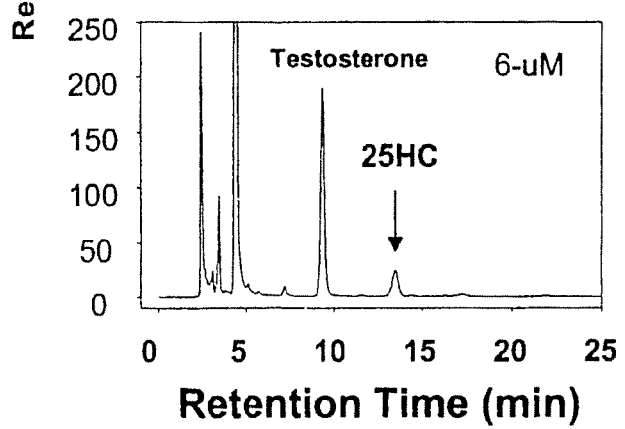
Figures 17D, 17E:
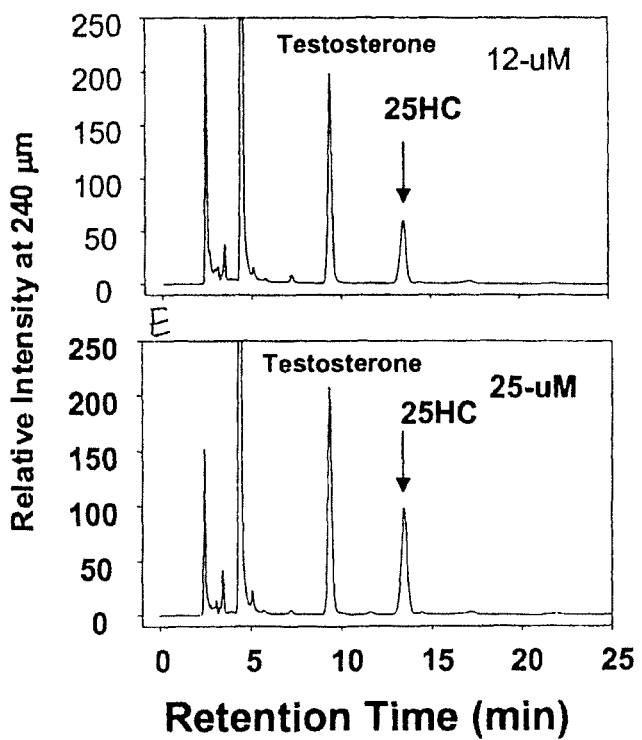

Theoretically, the added oxysterols can be metabolized after they enter into cells: 25HC can be sulfated by hydroxysteroid sulfotransferase 2B1b (SULT2B1b) to be sulfated 25HC or sulfated 25HC can be degraded by sulfatase to be 25HC. Thus, which one serves as a potent regulator in the maintenance of cholesterol homeostasis is questionable. Our HPLC analysis data shows that no 25HC was generated following addition of 25HC3S up to 50 µM (FIGS. 17A-17C) suggesting that 25HC3S was not degraded during the culture time. In contrast, the peak of 25HC increased following the addition of the 25HC and the increasing is dose dependent (FIGS. 17D and 17E). Although the results can not rule out the possibility that a small portion of the oxysterol was converted to be the sulfated 25HC, there is no evidence that 25HC works as the sulfated form at present.

25HC3S and 25HC inhibit cholesterol synthesis by two different mechanisms, both involving the proteins that control sterol regulatory element-binding proteins (SREBPs), membrane-bound transcription factors that activate genes encoding enyzymes of lipids biosynthesis. In sterol-depleted cells, SREBP cleavage-activating protein (SCAP) escorts its bound SREBP to the Golgi apparatus where the SREBP is processed sequentially by two membrane-embedded proteases. The NH$_2$-terminal domain released by the process can enter the nucleus where it activates transcription of the gene encoding HMG CoA reductase and more than 30 other genes whose products are necessary for lipid synthesis (18). When 25HC is delivered to cells in ethanol or when cholesterol is delivered in LDL, SCAP becomes trapped in the ER. The bound-SREBP is no longer carried to the Golgi apparatus, and the NH$_2$-terminal domain can not enter the nucleus (20). As a result, transcription of the lipid biosynthetic genes declines. Retention of the SCAP-SREBP complex in the ER is mediated by the sterol-induced binding of SCAP to Insigs (Insig-1 and Insig-2) in the ER membrane (20;21). When mixtures of cholesterol and 25HC are added to cultured cells, SCAP is induced to bind to Insig 1 and Insig-2, and thus can not transport SREBPs to the Golgi body (3) and to be activated. J. L. Goldstein laboratory provided evidence that cholesterol interacts with SCAP directly by inducing it to bind to Insigs, whereas 25HC works indirectly through a putative 25HC sensor protein that elicits SCAP Insig binding (3). However, what the 25HC sensor protein is unknown.

The present study showed that 25HC strongly inhibits HMG CoA reductase in the presence of the lipids depleted serum both in HepG2 (FIGS. 18A-18D) (~90%), similar inhibits as 25HS3S does in the presence of serum (~70%), but weakly inhibits in PHH when the cells were cultured in serum free media (FIGS. 17A-17E) (~15%). These results suggest that PHH does not express 25-hydroxycholsteorl sensor protein(s) under this culture system. However, 25HC3S can inhibit the enzyme expression to similar levels either presence or absence of serum or lipids depleted serum in both hepG2 and PHH indicating that 25HC3S can directly regulate the gene expression. The major reason could be that 25HC3S is much more hydrophilic than 25-hydroxycholterol and is water soluble, which makes the molecule freely self-transport after this molecule enters the cells.

The oxysterol, 25HC3S, inhibits the cholesterol biosynthesis through inhibiting the activation of SREBP-1 and SREBP-2, and subsequently inhibit the expression HMG CoA reductase in HepG2 cells and primary human hepatocytes. Based on the microarray data from transgenic and knockout mice, both SREBP-1 and SREBP-2 activation stimulate HMG CoA reductase by 30 folds and 38 folds, respectively (18). SREBP-1 also strongly stimulates fatty acid synthase but not SREBP-2 (18). However, it is not clear whether SREBP-1 and SREBP-2 are directly mediated by 25HC3S to regulate the expression regulation of the key enzyme, HMG CoA. Our results clearly show that 25HC3S as well as 25HC are much more potent in inhibiting SREBP-1 activation than SREBP-2. We believe that 25HC3S inhibits SREBP-1 activation and subsequently inhibits HMG CoA reductase resulting in the decline of cholesterol biosynthesis.

REFERENCES FOR EXAMPLE 4

1. Dubrac S, Lear S R, Ananthanarayanan M, Balasubramaniyan N, Bollineni J, Shefer S et al. Role of CYP27A in cholesterol and bile acid metabolism. J Lipid Res 2005; 46(1): 76-85.
2. Li X, Hylemon P, Pandak W M, Ren S. Enzyme activity assay for cholesterol 27-hydroxylase in mitochondria. J Lipid Res 2006; 47(7): 1507-1512.
3. Adams C M, Reitz J, De Brabander J K, Feramisco J D, Li L, Brown M S et al. Cholesterol and 25-hydroxycholesterol inhibit activation of SREBPs by different mechanisms, both involving SCAP and Insigs. J Biol Chem 2004; 279 (50): 52772-52780.
4. Bjorkhem I, Diczfalusy U. Oxysterols: friends, foes, or just fellow passengers? Arterioscler Thromb Vasc Biol 2002; 22(5): 734-742.
5. Corsini A, Verri D, Raiteri M, Quarato P, Paoletti R, Fumagalli R. Effects of 26-aminocholesterol, 27-hydroxycholesterol, and 25-hydroxycholesterol on proliferation and cholesterol homeostasis in arterial myocytes. Arterioscler Thromb Vasc Biol 1995; 15(3): 420-428.
6. Fu X, Menke J G, Chen Y, Zhou G, Macnaul K L, Wright S D et al. 27-hydroxycholesterol is an endogenous ligand for liver X receptor in cholesterol-loaded cells. J Biol Chem 2001; 276(42): 38378-38387.
7. Pandak W M, Ren S, Marques D, Hall E, Redford K, Mallonee D et al. Transport of cholesterol into mitochondria is rate-limiting for bile acid synthesis via the alternative pathway in primary rat hepatocytes. J Biol Chem 2002; 277(50): 48158-48164.
8. Ren S, Hylemon P B, Marques D, Gurley E, Bodhan P, Hall E et al. Overexpression of cholesterol transporter StAR increases in vivo rates of bile acid synthesis in the rat and mouse. Hepatology 2004; 40(4): 910-917.
9. Hall E A, Ren S, Hylemon P B, Rodriguez-Agudo D, Redford K, Marques D et al. Detection of the steroidogenic acute regulatory protein, StAR, in human liver cells. Biochim Biophys Acta 2005; 1733(2-3): 111-119.
10. Ren S, Hylemon P, Zhang Z P, Rodriguez-Agudo D, Marques D, Li X et al. Identification of a novel sulfonated oxysterol, 5-cholesten-3beta,25-diol 3-sulfonate, in hepatocyte nuclei and mitochondria. J Lipid Res 2006; 47(5): 1081-1090.
11. Rodriguez-Agudo D, Ren S, Hylemon P B, Redford K, Natarajan R, Del Castillo A et al. Human StarDS, a cytosolic StAR-related lipid binding protein. J Lipid Res 2005; 46(8): 1615-1623.
12. Ren S, Scarsdale J N, Ariga T, Zhang Y, Klein R A, Hartmann R et al. 0-acetylated gangliosides in bovine buttermilk. Characterization of 7-O-acetyl, 9-O-acetyl, and 7,9-di-O-acetyl GD3. J Biol Chem 1992; 267(18): 12632-12638.
13. Hall E A, Ren S, Hylemon P B, Rodriguez-Agudo D, Redford K, Marques D et al. Detection of the steroidogenic acute regulatory protein, StAR, in human liver cells. Biochim Biophys Acta 2005; 1733(2-3): 111-119.
14. Laemmli U K. Cleavage of structural proteins during the assembly of the head of bacteriophage T4. Nature 1970; 227(259): 680-685.
15. Hall E A, Ren S, Hylemon P B, Redford K, Del Castillo A, Gil G et al. Mitochondrial cholesterol transport: a possible target in the management of hyperlipidemia. Lipids 2005; 40(12): 1237-1244.
16. Panini S R, Sexton R C, Rudney H. Regulation of 3-hydroxy-3-methylglutaryl coenzyme A reductase by oxysterol by-products of cholesterol biosynthesis. Possible mediators of low density lipoprotein action. J Biol Chem 1984; 259(12): 7767-7771.
17. Sexton R C, Gupta A K, Panini S R, Rudney H. Progesterone stimulation of HMG-CoA reductase activity in cultured cells. Biochim Biophys Acta 1995; 1255(3): 320-332.
18. Horton J D, Shah N A, Warrington J A, Anderson N N, Park S W, Brown M S et al. Combined analysis of oligonucleotide microarray data from transgenic and knockout mice identifies direct SREBP target genes. Proc Natl Acad Sci U S A 2003; 100(21): 12027-12032.

19. Horton J D, Goldstein J L, Brown M S. SREBPs: activators of the complete program of cholesterol and fatty acid synthesis in the liver. J Clin Invest 2002; 109(9): 1125-1131.
20. Yang T, Espenshade P J, Wright M E, Yabe D, Gong Y, Aebersold R et al. Crucial step in cholesterol homeostasis: sterols promote binding of SCAP to INSIG-1, a membrane protein that facilitates retention of SREBPs in ER. Cell 2002; 110(4): 489-500.
21. Yabe D, Xia Z P, Adams C M, Rawson R B. Three mutations in sterol-sensing domain of SCAP block interaction with insig and render SREBP cleavage insensitive to sterols. Proc Natl Acad Sci U S A 2002; 99(26): 16672-16677.

Example 5

Figure 19:
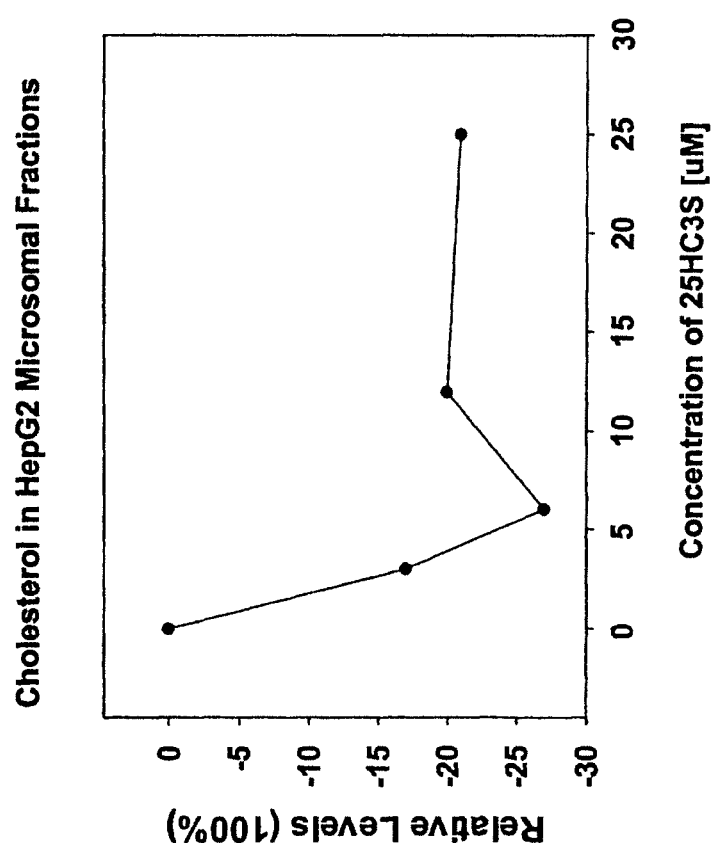
FIG. 19. Relative levels of cholesterol in HepG2 microsomal fractions (y axis) vs concentration of 25HC3S (x axis).

In Vitro and In Vivo Testing of the Effect of the Nuclear Oxysterol 25HC3S on Triglyceride and Cholesterol Levels The effect of the addition nuclear oxysterol on cholesterol levels was tested in human hepatocyte HepG2 cell line, and the results are presented in FIG. 19. As can be seen, administration of the nuclear oxysterol resulted in a significant decrease in the level of cholesterol detected in microsomal fractions of the HepG2 cells, when compared to the control (25HC3S concentration=0).

Figure 20:
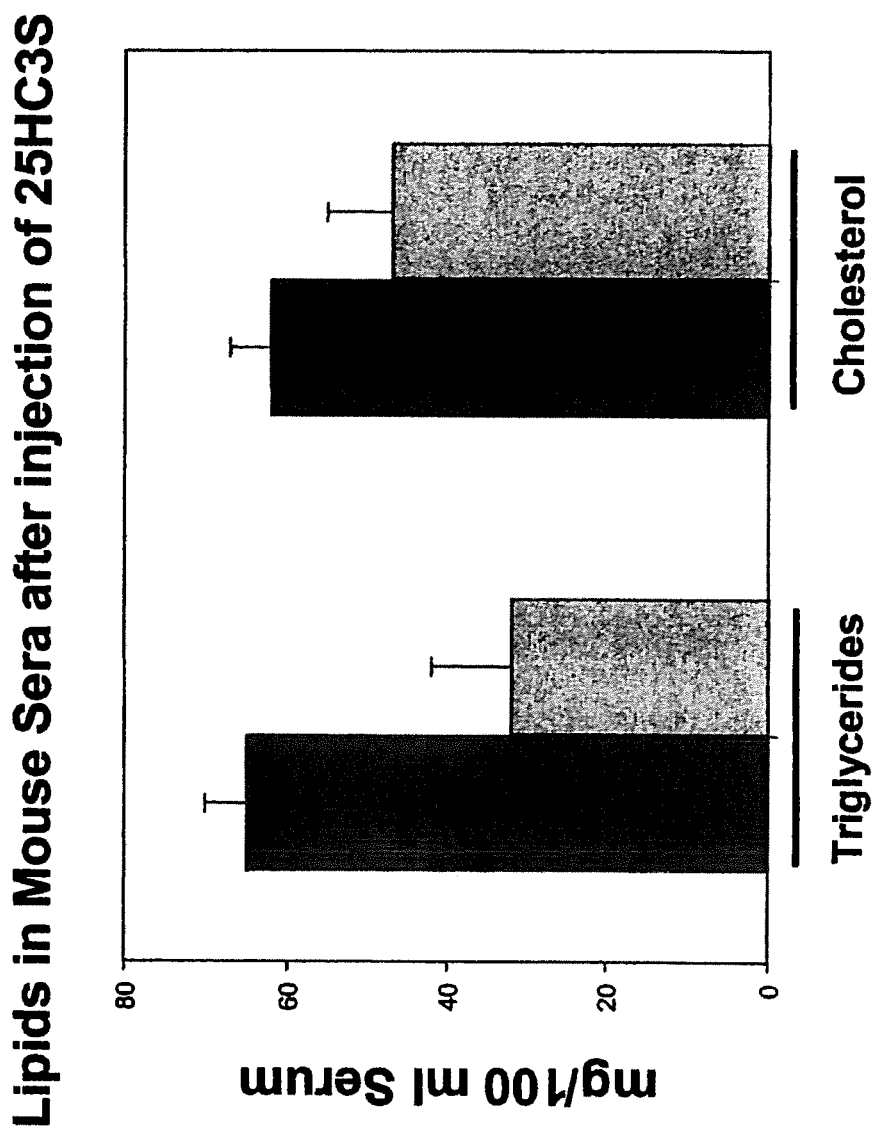
FIG. 20. Lipids in mouse sera after injection of 25HC3S.

Administration to female mice (20-25g weight) was by peritoneal injection once with or without 72 μg of the nuclear oxysterol in 100 μl of 0.9% NaCl containing 3 μl of ethanol. Twelve hrs following the injection, blood was harvested for analysis of triglycerides and cholesterol. The results are presented in FIG. 20, which shows that injection of the nuclear oxysterol decreased triglycerides in serum by 40% (n=12, p<0.01) and decreased cholesterol levels by 15%. Further, injection of the nuclear oxysterol did not increase the activities of alkaline phosphotase, serum glutamate pyruvate transaminase (SGPT), and serum glutamic-oxaloacetic transaminase (SGOT) in sera suggesting that the nuclear oxysterol is non-toxic (data not shown).

To test the effect of diet on cholesterol levels, mice were provided with either a normal or high cholesterol diet for 8 days, and treated with the nuclear oxysterol as described above. Liver tissues were collected for pathohistochemistry studies (Sudan IV staining) and the results showed that administration of the oxysterol significantly decreased triglyceride levels in liver tissues of mice that were fed normally and also of mice that were fed a high cholesterol diet (data not shown).

This study demonstrates that this natural nuclear oxysterol, 25HC3S, could serve as a potent drug for the treatment and prevention of hypercholesterolemia and hyperlipidemia, and related diseases such as atherosclerosis.

Example 6

25-Hydroxycholesterol-3-Sulfate (25HC3S) Activates PPARγ and Attenuates Inflammatory Responses in Human Macrophages The nuclear orphan receptor PPARγ is particularly important in regulating inflammatory responses in macrophages. Activation of PPARγ represses key inflammatory response gene expressions. However, the regulation of PPARγ activation is obscure. Recently, a new cholesterol metabolite, 25-hydroxycholesterol-3-sulfate (25HC3S), was identified as a potent regulatory molecule of lipid metabolism. This Example explores the effect of 25HC3S and its precursor, 25-hydroxycholesterol (25HC) on PPARγ activation and inflammatory responses. Addition of 25HC3S to human macrophages markedly increased nuclear PPARγ, cytosol IκB, and decreased nuclear NFκB protein levels. PPARγ response element reporter gene assays showed that 25HC3S significantly increased luciferase activities. NFκB-dependent promoter reporter gene assays showed that 25HC3S suppressed TNFα-induced luciferase activities only when co-transfected with pCMX-PPARγ plasmid in H441 cells. In addition, 25HC3S decreased LPS-induced TNFα and IL-1β mRNA expressions and releases. In the PPARγ-specific siRNA transfected macrophages, 25HC3S failed to increase IκB and to suppress TNFα and IL-1β expression. In contrast to 25HC3S, its precursor 25HC, a known LXR ligand, decreased nuclear PPARγ, cytosol IκB, while increasing nuclear NFκB protein levels in the presence of LPS and TNFα. This demonstrates that 25HC3S acts in macrophages as a PPARγ activator, and suppresses inflammatory response via PPARγ/IκB/NFκB signaling pathway.

Macrophages are the key cellular players in the pathophysiology of atherosclerosis. In the early stage of atherosclerosis, macrophages in arterial walls may accumulate lipids. These lipid-loaded macrophages, termed foam cells, are characteristic of a reversible early cellular phase of atherosclerotic lesions. Progressive lipid accumulation leads to further escalation of inflammatory responses and infiltration of inflammatory cells [1]. Through this process, early cellular lesions are transformed to late, fibrous atherosclerotic plaques. Physiological or pharmacological maneuvers that reduce macrophage lipids and inflammatory responses may be effective in preventing or reversing atherosclerosis.

Nuclear orphan receptors are ligand-activated transcription factors that regulate the expression of target genes to affect processes as diverse as reproduction, inflammation, development, and general metabolism [2]. Nuclear receptor peroxisome proliferation activator receptors (PPARs), which play major roles in the regulation of lipid metabolism, glucose homeostasis, and inflammatory process, are implicated in the control of diverse diseases such as type II diabetes and atherosclerosis, and are believed to be ideal targets for therapeutic management strategies for many metabolic disorders [3-8]. Activation of PPARγ leads to the formation of heterodimers with RXRs. The heterodimers bind to DNA-specific sequences called peroxisome proliferator response elements (PPRE) and lead to up- or down-regulation of transcriptional activity of target genes [9]. Several natural compounds such as fatty acids, PGD2-derivatives, eicosanoids have been reported to act on PPARγ [10-13]. However, their affinities with PPARγ protein are low [14-16]. Thus, natural ligands for PPARγ and the regulating mechanisms of its activation are yet to be elucidated.

Oxygenated cholesterols, oxysterols, play an important role in maintenance of lipid homeostasis [17]. Recently, we identified a novel oxysterol, 25-hydroxycholesterol-3 sulfate (25HC3S), that accumulates in hepatocyte nuclei following overexpression of the mitochondrial cholesterol delivery protein, StarD1 [18-20]. Macrophages are able to synthesize this oxysterol [21]. This oxysterol appears to be synthesized from 25HC by sterol sulfotransferase 2B1 (SULT2B1) [22]. Of note is that overexpression of SULT2B1 impairs the response of liver oxysterol receptor LXR to multiple oxysterol ligands [23].

Furthermore, the addition of 25HC3S to primary hepatocytes down-regulates expression of key enzymes involved in lipid metabolism and decreases lipid biosynthesis by inactivating the LXR/SREBP-1 signaling pathway in hepatocytes and macrophages [21,24]. Several studies show that inflammation is closely associated with disordered lipid metabolism [25,26]. Infection and inflammation induce the acute-phase response (APR), leading to multiple alterations in lipid and lipoprotein metabolism. APR increases plasma triglyceride levels, de novo hepatic fatty acid synthesis, and suppression of fatty acid oxidation [27]. The molecular mechanisms during the APR involve coordinated changes in several nuclear orphan receptors, including PPARs, LXRs, and RXRs [27,28]. PPARγ as well as LXRs are lipid-activated transcription factors and reciprocally regulate inflammation and lipid metabolism [3,29]. The processes by which these events occur are poorly understood. Cholesterol metabolites 25HC and 25HC3S have been shown to be the potent regulators involved in lipids metabolism via LXRs/SREBPs signaling pathway [21,24]. It is thus possible that they are able to regulate inflammatory response through PPARγ signaling pathway.

Data presented in this Example demonstrates that 25HC3S is a potent down-regulator while 25HC is an up-regulator of inflammatory responses. Evidence is provided that their effects on the inflammatory response are mediated via activation of the PPARγ /IκB/NFκB signaling pathway in macrophages. These findings imply a new signaling pathway for the interaction between inflammatory response and lipid metabolism.

Materials and Methods

Cell culture reagents and supplies were purchased from GIBCO BRL (Grand Island, N.Y.); the reagents for real time RT-PCR were obtained from AB Applied Biosystems (Applied Biosystems, Foster City, Calif.). Antibodies against human PPARγ, IκB, and Lamin B were purchased from Santa Cruz Biotechnology (Santa Cruz, Calif.). FuGENE HD transfection reagent was obtained from Roche Applied Science (Indianapolis, Ind.). Single Analyte ELISArray™ Kits were purchased from SupperArray (Frederick, Md.). The Dual-Glo Luciferase Assay System and pGL3-NFκB -luc were purchased from Promega (Wisconsin, Wis.); PPAR agonist rosiglitazone and antagonist T0070907 were from New Cayman Chemical (Ann Arbor, Mich.). pGL3-PPAR response element (PPRE)-luciferase reporter containing three copies of PPRE from the promoter of rat acyl CoA oxidase, and the receptor expression plasmids pcDNAI-PPAR were from the University of Tennessee Health Science Center [30].

Cell Culture

Human THP-1 monocytes and H441 cells were purchased from the American Type Culture Collection (Manassas, Va.) and maintained according to the supplier's protocols. THP-1 monocytes were differentiated to macrophages by adding 100 nM of phorbol 12-myristate 13-acetate (PMA). When cells reached ~90% confluence, oxysterols in DMSO or in ethanol (the final concentration in media was <0.1%) were added as indicated. The cells were harvested at the times as indicated. Nuclear and cytosolic fractions were isolated using NE-PER®, Nuclear and Cytoplasmic Extraction Reagents (Pierce, Rockford, Ill. Western blot analysis of nuclear PPAR and intracellular I B levels Fifty μg of total cell lysates or nuclear protein extracts, otherwise as indicated, were separated on 10% SDS-PAGE gels and transferred onto a polyvinylidene difluoride membrane as described previously [31]. Membranes were blocked in TBS containing 5% of nonfat dried milk for 1 hr. The specific proteins were determined by incubation with specific antibodies against human PPAR or IκB overnight at 4° C. with shaking. After washing, the membrane was incubated in a 1:3,000 dilution of a secondary antibody (goat anti-rabbit or anti-mouse IgG-HP conjugate; Bio-Rad, Hercules, Calif.) at room temperature for 1 hr in the washing buffer (Tris buffered solution containing 0.5% Tween 20). The protein bands were visualized using Western Lightening Chemiluminescence Reagent (Perkin-Elmer, Waltham, Mass.). The expression levels were normalized to Lamin.

PPARγ Transcription Factor Assay

PPAR response elements (PPRE) binding activities were measured using an enzyme-linked immunosorbent assay (PPAR transcription factor assay kit; Cayman Chemical, Ann Arbor, Mich.). The 96-well plate was preimmobilized with deoxyoligonucleoties containing PPRE. THP-1 derived macrophages were treated with 25HC3S at indicated concentrations or rosiglitazone for 4 hrs. The cells were then rinsed and nuclear proteins were extracted according to the manufacturer's instructions. Total nuclear extract protein, 10 g from each sample, was added to the plate. The kit provided two negative as zero controls, one positive as maximal binding control, and one competitive as specific binding control (in the presence of dsDNA) were used in the assay. After incubating for 1 hr, the wells were washed and incubated with primary PPAR antibody which recognizes the accessible epitope on PPAR protein upon PPRE binding. The peroxidase-labeled second antibody was added and incubated for 1 hr. The reaction was stopped and absorbance was read at 450 nm in a spectrophotometer.

Transfection and Promoter Reporter Gene-Luciferase Assays

H441 cells were seeded in 96-well plates. When cell density reached 90-95%, the cells were transfected with an expression plasmid as indicated using a lipid-based FuGENE HD transfection reagent according to the manufacture (Roche, Indianapolis, Ind.). A synthetic renilla luciferase reporter, phrG-TK (Promega, Wisconsin, Wis.), was used as a luciferase internal standard. For PPRE reporter gene assay, 50 ng of pGL3-PPRE-acyl-CoA oxidase luciferase reporter, 50 ng of expression plasmid pCMX-PPARγ, and 50 ng of phrG-TK vector (internal standard) were cotransfected as per the manufacture's instruction. Twenty four hrs after the transfection, different concentration of 25HC3S, rosiglitazone, and/or T0070907 were added and incubated for another 24 hrs. Luciferase activities were determined using the Dual-Glo Luciferase Assay System according to the manufacturer's protocol (Promega, Wisconsin, Wis.). The amount of luciferase activity was measured using a TopCount NXT Microplate Scintillation and Luminescence Counter (Packard, Meriden, Conn.) and normalized to the amount of phG-TK luciferase activity. Transfections were carried out in triplicate for each sample, and each experiment was repeated three times.

Detection of Intracellular Distribution of PPARγ in THP-1 Derived Macrophages

THP-1 derived macrophages were cultured on coverslips in six-well plates and treated with different concentrations of 25HC and 25HC3S for 4hrs. The cells on coverslips were washed with PBS, fixed with 3.7% formaldehyde for 10 min at 4° C., and then rinsed three times with PBS at room temperature. They were then permeabilized with PBS containing 0.1% of TritonX-100 for 3 min and washed with PBS before blocking by incubation with 5% of normal goat serum in PBS overnight at 4° C. For interaction with primary antibodies, cells were incubated with 2.5% normal goat serum in PBS containing PPARγ antibody for 1 hr in an incubator. Cells were washed in PBS containing 0.05% of Tween 20 (3×10 min). The bound primary antibodies were visualized with Alexa Fluor 488 goat anti-mouse IgG. The minor groove of double stranded DNA as a nuclear marker was stained by DAPI. Afterwashing, coverslips were mounted on slides and viewed with a Zeiss LSM 510 Meta confocal microscope. Scalebar=10μm.

Determination of mRNA Levels by Real-Time RT-PCR

Total RNA was isolated from THP-1 derived macrophages following treatments for 6 hrs otherwise as indicated using SV Total RNA Isolation Kit (Promega, Wisconsin, Wis.), which includes DNase treatment. Two microgram of total RNA was used for first-strand cDNA synthesis as recommended by manufacturer (Invitrogen, Carlsbad, Calif.). Real-time RT-PCR was performed using SYBR Green as indicator on ABI 7500 Fast Real-Time PCR System (Applied Biosystems, Foster City, Calif.). The final reaction mixture contained 10 ng of cDNA, 100 nM of each primer, 10 μl of 2× SYBR® Green PCR Master Mix (Applied Biosystems, Foster City, Calif.), and RNase-free water to complete the reaction mixture volume to 20 μl. All reactions were performed in triplicate. PCR was carried out for 40 cycles of 95° C. for 15 s and 60° C. for 1 min. The fluorescence was read during the reaction, allowing a continuous monitoring of the amount of PCR product. The data was normalized to internal control GAPDH. The sequences of primers are used as recommended at the website located at pga.mgh.harvard.edu/primerband, as shown in Table 2.

SiRNA-Mediated Macrophage RNA Interference pSilencer2.1-U6 neo siRNA expression vector and negative control for RNAi were purchased from Ambion, Inc. (Austin, Tex.). Three human PPARγ oligonucleotide sequences, GACTCAGCTCTACAATAAG (siRNA1, SEQ ID NO: 13), GCGATTCCTTCACTGATAC (siRNA2, SEQ ID NO: 14), and GCTTATCTATGACAGATGT (siRNA3, SEQ ID NO: 15), were selected as specific siRNAs to target human PPARγ. Synthetic sense and antisense oligonucleotides were annealed by incubated at 90° C. for 3 min and then at 37° C. for 1 hr. The double stranded oligonucleotides were cloned into the BamH I-Hind III sites of the pSilencer2.1-U6 neo vector according manufacturer's protocol. The control RNA interference (RNAi) sequence was a randomly scrambled and was not found in the mouse, human, or rat genome databases. All of the constructs were confirmed by sequencing. THP-1 macrophages were transfected with a PPARγ siRNA or control RNAi using FugeneHD reagent according to the manufacturer's instructions (Roche Applied Science, Indianapolis, Ind.). After incubation for 4 hrs, the medium was changed with normal medium and compounds were added at appropriate concentrations as indicated. Cells were harvested after 48 hrs following the addition, and PPARγ protein levels were determined using western blot and mRNA levels of inflammatory response factors were measured by real time RT-PCR analysis.

Statistics

Data are reported as mean ±standard deviation (SD). Where indicated, data were subjected to t-test or ANOVA analysis and determined to be significantly different at $p<0.05$.

TABLE 2

Primer sets used for real-time RT-PCR

| Gene Name | GenBank Nos. | Forward Sequence | Reverse Sequence |
| --- | --- | --- | --- |
| GAPDHR | NM-002046 | CAATGACCCCTTCATTGACC (SEQ ID NO: 3) | TTGATTTTGGAGGGATCTCG (SEQ ID NO: 4) |
| IL-1β | NM-000576 | CACGATGCACCTGTACGATCA (SEQ ID NO: 5) | GTTGCTCCATATCCTGTCCCT (SEQ ID NO: 6 |
| TNFα | NM-000594 | TCTTCTCGAACCCCGAGTGA (SEQ ID NO: 7) | CCTCTGATGGCACCACCAG (SEQ ID NO: 8) |
| IκB | NM-001278 | GGCTTCGGGAACGTCTGTC (SEQ ID NO: 9) | TGGCATGGTTCAACTTCTTCAT (SEQ ID NO: 10) |
| IL-8 | NM-000584 | ACTGAGAGTGATTGAGAGTGGAC (SEQ ID NO: 11) | AACCCTCTGCACCCAGTTTTC (SEQ ID NO: 12) |

ELISA Analysis of Cytokine Releases

A total of 1×10⁶ macrophages were treated with LPS (1 μg/ml) and/or different concentrations of 25HC or 25HC3S for 24 hrs. Supernatants were harvested and cytokines IL-1β and TNF-α concentration were measured by enzyme-linked immunosorbent assay (ELISA) according to manufacturer's instruction (SuperArray Bioscience, Frederick Md.).

Results

25HC3S Administration Increases Nuclear PPARγ levels in Macrophages

Figure 21B:
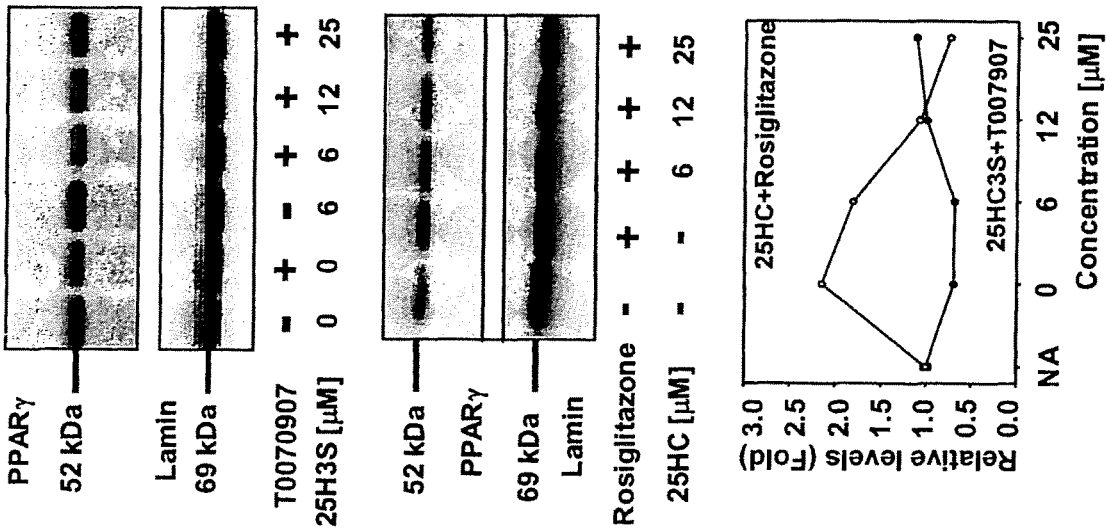
FIGS. 21A and 21B. Effects of 25HC3S and 25HC on PPARγ protein levels in THP-1 macrophages. A, THP-1 macrophages were treated with 25HC3S (top panel) or 25HC (middle panel) at different concentration as indicated for 4 hrs. The nuclear PPARγ levels were analyzed by Western blot. B, The macrophages were pre-incubated with 1 μM of T0070907 for 2 hrs and treated with 25HC3S (tip panel) or preincubated with 1 μM of rosiglitazone for 2 hrs; and treated with 25HC for 4 hrs (middle panel). Expression levels were normalized to Lamin as shown in the bottom panels. The data represent one typical result out of three experiments.
Figure 21A:
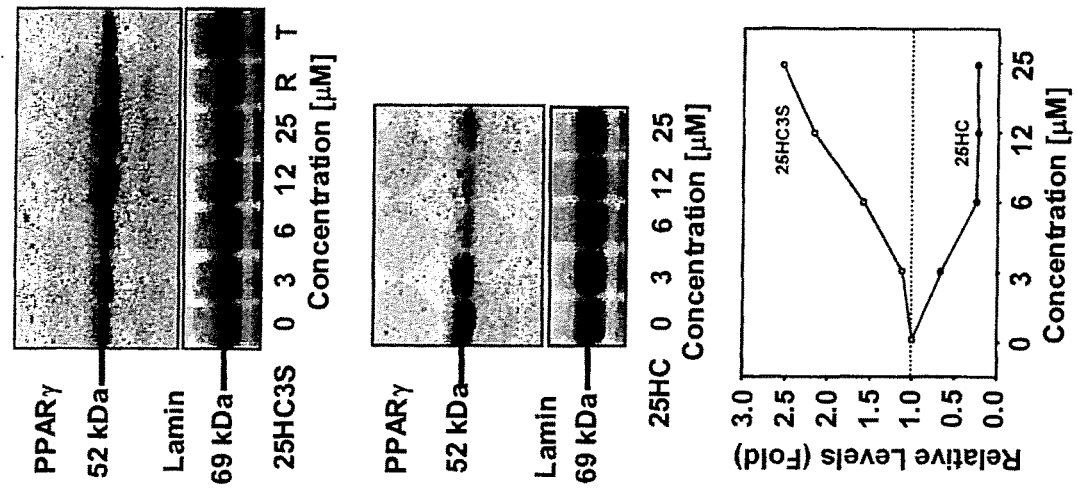

To examine the effect of 25HC3S and its precursor 25HC on PPARγ activation, total nuclear proteins were extracted and nuclear PPARγ levels were determined by western blot analysis. As shown in FIGS. 21A and 21B, addition of 25HC3S to the macrophages led to significant concentration- (FIG. 21A, upper panels) and time- (data not shown) dependent increases in nuclear PPARγ protein levels. To confirm the increasing 52 kDa band was PPARγ protein, an artificial PPARγ ligand, rosiglitazone, was used as positive control and a specific antagonist, T0070907, as negative control (FIG. 21B). As shown in FIG. 21A, 25HC3S and rosiglitazone substantially increased nuclear PPARγ levels (Lane R) while T0070907 decreased the level (Lane T). In contrast, 25HC decreased PPARγ levels (middle figures of FIG. 21A). It was noticed that the increases or decreases in the nuclear PPARγ levels occurred only in the early stages, less than 4 hrs (data not shown). Summaries of the concentration-dependent increases or decreases after normalization to nuclear protein lamin are shown in the lower panel of FIG. 21A. These results suggest that 25HC3S functions as a PPARγ agonist and 25HC as an antagonist. To further confirm that 25HC3S binds with the same molecule as the artificial antagonist, a competitive assay was performed. In the presence of the antagonist T0070907, 25HC3S failed to increase the nuclear PPARγ levels to its maxima. However, the levels of inhibition could be partially reversed following increasing concentration of 25HC3S as shown in the top panel of FIG. 21B. In contrast, rosiglitazone increased nuclear PPARγ levels and the increased levels could be significantly inhibited by the presence of 25HC as shown in the middle panel of FIG. 21B. These results suggested that 25HC3S/T0070907 and 25HC/rosiglitazone are competitive and they bind with the same molecule, PPARγ. Real time RT-PCR analysis showed that neither 25HC nor 25HC3S was able to change PPARγ mRNA levels significantly (data not shown), suggesting these oxysterols have no effect on its transcriptional regulation.

Figure 22A:
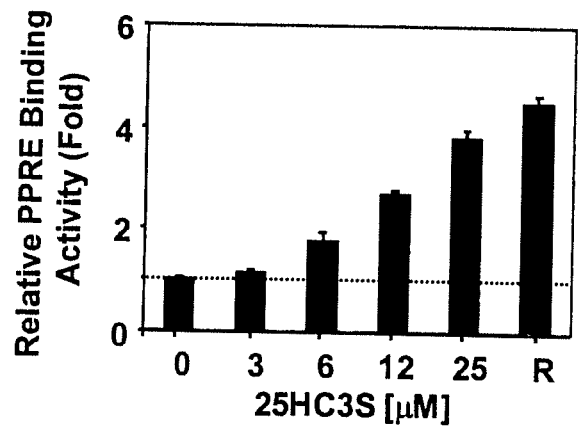
FIG. 22A-E. 25HC3S enhances nuclear PPRE transcriptional activities and inhibits LPS-induced TNF-α and IL-1β expressions and releases. THP-1 macrophages were treated with the indicated concentrations of 25HC3S or 2 μM of rosiglitazone for 4 hrs. A, The nuclear proteins were extracted and PPRE transcriptional activities were determined by the ELISA. R represents rosiglitazone. Reporter gene activity assays were determined in H441 cells following co-transfection with promoter reporter gene and expression of plasmid pCMX-PPARγ: 25HC3S (B) or rosiglitazone (C) with or without 1 μM of T0070907 was added and incubated for another 24 hrs. Luciferase activities were determined. For competitive assays, the cells were preincubated with T0070907 for 1 hr and incubated with 25HC3S at the different concentrations as indicated. After 24 hrs, the cells were incubated with LPS for 3 hrs. The expression of mRNA for TNFα and IL-1β was determined by real-time RT-PCR (D). The released TNFα and IL-1β concentrations in the media following the addition of LPS were measured by ELISA respectively (E). Data represent means±SD (n=3). The symbol * represents significant difference (p<0.05).
Figure 22B:
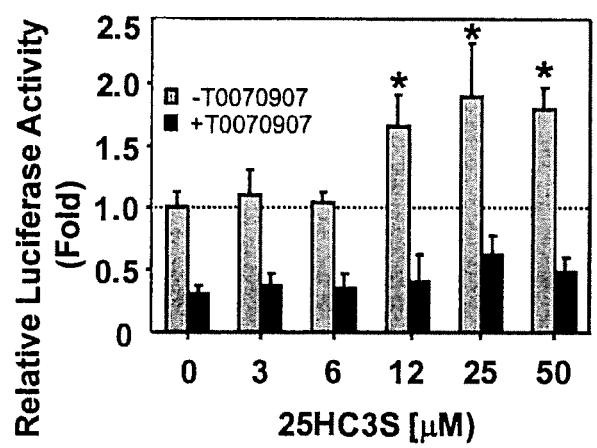
Figure 22C:
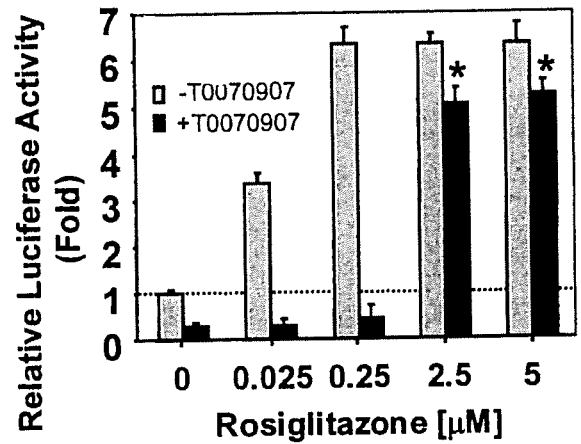
Figure 22D:
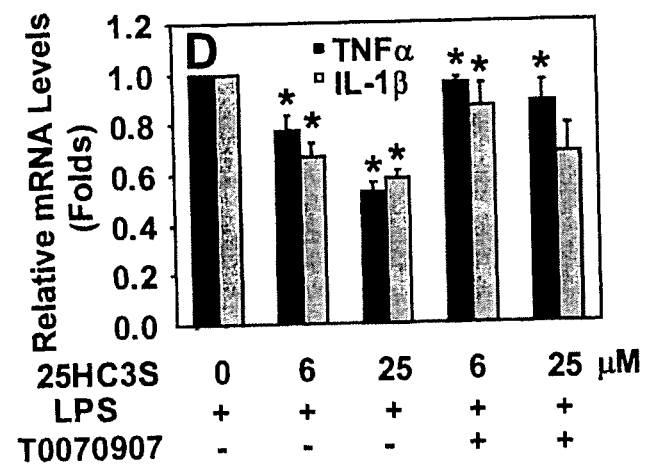
Figures 28A, 28B:
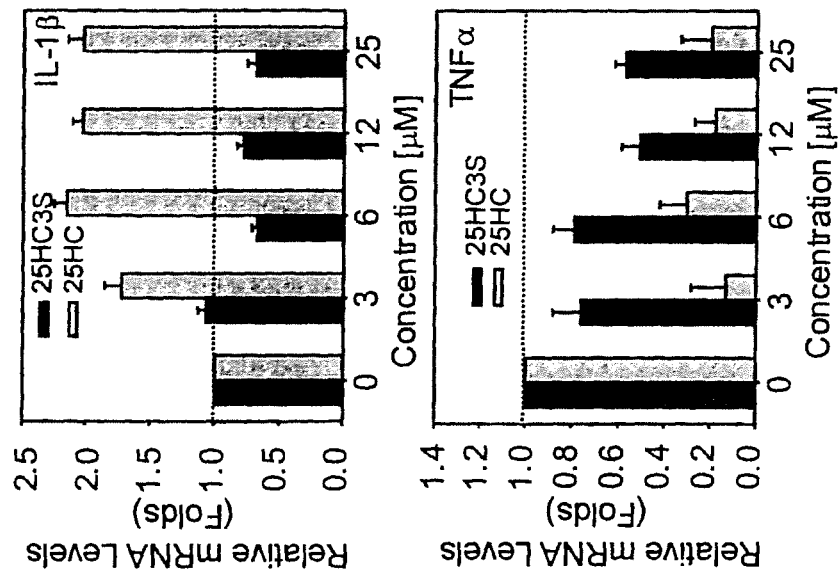
FIG. 28A and B. Addition of 25HC3S suppresses LPS-induced IL-1(3 (A) and TNFγ (B) expression in macrophages. To study the effect of 25HC3S on LPS-induced TNFα and IL-1β expression and release, macrophages were treated with 1 μg/ml of LPS and different concentrations of 25HC3S and 25HC as indicated for 25 hours; mRNA levels of TNFα and IL-1β were determined by real time RT-PCR. The results represent mean±SD. Addition of LPS dramatically increased IL-1β mRNA levels by 55-fold. Addition of 25HC3S significantly suppressed this increase, while 25HC significantly increased levels still further (A). Both 25HC3S and 25HC repressed LPS-induced TNFα mRNA levels as shown in B.

Double immunofluorescence studies using DAPI for the nuclear marker together with the PPARγ antibody showed that PPARγ proteins were widely distributed in the cytosols and nuclei of the macrophages (FIG. 27A-F): compared with DMSO, administration of 25HC3S increased the nuclear PPARγ fluorescence intensities; administration of the antagonist T0070907 decreased the intensity, and blunted 25HC3S stimulation. The results imply that 25HC3S increases PPARγ levels in the nuclei by increasing nuclear translocation. 25HC3S addition increases PPARγ-response transcriptional activities and represses inflammatory responses To study the transcriptional activities of the nuclear extracts from 25HC3S-treated macrophages, PPARγ responsive elements (PPRE) immobilized ELISA and PPRE reporter gene assay were carried out as shown in FIGS. 22A-22E. ELISA assay showed that addition of 25HC3S significantly increased the PPRE-binding activities of the nuclear extracts, which is concentration-dependent ($p<0.01$) (FIG. 22A). PPRE reporter gene assays were performed in H441 cells because our preliminary experiments showed that these cells had the best transfection efficiency and highest reciferase activities (data not shown). At 25 µM of 25HC3S, the activity reached to a similar levels as that induced by the PPARγ agonist rosiglitazone. In the presence of the antagonist T0070907, 25HC3S failed ($p<0.01$) to increase PPARγ reporter gene activities with co-overexpression of ACOX-PPRE reporter and PPARγ genes (FIG. 22B). Interestingly, in the presence of T0070907, the lower concentrations of rosiglitazone failed to stimulate the reporter gene activity ($p<0.01$) but the higher concentrations still could increase the activities as shown in FIG. 22C. The results suggested that 25HC3S activates PPARγ by binding with different motif and rosiglitazone binds with the same motif of the molecule as T0070907 or with different affinities. Addition of 25HC3S suppresses LPS-induced IL-1β and TNFα expressions and releases in macrophages. Addition of LPS substantially increased IL-1β mRNA levels by 55-fold and significantly increased TNFα by 2-fold as previously reported [32,33]. Addition of 25HC3S suppressed LPS-induced IL-1β mRNA levels by 2-fold while 25HC increased its levels by 2-fold (FIG. 28A and B). However, both 25HC3S and 25HC repressed LPS-induced TNFα mRNA levels by two and four folds, respectively (FIGS. 28A and B). It was noticed that 25HC was significantly stronger than 25HC3S in suppressing LPS-induced TNFα expression ($p<0.05$). The suppressions of IL-1(3 and TNFα expression by 25HC3S could significantly be blunted in the presence of artificial PPARγ antagonist T0070907 ($p<0.05$) as shown in FIG. 22D. These results suggested that 25HC3S inhibits LPS-induced IL-1β and TNFα expression by PPARγ signaling pathway.

Figure 22E:
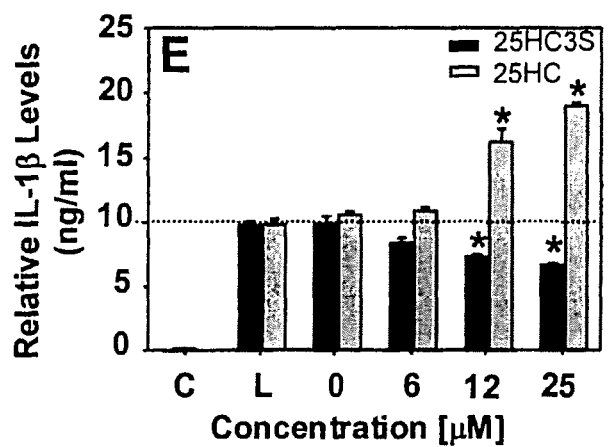

Consistently, 25HC3S represses the LPS-induced releases of IL-1β and TNFα in the macrophages. Addition of LPS increased TNFα release by 50-fold (data not shown) and increased IL-1β releases by 10-fold (FIG. 22E, Lanes C and L), which was similar with previous reports [32,33]. Interestingly, addition of 25HC3S significantly decreased LPS-induced IL-1β release, but 25HC increased IL-1β release ($p<0.05$), which are concentration-dependent manner as shown in FIG. 22E.

Figure 23A:
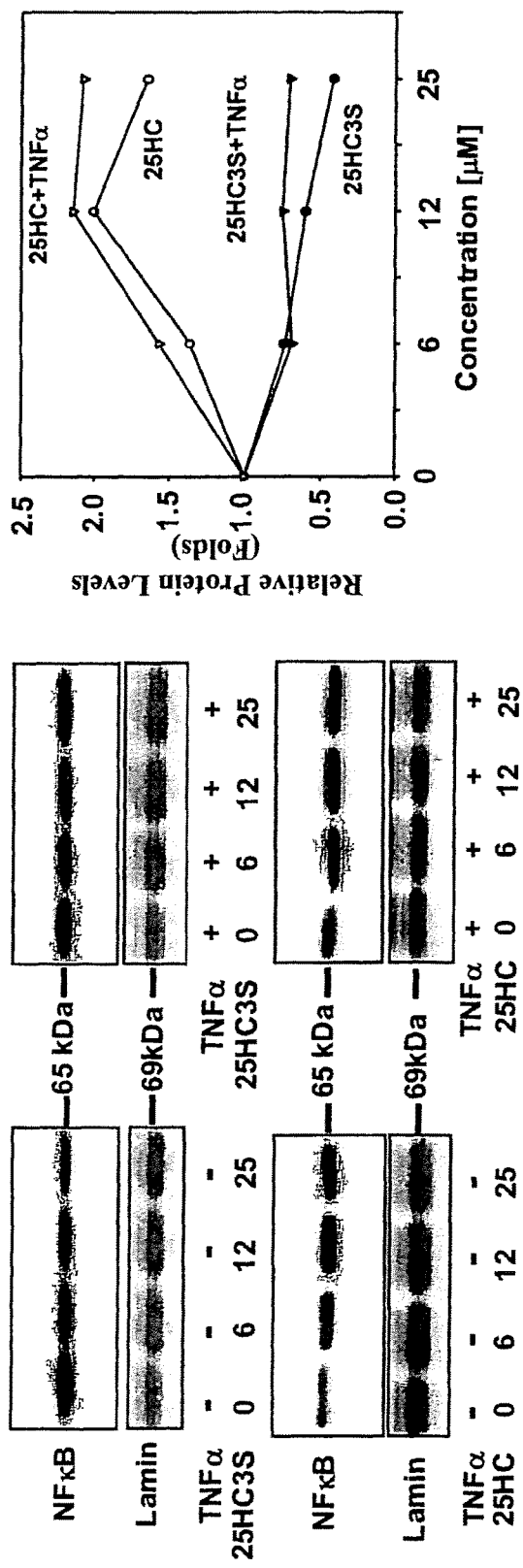
FIG. 23A and B. 25HC3S-mediated suppression of NFκB activation is PPARγ-dependent. A, THP-1 macrophages were treated with 25HC3S or 25HC for 24 hrs followed by addition or no addition of TNFα for another 3 hrs. The nuclear NFκB levels were analyzed by Western blot. The data represent one typical result out of three experiments. B, NFκB activation is PPARγ dependent. H441 cells were transfected with pNFκB dependent reporter gene-Luc, treated with or without T0070907 for 1 hr, and incubated with 25HC3S at indicated concentration for 24 hrs. The reporter gene expression was induced by incubating with 10 ng/ml of TNFα for 3 hrs. The left figure represents cells transfected with pNfκB dependent reporter gene-Luc plasmid alone; the right figure, represents cells co-transfected with PPARγ expression plasmid. The symbol * represents significant difference (p<0.05).

PPARγ is Involved in 25HC3S-Mediated Suppression of Inflammatory Responses via NFκB TNFα can activate IκB kinase, which phosphorylates IκB followed by its ubiquitination and subsequent degradation. In the absence of TNFα 25HC3S treatment decreased ($p<0.05$) but 25HC increased nuclear NFκB levels (Left panels in FIG. 23A). In the presence of TNFα, 25HC3S failed to decrease, but 25HC still significantly increased its nuclear NFκB levels (Right panels in FIG. 23A). In its inactive form, NFκB is sequestered in the cytoplasm, bound by members of the IκBs. When IκBs are phosphorylated, ubiquitinated, and degraded, NFκB will be activated and enter nuclei. Thus, the results imply that the decreases/increases in the nuclear NFκB by these oxysterols are related with IκB degradation.

Figure 23B:
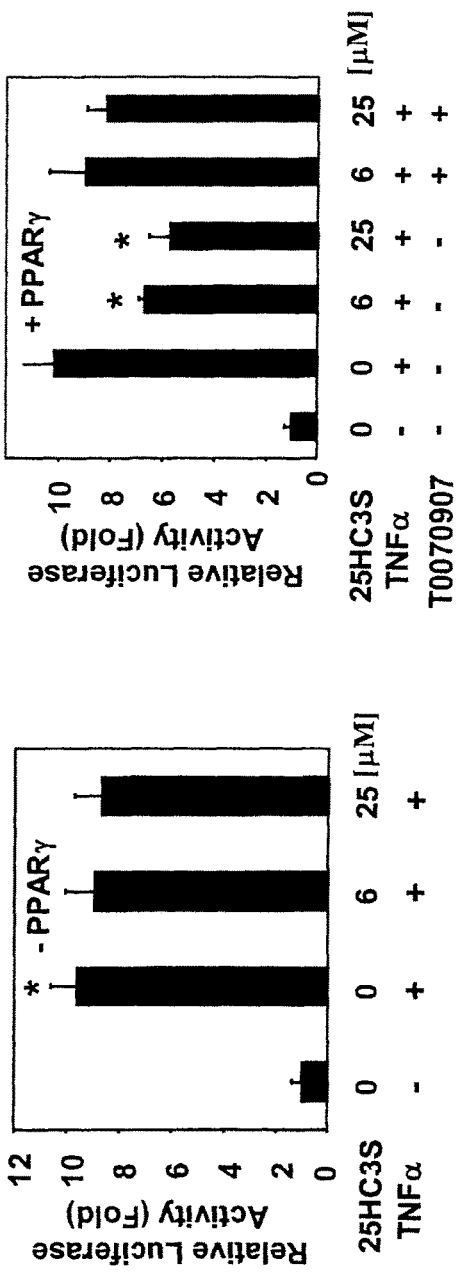

To investigate whether the NFκB regulation is PPARγ dependent, H441 cells were transfected with pNFκB dependent reporter gene-Luc expression plasmid alone or co-transfected with PPARγ expression plasmid. In the absence of PPARγ expression plasmid, TNFα induced the reporter gene expression by 10-fold and 25HC3S failed to suppress its induction as shown in left panel of FIG. 23B. In the co-transfected cells, the presence of PPARγ expression, TNFα still induced the reporter gene expression by 10-fold but 25HC3S reduced its induction by 50% (Right panel of FIG. 23B). Furthermore, in the presence of PPARγ antagonist, the suppression was blunted (Right panel of FIG. 23B). The results suggested that the suppression of TNFα -induced NFκB dependent reporter gene expression by 25HC3S requires the presence of PPARγ protein.

Figure 24A:
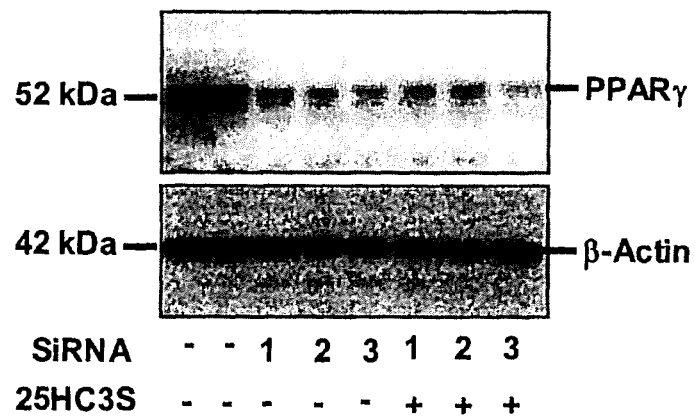
FIG. 24A-E. 25HC3S failed to suppress LPS induced TNFα, IL-1β and NFκB, and TNFα induced IκB mRNA expression in the PPARγ knock down macrophages. Following expression of PPARγ-specific siRNAs in the macrophages treated with or without 12 μM of 25HC3S for 48 hrs, nuclear PPARγ protein levels were determined by Western bolt analysis as shown in A. The mRNA levels of IκB and NFκB (B), TNFα (C), IL-1β (D), and NFκB (E) were determined by real time RT-PCR analysis. The values represent means±SD (n=3). The symbol * represents statistically significance (p<0.05).
Figure 24B:
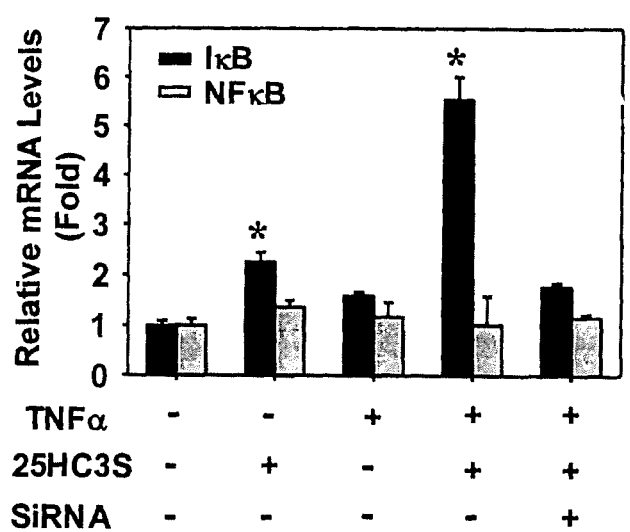
Figure 24C:
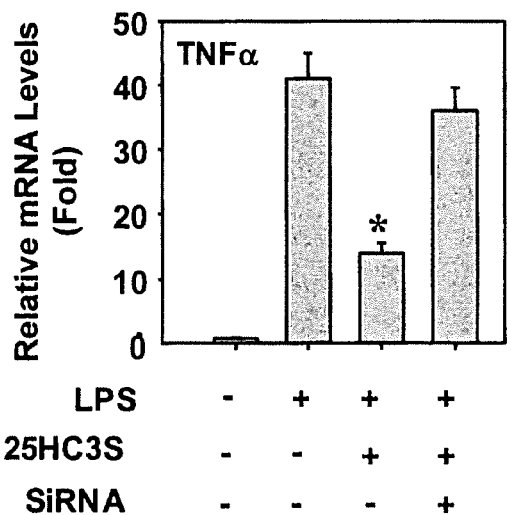
Figure 24D:
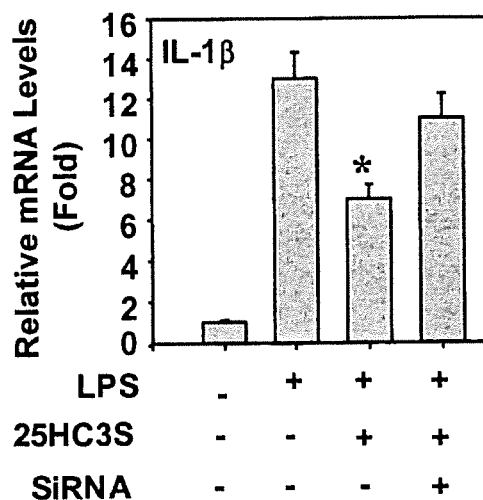
Figure 24E:
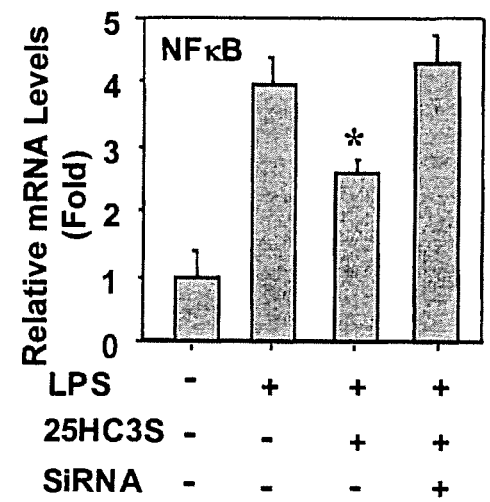

To confirm that the suppression of LPS-induced TNFα and IL-1β expression is PPARγ dependent, specific siRNAs were used to knock-down PPARγ. Following transfection of the recombinant plasmid encoding specific siRNAs for 48 hrs, about 45% of the cells were viable and harvested. About 90% of PPARγ protein levels were suppressed and their levels were not changed in the presence of 12 µM of 25HC3S as shown in FIG. 24A. Consistently, 25HC3S significantly increased IκB mRNA levels by 2.5 folds, and in the presence of TNFα, 25HC3S increased the levels by 6 folds, which can be abolished by PPARγ specific siRNA (FIG. 24B). As expected, LPS stimulated TNFα by 40 folds and IL-1β expression by 12 folds, and 12 μM of 25HC3S significantly suppressed LPS-induced TNFα (FIG. 24C), IL-1β (FIG. 24D), and NFκB (FIG. 24E) expression (p<0.05). However, in the siRNA-expressed cells, 25HC3S failed in suppressing these expressions (FIGS. 24C, 24D and 24E). These results suggest that the 25HC3S induces repression of nuclear NFκB levels and subsequently decreases TNFα and IL-1β expression through PPARγ induced IκB expression.

Figure 25B:
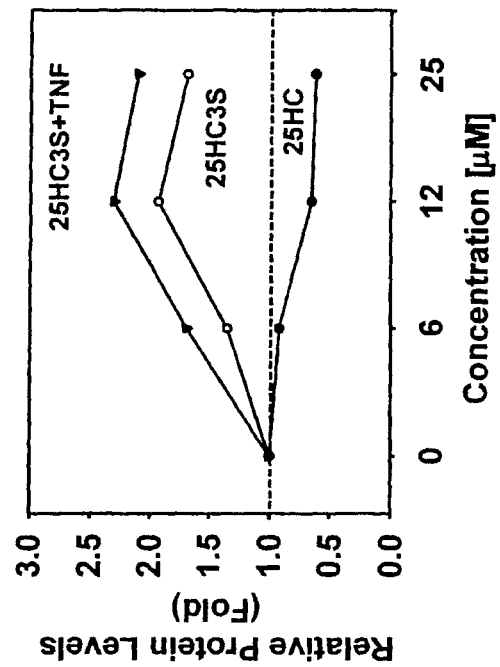
FIG. 25A-C. Effects of 25HC3S on expression of IκB mRNA and protein levels in THP-1 macrophages. Effects of 25HC3S and 25HC on IκB protein levels were analyzed by Western blot following the treatment for 24 hrs (A and B) and mRNA levels were determined by real time RT-PCR following the treatment for 6 hrs (C). The Western blot data represents one of three experiments.
Figure 25C:
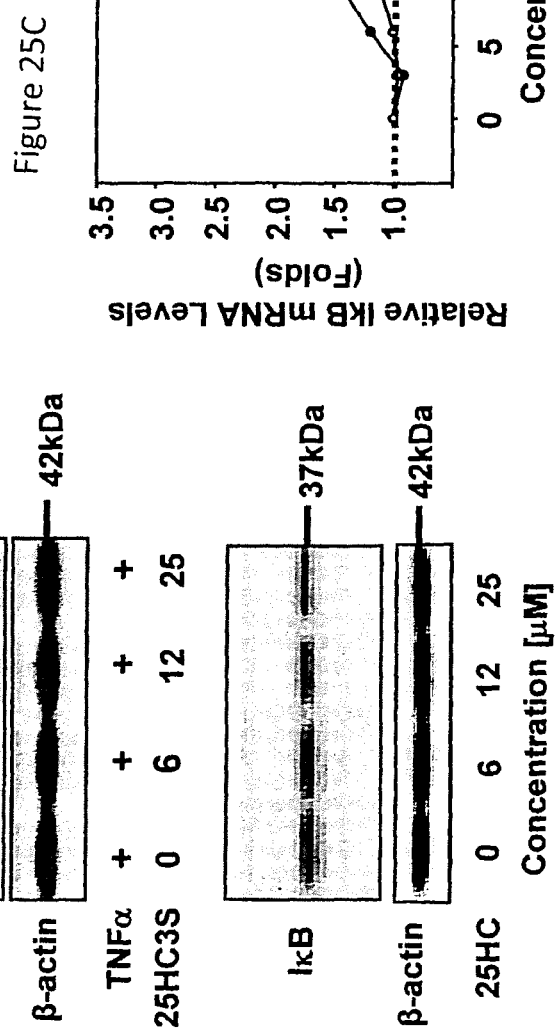
Figure 25A:
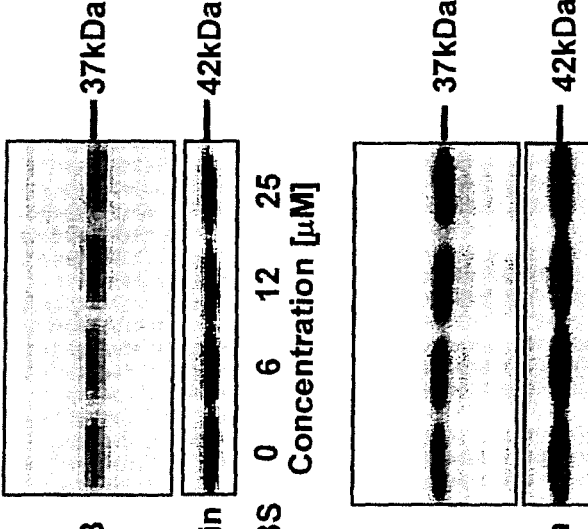

To further confirm that 25HC3S/25HC regulates inflammatory responses through IκB/ NFκB signaling pathway, the effects of these two oxysterols on IκB expression were examined. When the macrophages were treated with 25HC3S, the expression IκB at protein and mRNA levels were significantly increased (FIGS. 25A and 25B). Western blot analysis showed that 25HC3S increased and 25HC decreased IκB protein levels (Upper panel of FIGS. 25A and 25B). When treated with 25HC, the mRNA level had no significantly changed (p>0.05 by ANOVA analysis) (FIG. 25C) but the protein levels were significantly concentration-dependent decreased (p<0.05 by ANOVA analysis) (Lower panel of FIGS. 25A and 25B), indicating 25HC increases IκB protein degradation. In the presence of TNFα, 25HC3S increased IκB protein levels more than those in the absence (Middle panel, FIGS. 25A and 25B), but in the presence of PPARγ antagonist T0070907, 25HC3S failed to increase its levels (data not shown). These results indicated that PPARγ/ IκB/NFκB signaling pathway is involved in 25HC3S/25HC regulated inflammatory responses.

Discussion

Previous reports show that 25HC and 25HC3S serve as ligands, agonist and antagonist, respectively of LXR nuclear receptor [21, 24]. In the present study, we have shown that 25HC3S, increases nuclear PPARγ, cytosol IκB, and decreases nuclear NFκB protein levels; increases PPARγ transcriptional activities and IκB expression; subsequently inhibits the TNFα and LPS-induced inflammatory factor expressions and releases in human THP-1 derived macrophages. In contrast, its precursor 25HC, a known LXR ligand, basically has an opposite function. Thus, the present results provide strong evidence that 25HC and 25HC3S not only coordinately regulate lipid metabolism by LXR/ SREBP-1 [21,24], but also inflammatory responses by PPARγ IκB/NFκB signaling pathway [46]. The role of oxysterols including 25HC in inflammation is controversial. The nuclear receptors LXR and PPARγ regulate inflammation in different ways and respond to distinct signaling pathways [3]. PPARs and LXRs both exert positive and negative control over the expression of a range of metabolic and inflammatory genes. Although LXRs as well as PPARγ can transrepress several inflammatory genes in a similar manner, comparative DNA-microarray studies have identified overlapping, but distinct, subsets of genes that are repressed by ligand binding [34-37]. Why these nuclear receptors use parallel molecular mechanisms to negatively regulate similar but distinct gene subsets in the same cell type remains an open and intriguing question [38, 39]. In our previous publication, we showed that 25HC is a potent agonist of LXR as others previously described, but 25HC3S is a potent antagonist [21]. In the present study we have shown that 25HC is a potent PPARγ antagonist and 25HC3S is a potent agonist. Thus, both of the oxysterols can regulate inflammatory responses but via two different pathways. 25HC can suppress inflammatory response via LXR signaling pathway but stimulate the response via PPARγ pathway; 25HC3S can suppress inflammatory response via PPARγ pathway but may interfere in a different direction by the LXR pathway. Several laboratories found that oxysterols including 25HC can activate LXRs, subsequently repress a set of inflammatory genes after LPS and cytokines stimulation [40, 41]. However, many other studies found that oxysterols including 25HC induce inflammation and oxidation in different kinds of cells. For example, 25HC substantially increased the IL-1β mRNA expression and secretion induced by LPS in human monocyte-derived macrophages. 25HC is also a potent inducer of MCP-1, MIP-1β and IL-8 secretion in vitro [41, 42]. 25HC treatments result in a significant increase in NFκB transcriptional activity, not only by affecting the IκB degradation and the translocation of p65/NFκB to the nucleus, but also by regulating the p65/NFκB transactivation [43]. Oxysterols also induce inflammation and oxidation through inducing slight mitochondrial dysfunctions and increasing reactive oxygen species (ROS) [43]. Previous study showed that PPARγ agonists increase LXR and ABCA1 mRNA levels following incubation with the agonists for 24 hrs [44]. It was assumed that PPARγ regulates inflammatory response through LXR pathway. However, if the cells were incubated with the agonists for short times (less than 6 hrs), the results were completely different [21]. Previous studies have shown that 25HC3S decreases LXR activities and its targeting gene expressions in macrophages. In contrast, LXR ligand, 25HC, increases nuclear LXR levels following short incubation time, subsequently increases LXR targeting gene expressions, inclusive of ABCA1/G1 and SREBP-1 mRNAs by 5-50-fold in 6 hrs. Furthermore, 25HC3S blocked the stimulation of target gene expressions induced by 25HC or artificial LXR agonist. It was concluded that 25HC3S activates PPARγ and modulates inflammatory response through PPARγ not LXR signaling pathway in the macrophages. The present studies provide a new clue of the role that oxysterols and oxysterol sulfation may play in inflammation regulation via activation/inactivation of the nuclear orphan receptors such as LXRs and PPARs.

Figure 26:
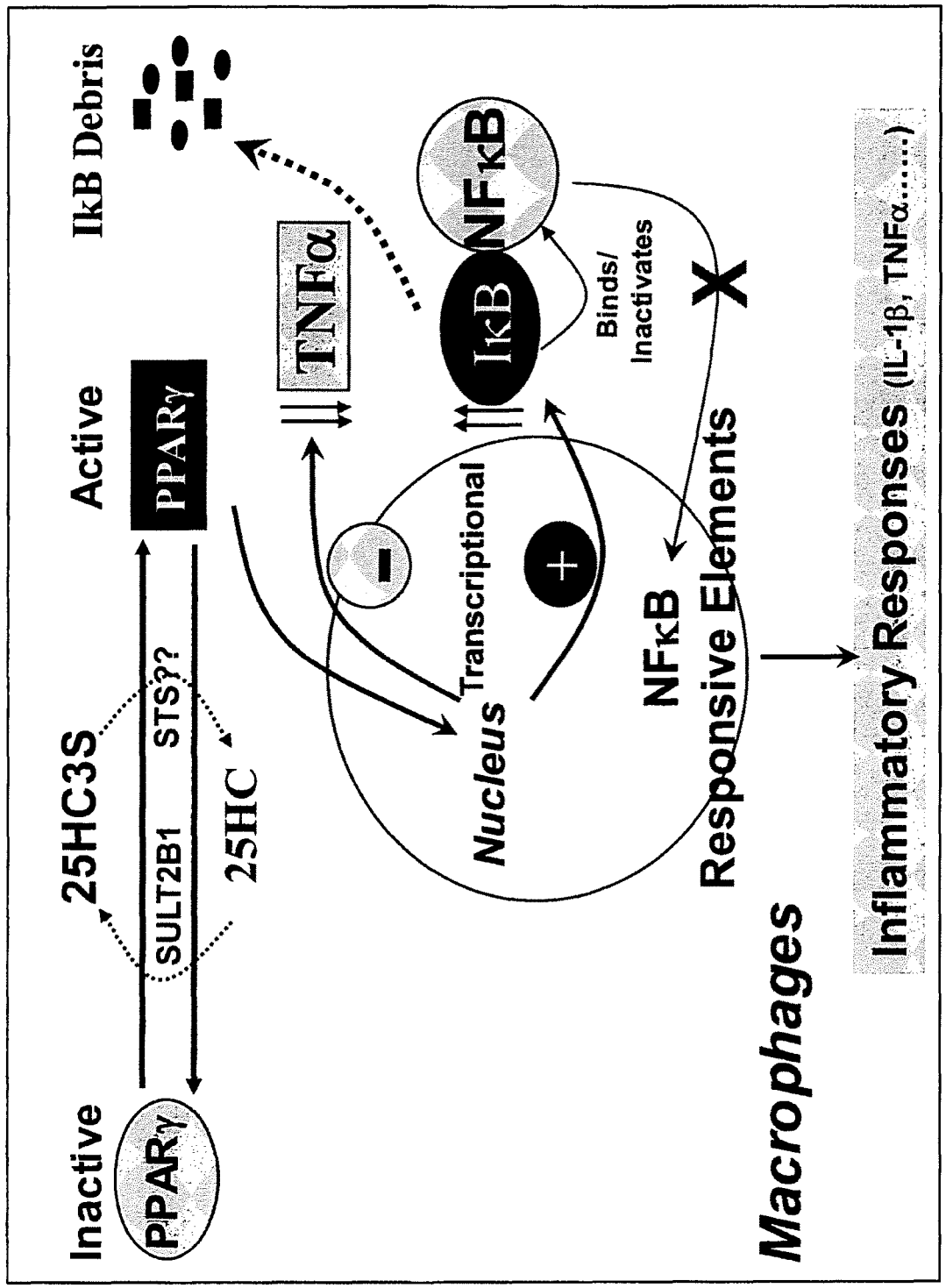
FIG. 26. Role of 25HC3S (oxysterol sulfation) in inflammatory response in THP-1 derived macrophages. 25-Hydroxycholesterol (25HC) is sulfated by a sulfotransferase SULT2B1 to form 25HC3S, and this reaction can be reversed by steroid sulfatase (STS). 25HC3S activates PPARγ and the activated PPARγ enters the nucleus where it up-regulates IκB expression and suppresses TNFα expression. As an inactive form, NFκB is bound by members of IκBs and sequestered in the cytoplasm. When TNFα levels are increased, it removes IκBs from NFκB by ubiquitination and degradation, and subsequently activates NFκB. The free active NFκB enters nuclei for stimulation of inflammatory response. Thus, 25HC3S represses inflammatory response by activating of PPARγ and subsequently suppressing TNFα and stimulating IκB expression. However, its precursor 25HC inactivates PPARγ and increases IκB degradation, which favors pro-inflammatory responses.
Figure 27A:
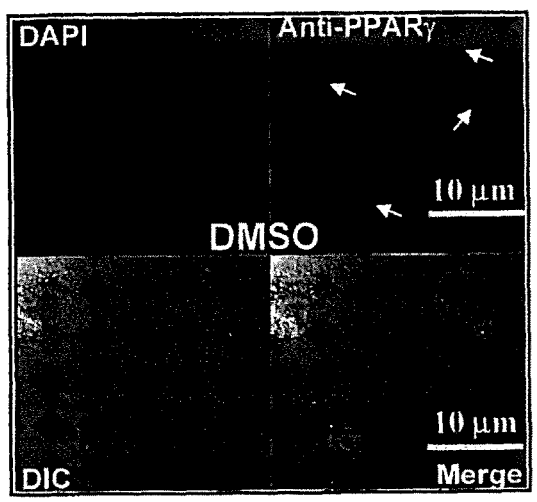
FIG. 27A-F. 25HC3S increases nuclear translocation of PPARγ in THP-1 macrophages. Confocal microscopy analysis of intracellular translocation of PPARγ protein distribution. The nuclear marker was stained with DAP1 and PPARγ protein was detected by anti-PPARγ immunofluorescence. For every figure, the top left panel shows nuclear staining; the top right panel shows the localization of PPARγ with the monoclonal antibody; the bottom right panel shows a differential interference contrast (DIC) image; the bottom right panel shows the merged image obtained by superimposing the three images mentioned above. Macrophages were treated with vehicle DMSO under 100× magnification (A) and 60× (B); treated with 25 μM of 25HC3S, 100× (D) and 60× (E); treated with 1 μM of T0070907 (C; preincubated with 1 μM of T0070907 for 2 hrs and cultured with 25HC3S for 4 hrs (F). The data represent one of three separate experiments. Scale bar=10 μm.
Figure 27B:
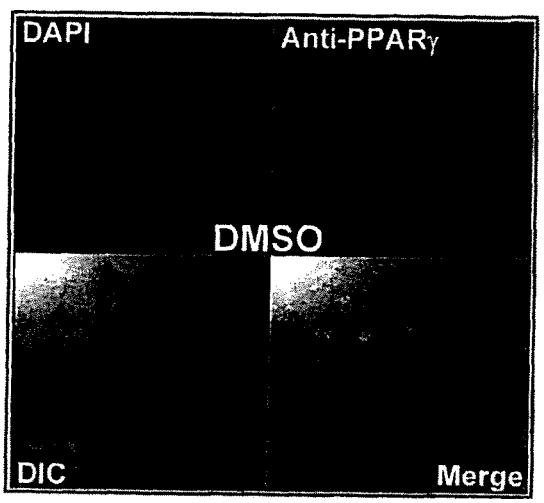
Figure 27C:
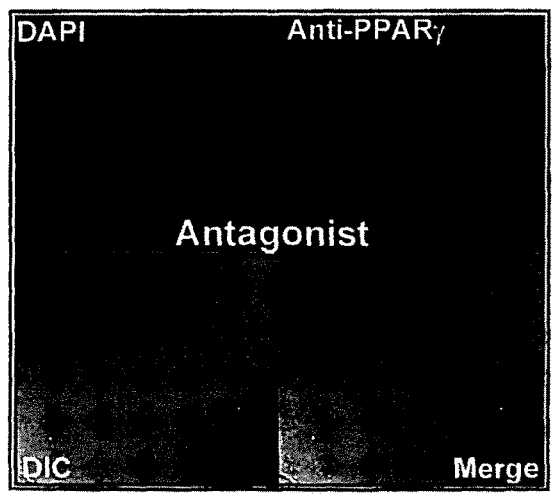
Figure 27D:
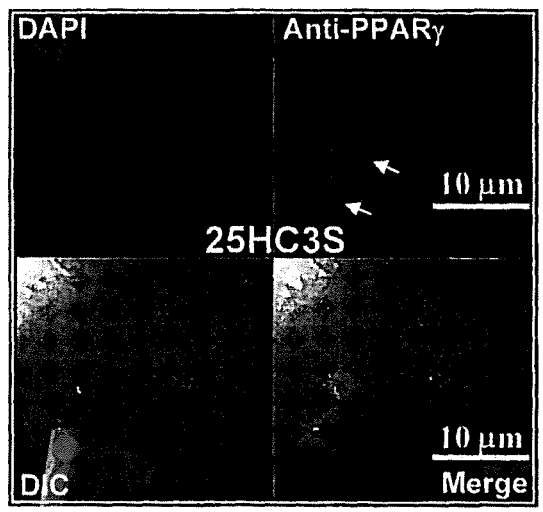
Figure 27E:
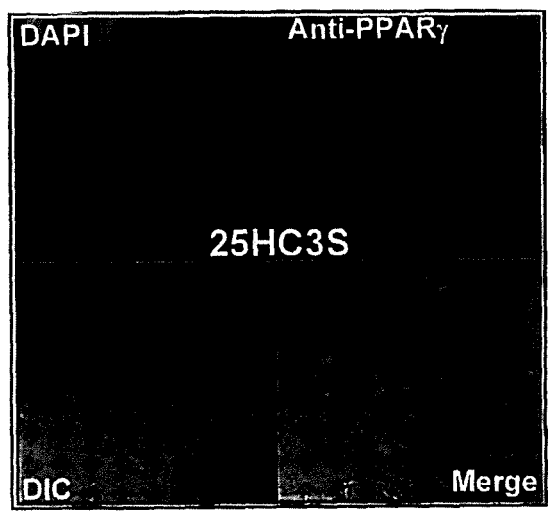
Figure 27F:
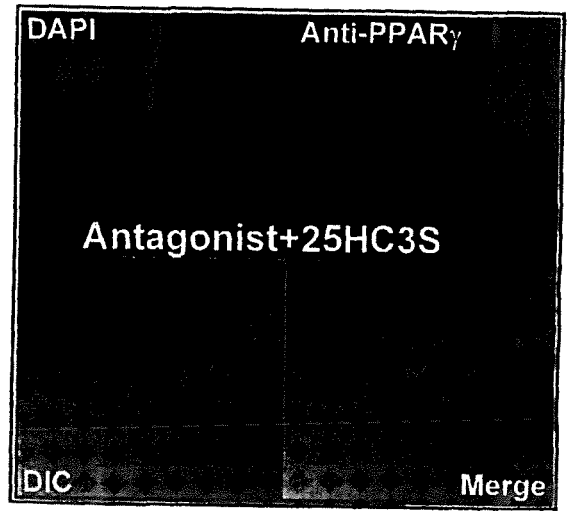

Previous studies have shown that PPARγ suppresses target gene expression of NFB, nuclear factor of activated T cells (NFAT), activator protein-1 (AP-1), and signal transducers and activator of transcription (STATs) in response to a variety of inflammatory stimuli, including cytokines and TLR ligands [45]. The mechanisms involved in the repressive effects of PPARγ have yet to be elucidated. In the present study, it has been found that 25HC3S increases PPARγ and decreases NFB protein levels in nuclei (FIGS. 21A and 21B and 23A and 23B); suppresses the expression of TNF-induced NFB dependent reporter gene, which is PPARγ-dependent (FIGS. 24A-24E); induces IB expression (FIGS. 25A-25C); and inhibits IL-1β and TNFα expression (FIGS. 22A-22E). It is possible that 25HC3S activates PPARγ, which induces IκB expression and inhibits IκB degradation by suppressing of TNF expression. IκB protein inhibits inflammatory responses by binding and inactivating NFB. Meanwhile, the activated PPARγ inhibits TNFα expression, which directly decreases IB ubiquitination and degradation. Thus, 25HC3S attenuates the inflammatory response by increasing IκB expression and decreasing IB ubiquitination and degradation through PPARγ/IB/NFB signaling pathway as shown in FIG. 26.

REFERENCES FOR EXAMPLE 6

1. B. Geeraert, K. D. De, P. C. Davey, F. Crombe, N. Benhabiles, and P. Holvoet, Oxidized low-density lipoprotein-induced expression of ABCA1 in blood monocytes precedes coronary atherosclerosis and is associated with plaque complexity in hypercholesterolemic pigs, J. Thromb. Haemost. 5 (2007) 2529.
2. A. Chawla, J. J. Repa, R. M. Evans, and D. J. Mangelsdorf, Nuclear receptors and lipid physiology: opening the X-files, Science 294 (2001) 1866.
3. S. J. Bensinger and P. Tontonoz, Integration of metabolism and inflammation by lipid-activated nuclear receptors, Nature 454 (2008) 470.
4. M. A. Bouhlel, B. Derudas, E. Rigamonti, R. Dievart, J. Brozek, S. Haulon, C. Zawadzki, B. Jude, G. Torpier, N. Marx, B. Staels, and G. Chinetti-Gbaguidi, PPARgamma activation primes human monocytes into alternative M2 macrophages with anti-inflammatory properties, Cell Metab 6 (2007) 137.
5. A. Castrillo and P. Tontonoz, PPARs in atherosclerosis: the clot thickens, J. Clin. Invest 114 (2004) 1538.
6. A. Chawla, W. A. Boisvert, C. H. Lee, B. A. Laffitte, Y. Barak, S. B. Joseph, D. Liao, L. Nagy, P. A. Edwards, L. K. Curtiss, R. M. Evans, and P. Tontonoz, A PPAR gamma-LXR-ABCA1 pathway in macrophages is involved in cholesterol efflux and atherogenesis, Mol. Cell 7 (2001) 161.
7. M. I. Dushkin, O. M. Khoshchenko, E. N. Posokhova, and Y. S. Schvarts, Agonists of PPAR-alpha, PPAR-gamma, and RXR inhibit the formation of foam cells from macrophages in mice with inflammation, Bull. Exp. Biol. Med. 144 (2007) 713.
8. J. I. Odegaard, R. R. Ricardo-Gonzalez, M. H. Goforth, C. R. Morel, V. Subramanian, L. Mukundan, A. R. Eagle, D. Vats, F. Brombacher, A. W. Ferrante, and A. Chawla, Macrophage-specific PPARgamma controls alternative activation and improves insulin resistance, Nature 447 (2007) 1116.
9. W. Ahmed, O. Ziouzenkova, J. Brown, P. Devchand, S. Francis, M. Kadakia, T. Kanda, G. Orasanu, M. Sharlach, F. Zandbergen, and J. Plutzky, PPARs and their metabolic modulation: new mechanisms for transcriptional regulation?, J. Intern. Med. 262 (2007) 184.
10. H. Martin, Role of PPAR-gamma in inflammation. Prospects for therapeutic intervention by food components, Mutat. Res. 669 (2009) 1.
11. L. Villacorta, F. J. Schopfer, J. Zhang, B. A. Freeman, and Y. E. Chen, PPARgamma and its ligands: therapeutic implications in cardiovascular disease, Clin. Sci. (Lond) 116 (2009) 205.
12. O. Nosjean and J. A. Boutin, Natural ligands of PPARgamma: are prostaglandin J(2) derivatives really playing the part?, Cell Signal. 14 (2002) 573.
13. J. Berger and D. E. Moller, The mechanisms of action of PPARs, Annu. Rev. Med. 53 (2002) 409.
14. C. Yu, L. Chen, H. Luo, J. Chen, F. Cheng, C. Gui, R. Zhang, J. Shen, K. Chen, H. Jiang, and X. Shen, Binding analyses between Human PPARgamma-LBD and ligands, Eur. J. Biochem. 271 (2004) 386.
15. M. J. DeGrazia, J. Thompson, J. P. Heuvel, and B. R. Peterson, Synthesis of a high-affinity fluorescent PPAR-gamma ligand for high-throughput fluorescence polarization assays, Bioorg. Med. Chem. 11 (2003) 4325.
16. O. Nosjean and J. A. Boutin, Natural ligands of PPAR-gamma: are prostaglandin J(2) derivatives really playing the part?, Cell Signal. 14 (2002) 573.
17. S. Gill, R. Chow, and A. J. Brown, Sterol regulators of cholesterol homeostasis and beyond: the oxysterol hypothesis revisited and revised, Prog. Lipid Res. 47 (2008) 391.
18. W. M. Pandak, S. Ren, D. Marques, E. Hall, K. Redford, D. Mallonee, P. Bohdan, D. Heuman, G. Gil, and P. Hylemon, Transport of cholesterol into mitochondria is rate-limiting for bile acid synthesis via the alternative pathway in primary rat hepatocytes, J. Biol. Chem. 277 (2002) 48158.
19. S. Ren, P. B. Hylemon, D. Marques, E. Gurley, P. Bodhan, E. Hall, K. Redford, G. Gil, and W. M. Pandak, Overexpression of cholesterol transporter StAR increases in vivo rates of bile acid synthesis in the rat and mouse, Hepatology 40 (2004) 910.
20. S. Ren, P. Hylemon, Z. P. Zhang, D. Rodriguez-Agudo, D. Marques, X. Li, H. Zhou, G. Gil, and W. M. Pandak, Identification of a novel sulfonated oxysterol, 5-cholesten-3beta,25-diol 3-sulfonate, in hepatocyte nuclei and mitochondria, J. Lipid Res. 47 (2006) 1081
21. Y. Ma, L. Xu, D. Rodriguez-Agudo, X. Li, D. M. Heuman, P. B. Hylemon, W. M. Pandak, and S. Ren, 25-Hydroxycholesterol-3-sulfate regulates macrophage lipid metabolism via the LXR/SREBP-1 signaling pathway, Am. J. Physiol Endocrinol. Metab 295 (2008) E1369-E1379.
22. X. Li, W. M. Pandak, S. K. Erickson, Y. Ma, L. Yin, P. Hylemon, and S. Ren, Biosynthesis of the regulatory oxysterol, 5-cholesten-3{beta},25-diol 3-sulfate, in hepatocytes, J. Lipid Res. 48 (2007) 2587.
23. W. Chen, G. Chen, D. L. Head, D. J. Mangelsdorf, and D. W. Russell, Enzymatic reduction of oxysterols impairs LXR signaling in cultured cells and the livers of mice, Cell Metab 5 (2007) 73.
24. S. Ren, X. Li, D. Rodriguez-Agudo, G. Gil, P. Hylemon, and W. M. Pandak, Sulfated oxysterol, 25HC3S, is a potent regulator of lipid metabolism in human hepatocytes, Biochem. Biophys. Res. Commun. 360 (2007) 802.
25. M. K. Heliovaara, A. M. Teppo, S. L. Karonen, and P. Ebeling, Inflammation affects lipid metabolism during recovery from hyperinsulinaemia, Eur. J. Clin. Invest 36 (2006) 860.
26. T. P. Erlinger, E. R. Miller, III, J. Charleston, and L. J. Appel, Inflammation modifies the effects of a reduced-fat low-cholesterol diet on lipids: results from the DASH-sodium trial, Circulation 108 (2003) 150.
27. W. Khovidhunkit, M. S. Kim, R. A. Memon, J. K. Shigenaga, A. H. Moser, K. R. Feingold, and C. Grunfeld, Effects of infection and inflammation on lipid and lipoprotein metabolism: mechanisms and consequences to the host, J. Lipid Res. 45 (2004) 1169.
28. K. A. von, M. Soller, and B. Brune, Peroxisome proliferator-activated receptor gamma (PPAR gamma) and sepsis, Arch. Immunol. Ther. Exp. (Warsz.) 55 (2007) 19.
29. A. Castrillo and P. Tontonoz, Nuclear receptors in macrophage biology: at the crossroads of lipid metabolism and inflammation, Annu. Rev. Cell Dev. Biol. 20 (2004) 455.
30. C. Zhang, D. L. Baker, S. Yasuda, N. Makarova, L. Balazs, L. R. Johnson, G. K. Marathe, T. M. McIntyre, Y. Xu, G. D. Prestwich, H. S. Byun, R. Bittman, and G. Tigyi, Lysophosphatidic acid induces neointima formation through PPARgamma activation, J. Exp. Med. 199 (2004) 763.
31. S. Ren, P. Hylemon, D. Marques, E. Hall, K. Redford, G. Gil, and W. M. Pandak, Effect of increasing the expression of cholesterol transporters (StAR, MLN64, and SCP-2) on bile acid synthesis, J. Lipid Res. 45 (2004) 2123.
32. J. Q. Jin, C. Q. Li, and L. C. He, Down-regulatory effect of usnic acid on nuclear factor-kappaB-dependent tumor necrosis factor-alpha and inducible nitric oxide synthase expression in lipopolysaccharide-stimulated macrophages RAW 264.7, Phytother. Res. (2008).

33. H. J. Hwang, H. J. Lee, C. J. Kim, I. Shim, and D. H. Hahm, Inhibitory Effect of Amygdalin on Lipopolysaccharide-inducible TNF-alpha and IL-1beta mRNA Expression and Carrageenan-induced Rat Arthritis, J. Microbiol. Biotechnol. 18 (2008) 1641.

34. F. Morello, E. Saglio, A. Noghero, D. Schiavone, T. A. Williams, A. Verhovez, F. Bussolino, F. Veglio, and P. Mulatero, LXR-activating oxysterols induce the expression of inflammatory markers in endothelial cells through LXR-independent mechanisms, Atherosclerosis 207 (2009) 38.

35. D. Torocsik, A. Szanto, and L. Nagy, Oxysterol signaling links cholesterol metabolism and inflammation via the liver X receptor in macrophages, Mol. Aspects Med. 30 (2009) 134.

36. C. Joffre, L. Leclere, B. Buteau, L. Martine, S. Cabaret, L. Malvitte, N. Acar, G. Lizard, A. Bron, C. Creuzot-Garcher, and L. Bretillon, Oxysterols induced inflammation and oxidation in primary porcine retinal pigment epithelial cells, Curr. Eye Res. 32 (2007) 271.

37. C. J. Delvecchio, P. Bilan, K. Radford, J. Stephen, B. L. Trigatti, G. Cox, K. Parameswaran, and J. P. Capone, Liver X receptor stimulates cholesterol efflux and inhibits expression of proinflammatory mediators in human airway smooth muscle cells, Mol. Endocrinol. 21 (2007) 1324.

38. A. Vejux, L. Malvitte, and G. Lizard, Side effects of oxysterols: cytotoxicity, oxidation, inflammation, and phospholipidosis, Braz. J. Med. Biol. Res. 41 (2008) 545.

39. I. Bjorkhem and U. Diczfalusy, Oxysterols: friends, foes, or just fellow passengers?, Arterioscler. Thromb. Vasc. Biol. 22 (2002) 734.

40. F. Morello, E. Saglio, A. Noghero, D. Schiavone, T. A. Williams, A. Verhovez, F. Bussolino, F. Veglio, and P. Mulatero, LXR-activating oxysterols induce the expression of inflammatory markers in endothelial cells through LXR-independent mechanisms, Atherosclerosis (2009).

41. T. Rosklint, B. G. Ohlsson, O. Wiklund, K. Noren, and L. M. Hulten, Oxysterols induce interleukin-1beta production in human macrophages, Eur. J. Clin. Invest 32 (2002) 35.

42. C. Prunet, T. Montange, A. Vejux, A. Laubriet, J. F. Rohmer, J. M. Riedinger, A. Athias, S. Lemaire-Ewing, D. Neel, J. M. Petit, E. Steinmetz, R. Brenot, P. Gambert, and G. Lizard, Multiplexed flow cytometric analyses of pro- and anti-inflammatory cytokines in the culture media of oxysterol-treated human monocytic cells and in the sera of atherosclerotic patients, Cytometry A 69 (2006) 359.

43. L. Calleros, M. Lasa, M. J. Toro, and A. Chiloeches, Low cell cholesterol levels increase NFkappaB activity through a p38 MAPK-dependent mechanism, Cell Signal. 18 (2006) 2292.

44. G. Chinetti, S. Lestavel, V. Bocher, A. T. Remaley, B. Neve, I. P. Torra, E. Teissier, A. Minnich, M. Jaye, N. Duverger, H. B. Brewer, J. C. Fruchart, V. Clavey, and B. Staels, PPAR-alpha and PPAR-gamma activators induce cholesterol removal from human macrophage foam cells through stimulation of the ABCA1 pathway, Nat. Med. 7 (2001) 53.

45. C. K. Glass and S. Ogawa, Combinatorial roles of nuclear receptors in inflammation and immunity, Nat. Rev. Immunol. 6 (2006) 44.

46. S. Ren, L. Xu, P. Hylemon, D. Heuman, W M. Pandak, 25-Hydroxycholesterol and 25-hyddoxycholesterol 3-sulfate reciprocally regulate lipid metabolism and inflammation in hepatorycetes and macrophages. The 60th Annual Meeting of the American Association for the Study of Liver Diseases, Boston, Mass., Oct 30-Nov 3, (2009), Hepatology 55 (4) (2009)16.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of decreasing fat accumulation in liver cells of a patient in need thereof, the method comprising administering a salt of 5-cholesten-3β, 25-diol 3-sulphate to the patient in an amount sufficient to decrease fat accumulation in the liver cells of the patient.

2. The method of claim 1, wherein the salt is selected from a sodium salt, a potassium salt, a calcium salt, a lithium salt, and an ammonium salt.

3. The method of claim 1, wherein the salt is a sodium salt.

4. The method of claim 1, wherein the fat comprises triglycerides.

5. The method of claim 2, wherein the fat comprises triglycerides.

6. The method of claim 3, wherein the fat comprises triglycerides.

* * * * *

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial
<220> FEATURE:
<223> OTHER INFORMATION: synthetic oligonucleotide forward primer

<400> SEQUENCE: 1
acctttccag agcaagcaca tt                                              22

<210> SEQ ID NO 2
<211> LENGTH: 22
<212> TYPE: DNA
<213> ORGANISM: Artificial
<220> FEATURE:
<223> OTHER INFORMATION: synthetic oligonucleotide reverse primer

<400> SEQUENCE: 2
aggacctaaa attgccattc ca                                              22
```